US012194248B2

(12) United States Patent
Northrop et al.

(10) Patent No.: US 12,194,248 B2
(45) Date of Patent: Jan. 14, 2025

(54) MEDICAL DEVICES WITH TUBULAR REINFORCEMENT

(71) Applicants:STRYKER CORPORATION, Kalamazoo, MI (US); STRYKER EUROPEAN OPERATIONS LIMITED, Carrigtwohill (IE)

(72) Inventors: Clay W. Northrop, Salt Lake City, UT (US); Ted W. Layman, Park City, UT (US); David P. Marceau, Salt Lake City, UT (US)

(73) Assignees: Stryker Corporation, Kalamazoo, MI (US); Stryker European Operations Limited, Carrigtwohill (IE)

( * ) Notice: Subject to any disclaimer, the term of this patent is extended or adjusted under 35 U.S.C. 154(b) by 0 days.

(21) Appl. No.: 18/585,729

(22) Filed: Feb. 23, 2024

(65) Prior Publication Data

US 2024/0238556 A1    Jul. 18, 2024

Related U.S. Application Data

(63) Continuation of application No. 18/339,039, filed on Jun. 21, 2023, which is a continuation of application No. PCT/US2021/065252, filed on Dec. 27, 2021.
(Continued)

(51) Int. Cl.
*A61M 25/00* (2006.01)
*A61M 25/01* (2006.01)
*B28B 21/00* (2006.01)

(52) U.S. Cl.
CPC .... *A61M 25/0051* (2013.01); *A61M 25/0013* (2013.01); *A61M 25/0054* (2013.01);
(Continued)

(58) Field of Classification Search
CPC .......... A61M 25/0051; A61M 25/0013; A61M 25/0054; A61M 25/0068; A61M 25/0138;
(Continued)

(56) References Cited

U.S. PATENT DOCUMENTS 6,033,394 A * 3/2000 Vidlund ............ A61M 25/0052
604/524
9,067,332 B2    6/2015 Lippert et al.
(Continued)

FOREIGN PATENT DOCUMENTS

AU    2016 209 354    8/2017
EP    3 169 393    5/2017
(Continued)

OTHER PUBLICATIONS

PCT International Search Report and Written Opinion for PCT/US2021/065252, Applicant: Stryker Corporation, Form PCT/ISA/210, 220 and PCT/ISA/237, dated May 16, 2022 (16 pages).

*Primary Examiner* — Christopher W Raimund
(74) *Attorney, Agent, or Firm* — Vista IP Law Group, LLP

(57) ABSTRACT

A method of making a medical device includes: obtaining an assembly having a tubular structure, a polymeric tube, and a stretched rod, wherein the stretched rod is inside a lumen of the polymeric tube, and wherein the polymeric tube is between the tubular structure and the stretched rod; and expanding the stretched rod to urge the polymeric tube radially outward towards an inner surface of the tubular structure.

28 Claims, 46 Drawing Sheets

Related U.S. Application Data

(60) Provisional application No. 63/234,165, filed on Aug. 17, 2021, provisional application No. 63/131,767, filed on Dec. 29, 2020.

(52) U.S. Cl.
CPC ......... *A61M 25/0068* (2013.01); *B28B 21/00* (2013.01); *A61M 25/0138* (2013.01)

(58) Field of Classification Search
CPC .... A61M 25/005; B28B 21/00; A61F 2/2427; A61F 2/95; A61F 2210/0076
See application file for complete search history.

(56) References Cited

U.S. PATENT DOCUMENTS

| | | |
|---|---|---|
| 11,406,791 B2 | 8/2022 | Lippert et al. |
| 2003/0097119 A1* | 5/2003 | Garabedian ......... A61M 25/005 |
| | | 604/524 |
| 2014/0352871 A1* | 12/2014 | Wang ................... F16L 11/121 |
| | | 156/190 |
| 2016/0015928 A1* | 1/2016 | Northrop .......... A61M 25/0054 |
| | | 264/134 |
| 2020/0345975 A1 | 11/2020 | Snyder |

FOREIGN PATENT DOCUMENTS

| | | |
|---|---|---|
| WO | WO 99/29361 | 6/1999 |
| WO | WO 2020/05548 A1 | 3/2020 |

\* cited by examiner

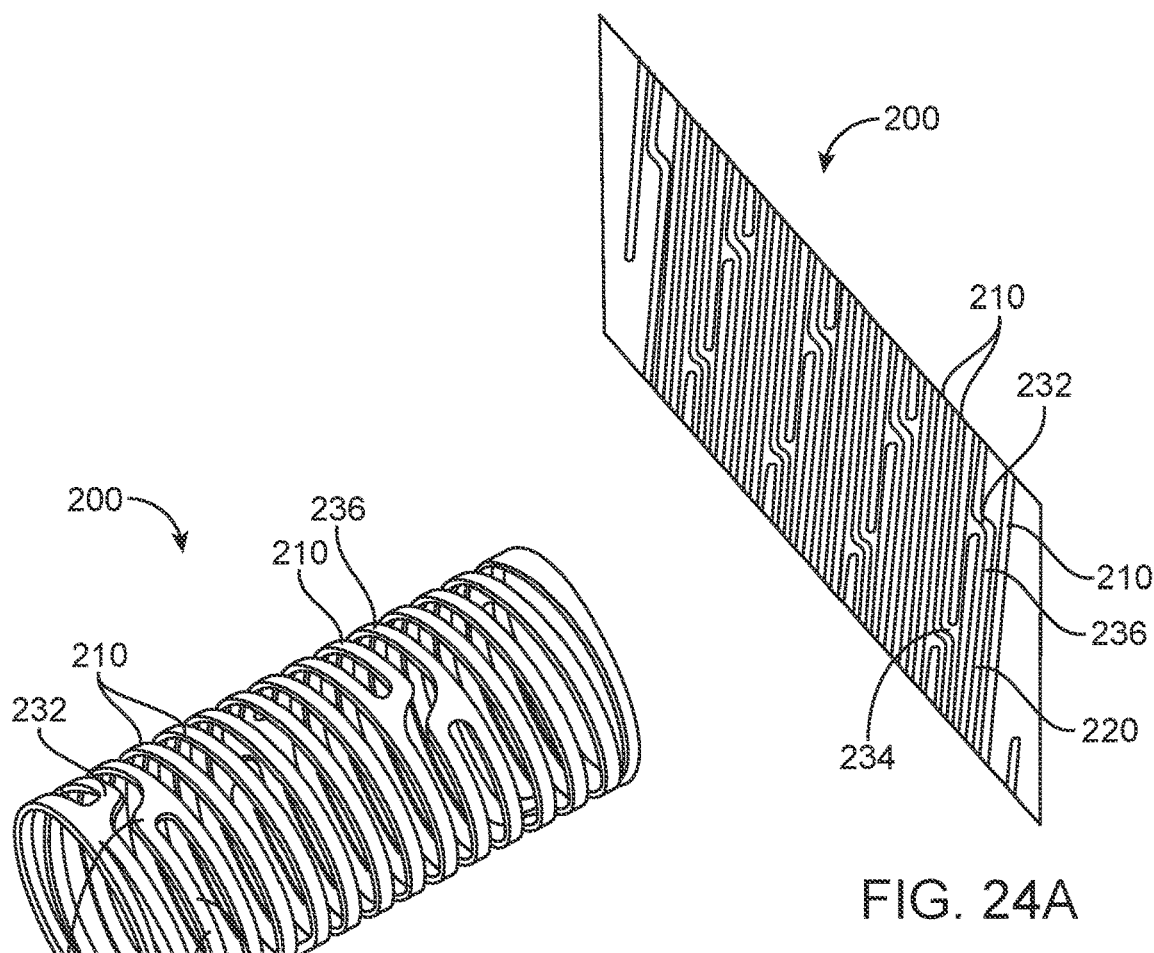
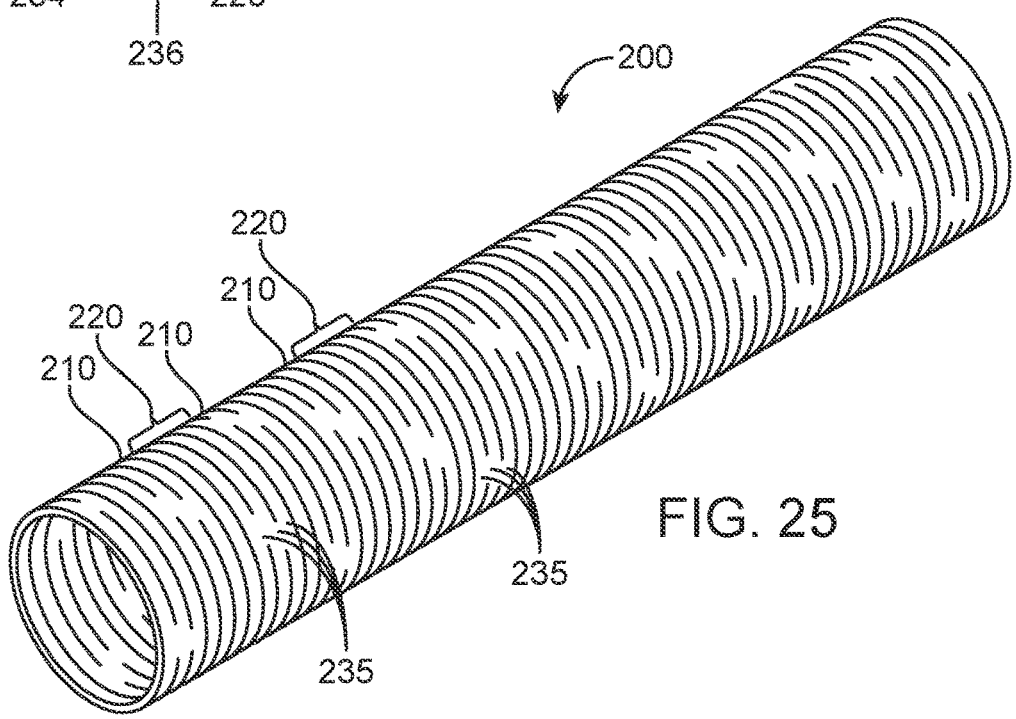
FIG. 24A
FIG. 24B
FIG. 25

| Angle φ | radians | Length 0.005 away | % strain 0.005 away | length 0.030 away | % strain 0.030 away | length 0.060 away | % strain 0.060 away |
|---|---|---|---|---|---|---|---|
| 0 | 0 | 0.002 | 0% | 0.002 | 0% | 0.002 | 0% |
| 2 | 0.034907 | 0.002174 | 9% | 0.003047 | 52% | 0.004094 | 105% |
| 4 | 0.069813 | 0.002349 | 17% | 0.004093 | 105% | 0.006185 | 209% |
| 6 | 0.10472 | 0.002523 | 26% | 0.005136 | 157% | 0.008272 | 314% |
| 8 | 0.139626 | 0.002696 | 35% | 0.006175 | 209% | 0.01035 | 418% |
| 10 | 0.174533 | 0.002868 | 43% | 0.007209 | 260% | 0.012419 | 521% |
| 12 | 0.20944 | 0.00304 | 52% | 0.008237 | 312% | 0.014475 | 624% |
| 14 | 0.244346 | 0.00321 | 60% | 0.009258 | 363% | 0.016515 | 726% |
| 16 | 0.279253 | 0.003378 | 69% | 0.010269 | 413% | 0.018538 | 827% |
| 18 | 0.314159 | 0.003545 | 77% | 0.011271 | 464% | 0.020541 | 927% |
| 20 | 0.349066 | 0.00371 | 86% | 0.012261 | 513% | 0.022521 | 1026% |

FIG. 31

| Angle φ | radians | Length 0.005 away | % strain 0.005 away | length 0.030 away | % strain 0.030 away | length 0.060 away | % strain 0.060 away |
|---|---|---|---|---|---|---|---|
| 10 | 0.174533 | 0.002868 | 0% | 0.007209 | 0% | 0.012419 | 0% |
| 12 | 0.20944 | 0.00304 | 6% | 0.008237 | 14% | 0.014475 | 17% |
| 14 | 0.244346 | 0.00321 | 12% | 0.009258 | 28% | 0.016515 | 33% |
| 16 | 0.279253 | 0.003378 | 18% | 0.010269 | 42% | 0.018538 | 49% |
| 18 | 0.314159 | 0.003545 | 24% | 0.011271 | 56% | 0.020541 | 65% |
| 20 | 0.349066 | 0.00371 | 29% | 0.012261 | 70% | 0.022521 | 81% |
| 22 | 0.383972 | 0.003873 | 35% | 0.013238 | 84% | 0.024476 | 97% |
| 24 | 0.418879 | 0.004034 | 41% | 0.014202 | 97% | 0.026404 | 113% |
| 26 | 0.453786 | 0.004192 | 46% | 0.015151 | 110% | 0.028302 | 128% |
| 28 | 0.488692 | 0.004347 | 52% | 0.016084 | 123% | 0.030168 | 143% |
| 30 | 0.523599 | 0.0045 | 57% | 0.017 | 136% | 0.032 | 158% |

FIG. 32

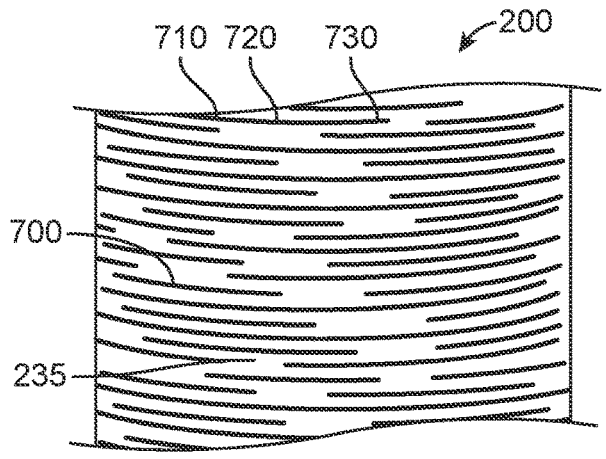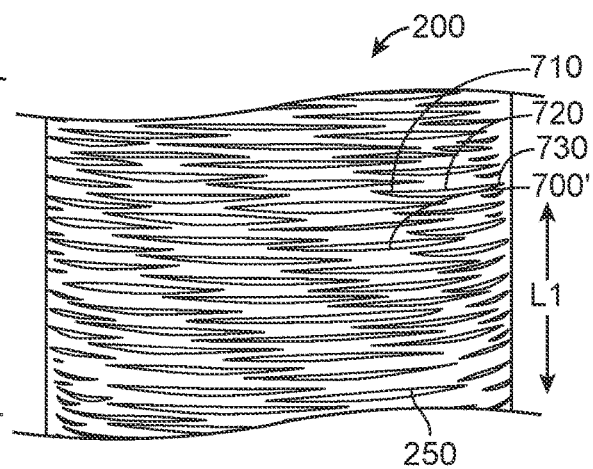
FIG. 36A  FIG. 36B
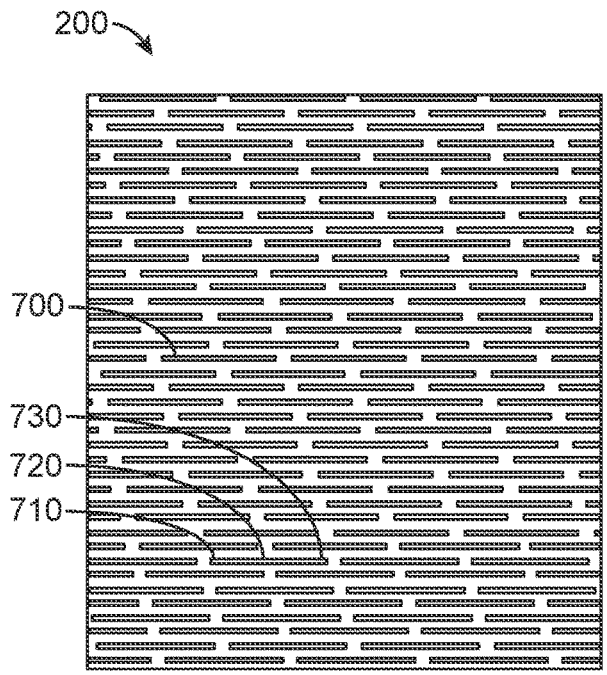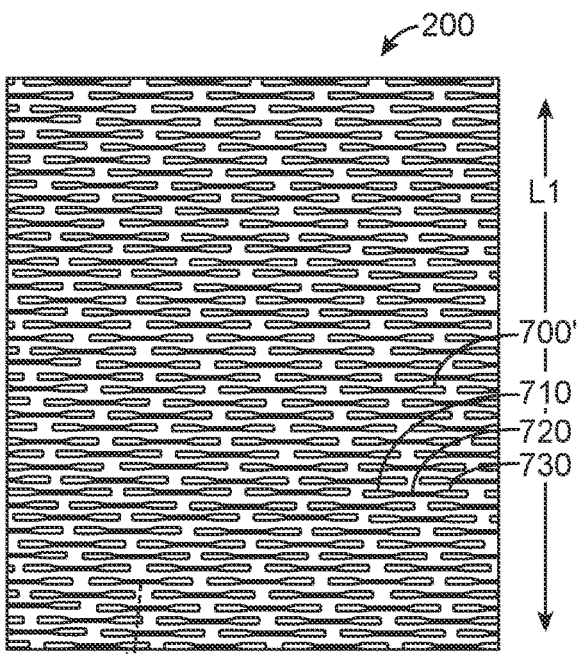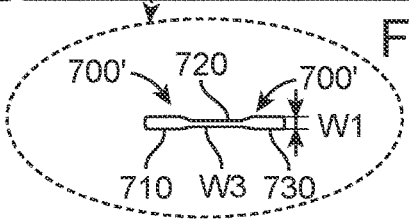
FIG. 37A  FIG. 37B

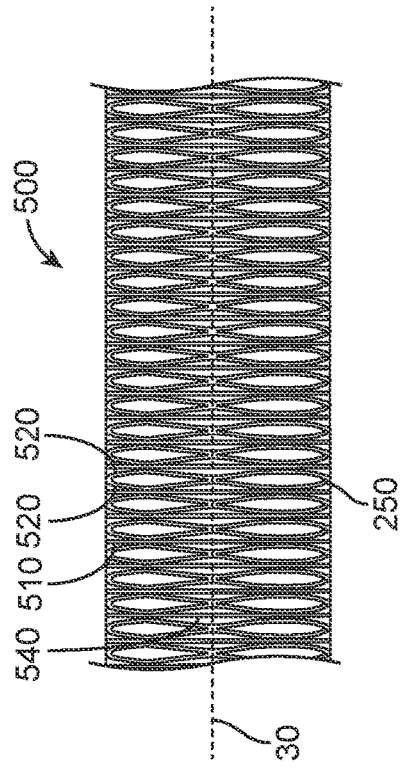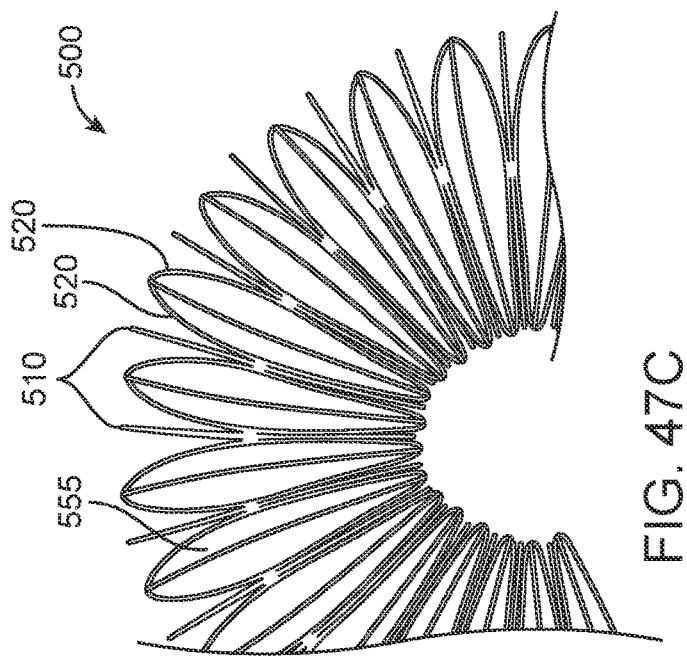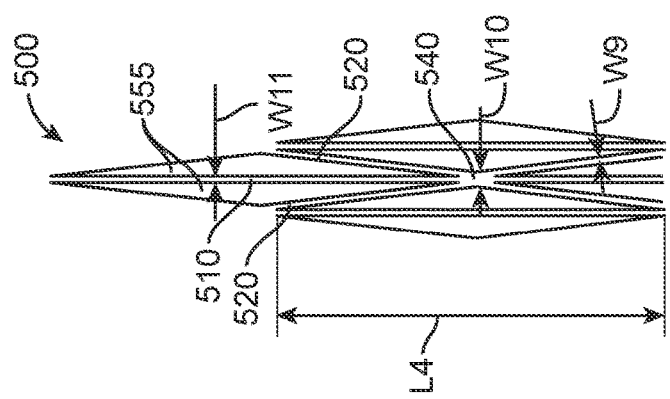

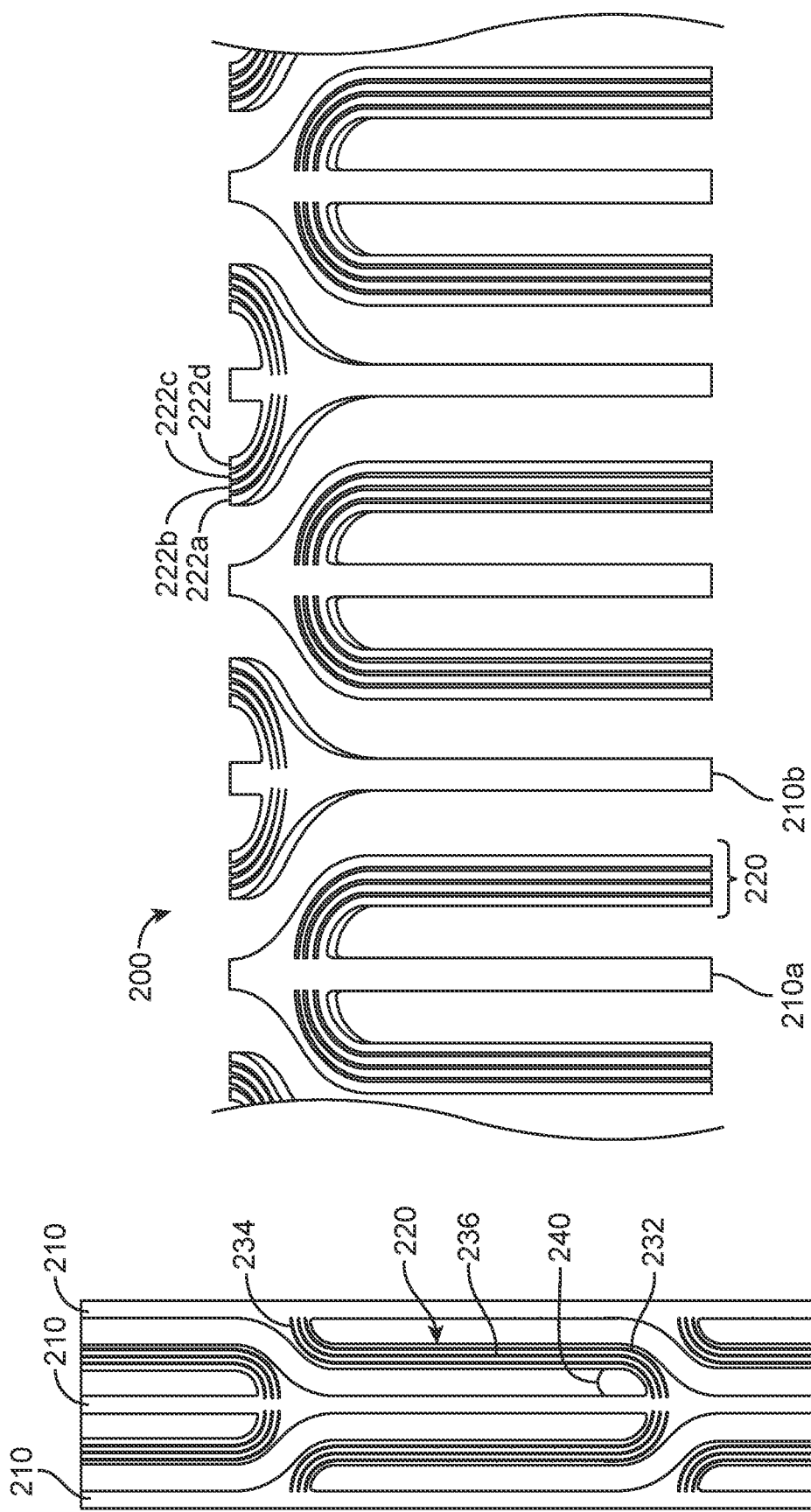

MEDICAL DEVICES WITH TUBULAR REINFORCEMENT

RELATED APPLICATION DATA

This application is a continuation of U.S. patent application Ser. No. 18/339,039, filed on Jun. 21, 2023, pending, which is a continuation of International Patent Application No. PCT/US2021/065252, filed on Dec. 27, 2021, which claims priority to U.S. Provisional Patent Application No. 63/234,165, filed Aug. 17, 2021, and U.S. Provisional Patent Application No. 63/131,767, filed Dec. 29, 2020, the disclosures of all of which are hereby incorporated herein by reference in their entirety into the present application.

FIELD

The present disclosure relates generally to minimally invasive medical devices, and more specifically to catheters.

BACKGROUND

The use of intravascular catheters for accessing and treating various types of diseases, such as vascular defects, is well-known. For example, a suitable intravascular catheter may be inserted into the vascular system of a patient. Commonly used vascular application to access a target site in a patient involves inserting a guidewire through an incision in the femoral artery near the groin, and advancing the guidewire until it reaches the target site. Then, a catheter is advanced over the guidewire until an open distal end of the catheter is disposed at the target site. Simultaneously or after placement of the distal end of the catheter at the target site, an intravascular implant is advanced through the catheter via a delivery wire.

In certain applications, such as neurovascular treatment, the catheters are required to navigate tortuous and intricate vasculature. By using an appropriately sized device having the requisite performance characteristics, such as "pushability" "steerability", "torqueability" and most important, distal tip flexibility, virtually any target site in the vascular system may be accessed, including that within the tortuous cerebral and peripheral vasculature. Further, the forces applied at the proximal end of these catheters should be transferred to the distal ends for suitable pushability (axial rigidity) and torqueability (rotation). Achieving a balance between these features is highly desirable, but difficult.

Also, a catheter may have a lumen with a certain cross-sectional shape. During use, the catheter may be bent. For example, tensioning wire may be operated to bend the catheter, and/or the catheter may be bent via guidewire or by a curvature of an anatomy. The bending of the catheter causes a compression on one side of the catheter and tension on an opposite side of the catheter. In some cases, due to the compression associated with the bending of the catheter, the catheter may kink, thereby collapsing the lumen of the catheter. Designing a catheter to resist such kinking while achieving certain bending flexibility and torsional rigidity is very difficult to accomplish.

SUMMARY

A catheter includes: a tubular structure having a distal end, a proximal end, and a body extending between the distal end and the proximal end, the tubular structure having a longitudinal axis; wherein the tubular structure comprises a plurality of ring elements arranged in series along the longitudinal axis, the ring elements being respective closed-loops, wherein the ring elements comprise a first ring element and a second ring element, wherein the first ring element lies within a first plane that is substantially perpendicular to the longitudinal axis of the tubular structure, and wherein the second ring element lies within a second plane that is substantially perpendicular to the longitudinal axis of the tubular structure; wherein the tubular structure further comprises connecting members, the connecting members comprising a first connecting member connected between the first ring element and the second ring element, wherein the first connecting member comprises a first member end, a second member end, and a member body between the first member end and the second member end; and wherein the first member end of the first connecting member is connected to the first ring element, wherein the second member end of the first connecting member is connected to the second ring element, and wherein the member body is configured to rotate and/or bend relative to the first ring element and the second ring element in response to a bending and/or axial loading of the tubular structure.

Optionally, the catheter comprises a lumen having a cross-sectional shape when the catheter is in a relaxed state, and wherein the tubular structure is configured to maintain the cross-sectional shape of the lumen during bending of the catheter.

Optionally, the tubular structure is configured to provide axial stiffness and/or torsional stiffness for the catheter.

Optionally, the first member end of the first connecting member and the second member end of the first connecting member define a line that is non-parallel to the longitudinal axis of the tubular structure.

Optionally, the first plane and the second plane remain substantially perpendicular to the longitudinal axis when the tubular structure is being bent and/or being axially-loaded.

Optionally, the first ring element has an uniform cross-section.

Optionally, the first ring element has different cross-sectional dimensions along a length of the first ring element.

Optionally, the first ring element has multiple segments connected together, each of the multiple segments having a paddle-shape.

Optionally, a majority of the first connecting member lies in a third plane that is parallel to the first plane when the tubular structure is in a relaxed state.

Optionally, at least a portion of the first connecting member has a curvilinear configuration.

Optionally, the first ring elements comprises a first ring segment and a second ring segment; wherein the first ring segment has a first end and a second end that is larger than the first end; wherein the second ring segment has a first end and a second end that is larger than the first end of the second ring segment; and wherein the first end of the second ring segment is connected to the second end of the first ring segment.

Optionally, the first connecting member extends from the first end of the second ring segment.

Optionally, the connecting members also comprise a second connecting member, and wherein both the first and second connecting members are located between the first ring element and the second ring element.

Optionally, the first and second connecting members comprise respective interlocks that are in abutment engagement with respect to each other to limit an amount of bending and/or stretching of the tubular structure.

Optionally, the connecting members also comprise a second connecting member, wherein the first and second connecting members are connected to a same location at the first ring element.

Optionally, the ring elements and the connecting members are integrally formed together.

Optionally, the ring elements and the connecting members are parts of a cut tube.

Optionally, a portion of the first ring element and a portion of the first connecting member are separated from each other to define a first space, and wherein the catheter further comprises a filler located in the space.

Optionally, the portion of the first connecting member is separated from the second ring to define a second space, wherein the first space and the second space has a same width.

Optionally, the catheter further includes a layer disposed on an outer surface or an inner surface of the tubular structure.

Optionally, the layer of the catheter includes a material that extends into a spacing to form a filler between a portion of the first ring element and a portion of the first connecting member.

Optionally, the tubular structure and the layer are configured to cooperate with each other by sharing tensile load and/or bending load.

Optionally, the connecting members of the catheter also include a second connecting member and a third connecting member, and wherein the first connecting member, the second connecting member, and the third connecting member are coupled between the first ring element and the second ring element.

Optionally, the connecting members include three pairs of connecting members or more, and wherein the first connecting member, the second connecting member, and the third connecting member are respectively in the three pairs of the connecting members.

Optionally, the first connecting member has a width that is less than 0.005 inch.

Optionally, the filler comprises a polymeric material.

Optionally, the first connecting member comprises a plurality of sub-connecting members.

Optionally, majority parts of the respective sub-connecting members are substantially parallel to each other.

Optionally, the plurality of sub-connecting members comprises 2, 3, or 4 sub-connecting members.

Optionally, the sub-connecting members are parts of a structure that is cut to form the sub-connecting members.

Optionally, at last one of the sub-connecting members has a cross-sectional shape with a thickness and a width, wherein the thickness is measured along a radial direction extending from the longitudinal axis of the tubular structure, wherein the width is measured along a direction that is perpendicular to the radial direction, and wherein the width is greater than the thickness.

Optionally, at last one of the sub-connecting members has a cross-sectional shape with a thickness and a width, wherein the thickness is measured along a radial direction extending from the longitudinal axis of the tubular structure, wherein the width is measured along a direction that is perpendicular to the radial direction, and wherein the width is greater than the thickness.

A catheter includes: a tubular structure having a distal end, a proximal end, and a body extending between the distal end and the proximal end; wherein the tubular structure comprises a configuration shown in any of the FIGS. 2-3 and 5-20.

Other and further aspects and features of embodiments will become apparent from the ensuing detailed description in view of the accompanying figures.

BRIEF DESCRIPTION OF THE FIGURES

FIGS. 24A-24B illustrate another tubular structure and a 2D pattern of the same.

FIG. 25 illustrates another tubular structure.

FIG. 31 illustrates a data table of stretching percentage of a polymer of the tubular structure of FIG. 29A-29B.

FIG. 32 illustrates a data table of stretching percentage of a polymer of the tubular structure of FIG. 30A-30B.

FIGS. 36A-36B illustrate another tubular structure in respective relaxed and stretched configurations.

FIGS. 37A-37B illustrate another tubular structure in respective relaxed and stretched configurations.

FIGS. 47A-47C illustrate another tubular structure and bending of the same.

FIG. 48 illustrates another 2D pattern of a tubular structure.

FIG. 49 illustrates of the tubular structure of FIG. 48.

DETAILED DESCRIPTION

Figure 1:
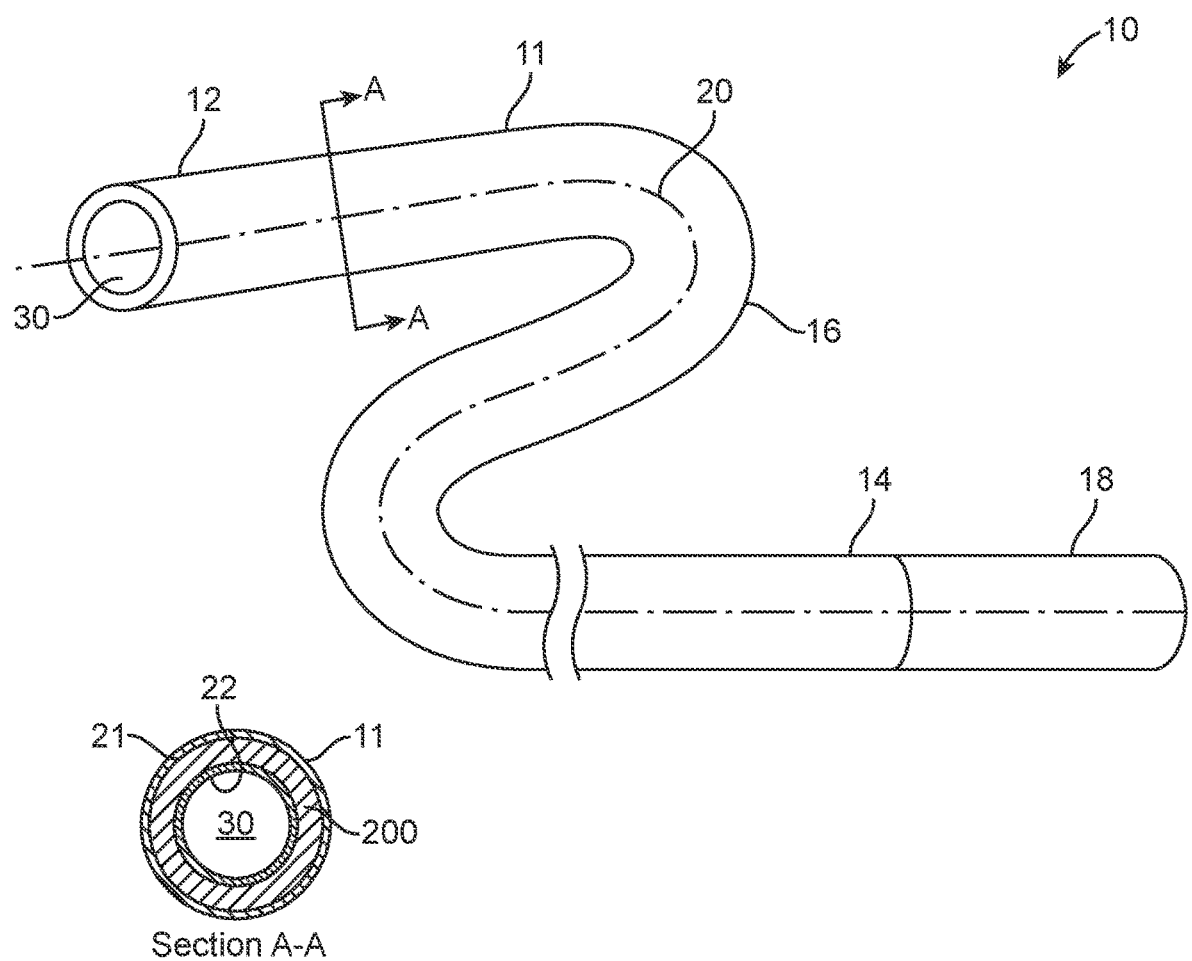
FIG. 1 illustrates a catheter in accordance with some embodiments.

Various embodiments are described hereinafter with reference to the figures. It should be noted that the figures are not drawn to scale and that elements of similar structures or functions are represented by the same reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the term "about" may include numbers that are rounded to the nearest significant figure. In some cases, the term "about" may refer to a range of values that are within +/−10% of a value. For example, a value of 2 or a value of about 2 may refer to any value that is within the range of 2+/−10% (=2+/−0.2=1.8 to 2.2).

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

FIG. 1 illustrates a catheter 10 in accordance with some embodiments. The catheter 10 includes a tube 11 having a distal end 12, a proximal end 14, and a tube body 16 extending between the distal end 12 and the proximal end 14. The catheter 10 also includes a handle 18 attached to the proximal end 14 of the tube 11.

The distal end 12 of the catheter 10 is more flexible than the tube body 16 and the proximal end 14, and the proximal end 14 is stiffer and typically less flexible than the tube body 16. Although the distal end 12, the proximal end 14, and the tube body 16 may be considered as distinct sections of the catheter 10, the transition between these sections is smooth and substantially gradual. Usually, the typical dimensions of the catheter 10 are: overall length: 125-200 cm; proximal end 14:50-150 cm; tube body 16:5-100 cm; and distal end 12:2-30 cm. It should be appreciated that these dimensions are only guidelines and are selected as a function of the condition to be treated and its site within the body.

The tube 11 includes an outer surface 21, and inner surface 22, and a lumen 30 defined by the inner surface. The tube 11 also includes a tubular structure 200 configured to provide certain stiffness for the tube 11. As shown in the figure, the tubular structure 200 is disposed between the outer surface 21 and the inner surface 22 of the tube 11, so that the tubular structure 200 is embedded within a wall of the tube 11. In other embodiments, the tubular structure 200 may be on the outer surface 21, or on the inner surface 22 of the tube 11. The tubular structure 200 has a distal end, a proximal end, and a body extending between the distal end and the proximal end. The tubular structure 200 also has a longitudinal axis 20 defined by the distal end and the proximal end of the tubular structure 200.

In the illustrated embodiments, the lumen 30 of the catheter 10 has a cross-sectional shape when the catheter 10 is in a relaxed state. The tubular structure 200 is configured to maintain the cross-sectional shape of the lumen 30 (Section A-A) during bending of the catheter 10, so that the catheter 10 will not kink. Optionally, the tubular structure 200 may also be configured to provide axial stiffness (e.g., tension/compression along the longitudinal axis 20) and/or torsional stiffness (e.g., bending) for the catheter 10.

Any of the tubular structures 200 and/or further embodiments of the tubular structure disclosed herein or combination thereof, are configured to be disposed at the distal end 12, the tube body 16 and/or the proximal end 14 of the catheter 10 depending on the desired flexibility, stiffness, and other features, such as tracking, pushability, among others.

The outer surface 21 and/or the inner surface 22 of the tube 11 may be formed by a filler. Any of the tubular structures 200 and/or further embodiments of the tubular structure disclosed herein or combination thereof, the filler and the tubular structure behave as a composite by sharing tensile and bending loads between the filler and tubular structure, as it will be described in further detail below.

In some embodiments, the filler forming part of the tube 11 may have a modulus of elasticity that is lower than the modulus of elasticity of the tubular structure 200. For example, the filler may have a modulus of elasticity that is less than 50%, or more preferably less than 30%, or more preferably less than 20%, or more preferably less than 10%, or more preferably less than 5%, or more preferably less than 1%, of that of the tubular structure 200. In one implementation, the filler may have a modulus of elasticity that is less than 15 Mpa (e.g., 10 Mpa or less).

Also, the filler forming part of the tube 11 may have the ability to undergo significant elongation before break point. For example, in some embodiments, the filler may be capable of having a strain (defined as an amount of elongation of the material divided by the length of the material) of at least: 20%, 40%, 60%, 80%, 100%, 200%, 300%, 400%, 500%, 600%, 700%, 800%, 900%, 1000%, or greater.

Various materials may be utilized as the filler. The filler may be made from polymer, plastic, foam, polymeric solution or any of other elastic materials. By means of non-limiting examples, the filler material may include polyurethane, polyurethane-based material, silicon-based material, any material having polyurethane dispersion or silicon-based dispersion, etc. Examples of filler material that may be used include CD102® or AD111® from Covestro, Gelest Ex-sil50® from Gelest, etc.

In some embodiments, because the filler is significantly softer than the material of the tubular structure 200, the resulting tube 11 will have one or more mechanical properties that are contributed predominantly (e.g., more than 50%, more than 60%, more than 70%, more than 80%, more than 90%, more than 95%, more than 99%, etc.) by the tubular structure 200. By means of non-limiting examples, the one or more mechanical properties may be a bending stiffness, an axial stiffness, a torsional stiffness, a shear stiffness, or any combination of the foregoing.

In one or more embodiments, the tube 11 may optionally further include a lubricious coating (e.g. hydrophilic or any other suitable coating) that is disposed on the exterior surface of the tube 11 and/or on the interior surface of the tube 11. In some cases, an initial coating material may first be applied on the tubular structure 200 to fill the openings at the wall of the tubular structure 200, and optionally to cover the exterior and/or interior surface of the tubular structure 200. Then the lubricious coating is applied over the initial coating material.

Constructing the tube 11 using the tubular structure 200 (providing a majority of the mechanical properties), and using the very soft filler material, is advantageous because it prevents the distal end of the tube 11 from being too stiff, and because it allows design of catheter to be easier with resulting behavior of the catheter being more predictable (because computational modeling of the catheter may be made based on the tubular structure design only).

Figure 2A:
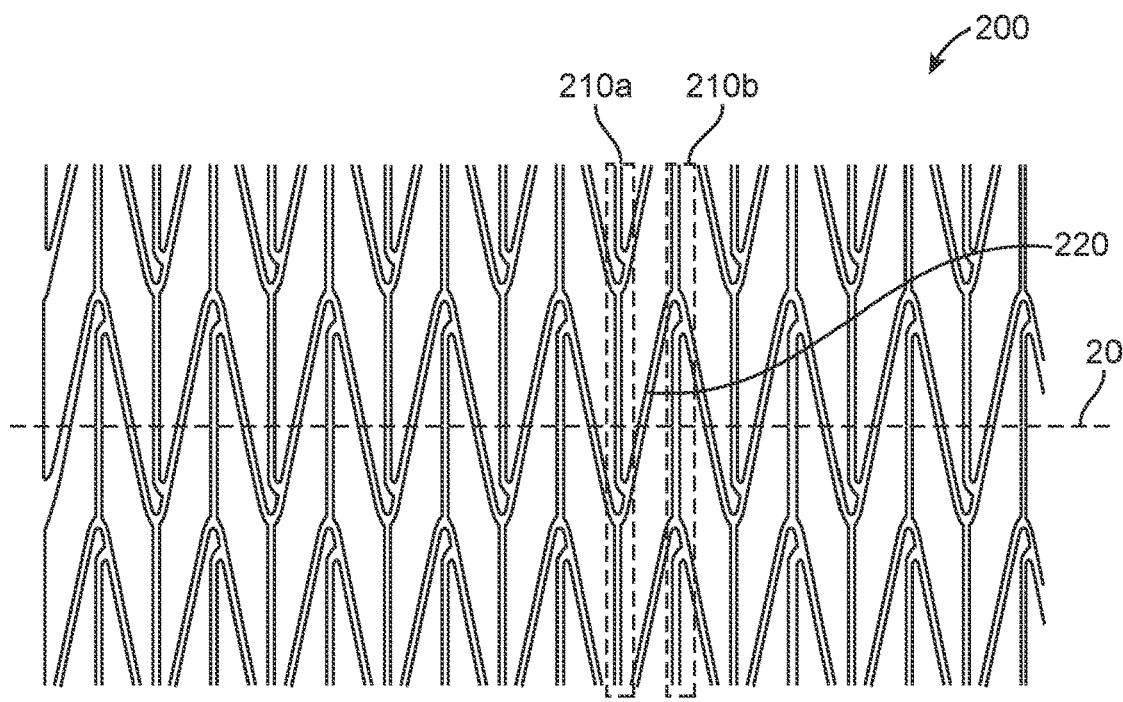
FIGS. 2A-2B illustrate a part of a tubular structure of the catheter of FIG. 1.
Figure 2B:
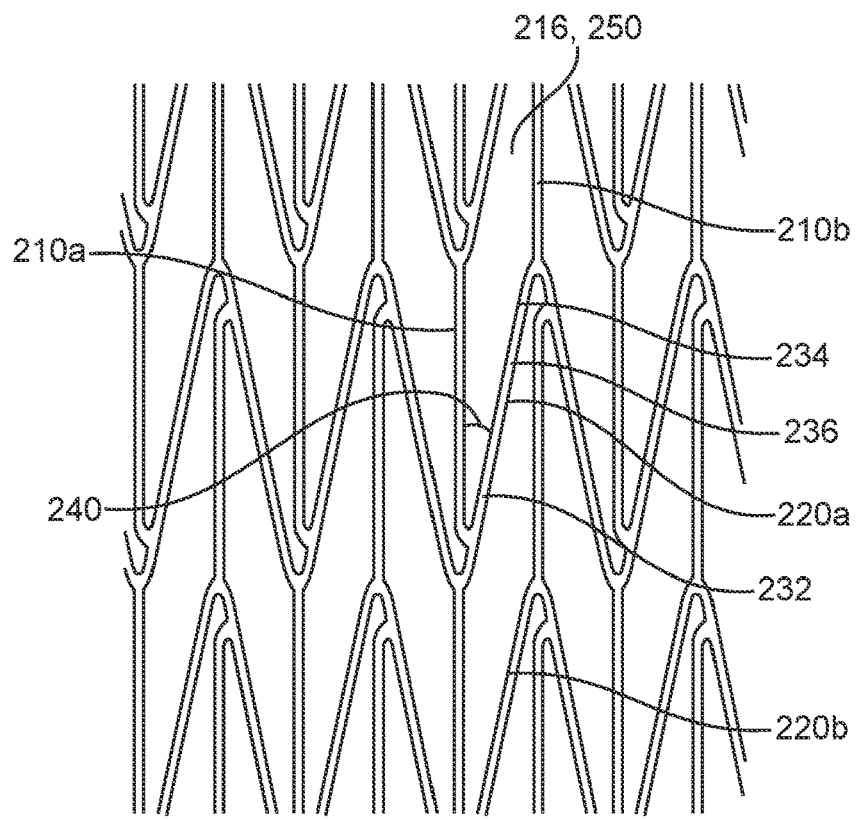

FIGS. 2A-2B illustrate a part of a tubular structure 200 of the catheter 10 of FIG. 1. The tubular structure 200 has a plurality of ring elements 210 arranged in series along the longitudinal axis 20. In the illustrated embodiments, the ring elements 210 are respective closed-loops. In FIGS. 2A-2B, two of the ring elements 210 are identified (e.g., a first ring element 210a and a second ring element 210b). The ring elements 210 lie within respective planes that are arranged in series along the longitudinal axis 20. The planes in which the ring elements 210 lie are substantially perpendicular (e.g., 90 degrees +/−10 degrees) to the longitudinal axis 20, when the tubular structure 200 is in a relaxed state. In some embodiments, a ring element 210 may be considered as lying within a plane if at least 20%, or at least 30%, or at least 40%, or at least 50%, or at least 60%, or at least 70%, or at least 80%, or at least 90% (e.g., 100%), of a circumferential length of a part of the ring element 210 lies within a plane.

The tubular structure 200 also includes connecting members 220 connected between adjacent ones of the ring elements 210. As shown in FIG. 2B, the tubular structure 200 includes multiple connecting members 220a, 220b connected between adjacent ring elements 210a, 210b. The connecting member 220a includes a first member end 232, a second member end 234 opposite from the first member end 232, and a member body 236 extending between the first member end 232 and the second member end 234. The member body 236 forms an acute angle 240 with respect to the ring element 210a. In some cases, the angle 240 may be measured with the tubular structure 200 being "un-rolled" to a flat configuration. Also, the first member end 232 of the connecting member 220a and the second member end 234 of the connecting member 220a define a line that is non-parallel to the longitudinal axis 20 of the tubular structure 200.

In the illustrated embodiments, the connecting member 220 has a rectilinear configuration. In other embodiments, at least a part of the connecting member 220 may have a curvilinear configuration.

In other embodiments, the tubular structure 200 may include more than two connecting members 220 between adjacent ring elements 210. In further embodiments, the tubular structure 200 may include only one connecting member 220 between adjacent ring elements 210.

In other embodiments, the ring elements 210 and/or connecting member 220 may have variations in length, width and thickness to adjust flexibility and kink resistance of the tubular structure 200.

In some embodiments, the member body 236 of each connecting member 220 rotates and/or bends relative to the adjacent ring element 210 as the tubular structure 200 is being axially loaded (e.g., tensioned or compressed). Accordingly, the angle 240 changes as the tubular structure 200 is being axially loaded. In addition, as the tubular structure 200 is being axially loaded to change (e.g., to increase or decrease) a spacing between adjacent ring elements 210, the cross-sectional shape of the ring elements 210 are maintained.

Also, in some embodiments, the member body 236 of each connecting member 220 rotates and/or bends relative to the adjacent ring element 210 as the tubular structure 200 is being bended. Accordingly, the angle 240 changes as the tubular structure 200 is being bended. In addition, as the tubular structure 200 is being bended, the cross-sectional shape of the ring elements 210 is maintained.

In some embodiments, filler 250 may be disposed in the spacing 216 defined between the ring elements 210 and the connecting members 220. The filler 250 provides a seal to prevent fluid from passing across a wall of the tubular structure 200. Additionally, the filler 250 behaves as a composite when integrated with the tubular structure 200 by sharing tensile and bending loads between the filler 250 and tubular structure 200, as it will be described in further detail below.

Figures 3A, 3B:
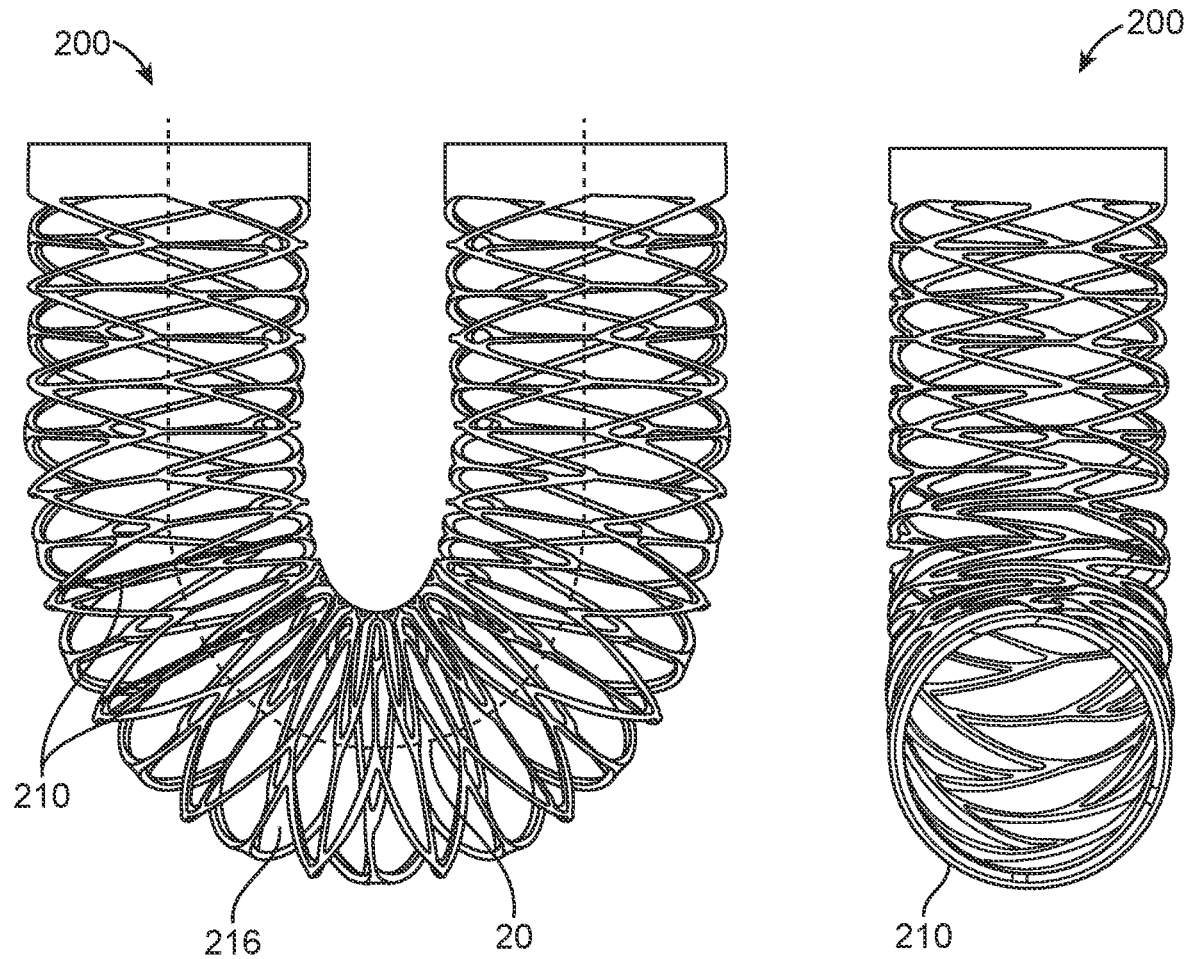
FIGS. 3A-3B illustrate a bending of the tubular structure of FIG. 2.

FIGS. 3A-3B illustrate a bending of the tubular structure 200 of FIG. 2. As shown in FIG. 3A, when the tubular structure 200 is being bent, the ring elements 210 stay substantially perpendicular (e.g., 90 degrees +/−10 degrees) to the longitudinal axis 20. The connecting members 220 are configured to move relative to the ring elements 210 in correspondence with the bending of the tubular structure 200. This allows the connecting members 220 to conform to a change in a spacing distance between adjacent ring elements 210 due to the bending of the tubular structure 200. As shown in FIG. 3B, the tubular structure 200 is advantageous because the close-loop ring elements 210 prevents the tubular structure 200 from collapsing radially inward. Thus, the cross-sectional shape of the ring elements 210 are maintained even during bending of the tubular structure 200, and kinking of the catheter 10 is prevented.

Figures 4A, 4B:
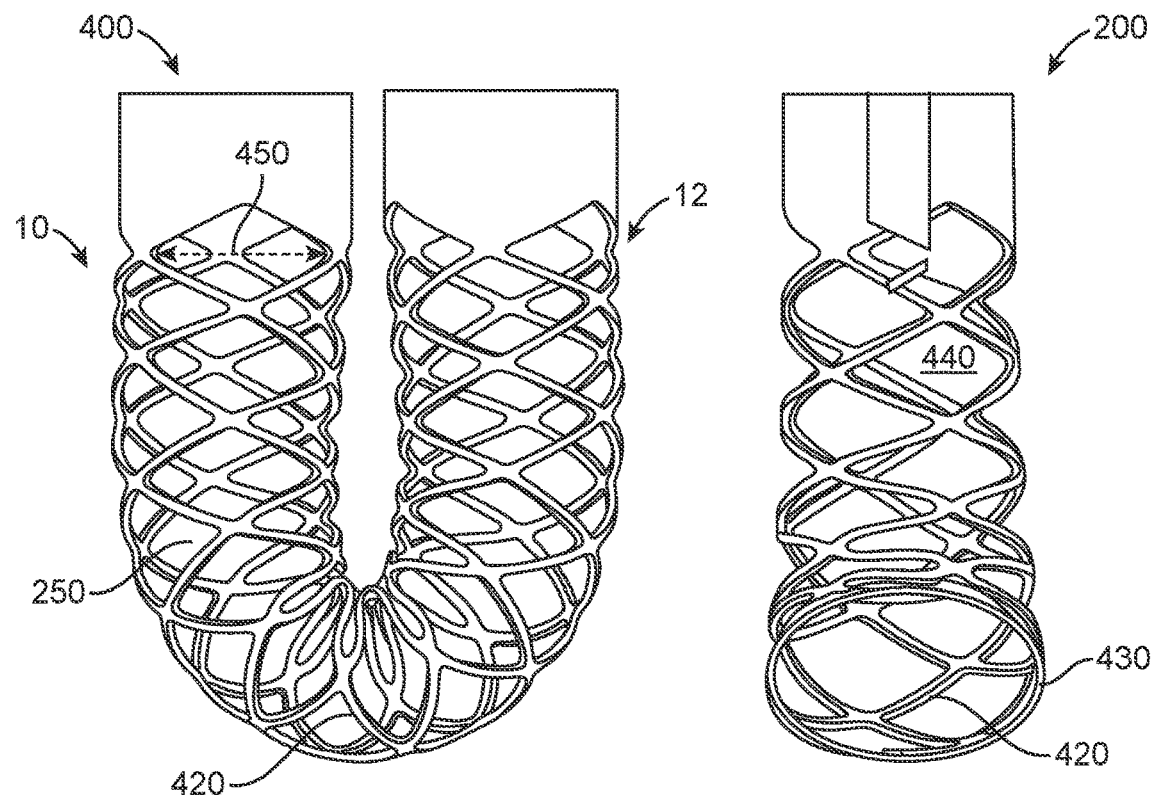
FIGS. 4A-4B illustrate a bending of another tubular structure that is different from the tubular structure of FIG. 2.

FIGS. 4A-4B illustrate a bending of another tubular structure 400 that is different from the tubular structure 200 of FIGS. 2A-2B. The tubular structure 400 comprises members 420 that are arranged in crisscross configuration. Unlike the tubular structure 200, the tubular structure 400 does not have any closed-loop ring elements that lie in respective planes. As shown in FIG. 4B, during bending of the tubular structure 400, the tubular structure 400 may be "squished" due to one side of the tubular structure 400 being in compression from the bending. As a result, if the tubular structure 400 defines a circular cross-section lumen while in a relaxed state, the "squished" tubular structure 400 may result in the lumen having an elliptical shape 430. A catheter constructed using the tubular structure 400 will be easily kinked during use.

Although the "squished" tubular structure 400 of FIG. 4B may result in the lumen having an elliptical shape 430, the members 420 arranged in crisscross configuration form relative large diamond cells 440 (e.g., range from 1 to 4 mm of cell width 450) that are configured to distribute the load on the catheter 10 while preventing tearing of the filler 250 during bending. Without the relative large diamond cells 440, attempts to shape the distal end 12 would tear the filler 250 damaging the catheter 10. By preventing the filler 250 from tearing, the overall kink radius of the tube 11 is smaller (e.g., 0.2 mm), enabling the distal end 12 to be formed into a desired shape (i.e., pre-shape), to have shape retention, and to improve trackability. Additionally, the relative large diamond cells 440 of the tubular structure 400 are configured to increase flexibility of the distal end 12 of the catheter 10 forming a flexible end tip (e.g., ultra-soft tip), allowing bending and deflecting the catheter 10 in tortuous body lumens.

In other embodiments, instead of having the acute angle 240 shown in the above example of FIGS. 2A-2B, the member bodies 236 of the connecting members 220 and their respective adjacent ring elements 210 of the tubular structure 200 may form other non-zero acute angles when the tubular structure 200 is in a relaxed state. Also, in other embodiments, the member bodies 236 of the connecting members 220 may be parallel with their respective adjacent ring elements 210.

Figure 5:
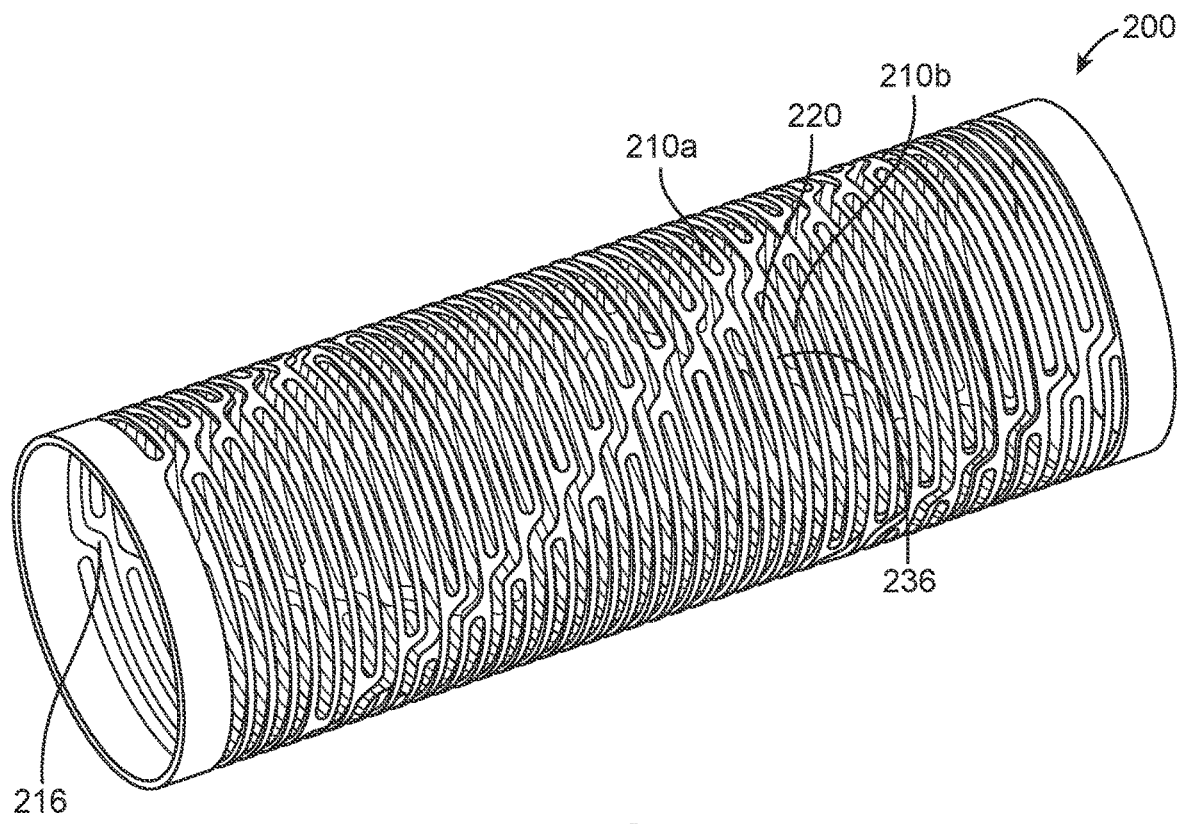
FIG. 5 illustrates another tubular structure.

FIG. 5 illustrates another tubular structure 200. The tubular structure 200 is similar to that of FIGS. 2A-2B, except that a majority of the body 236 of each connecting member 220 is parallel to an adjacent ring element 210 when the tubular structure 200 is in a relaxed state. In particular, a majority of each connecting member 220 lies in a plane that is parallel to the plane in which an adjacent ring element 210 lies when the tubular structure 200 is in a relaxed state.

The tubular structure 200 of FIG. 5 may be considered as a variation of the tubular structure 200 of FIGS. 2A-2B.

Figure 6:
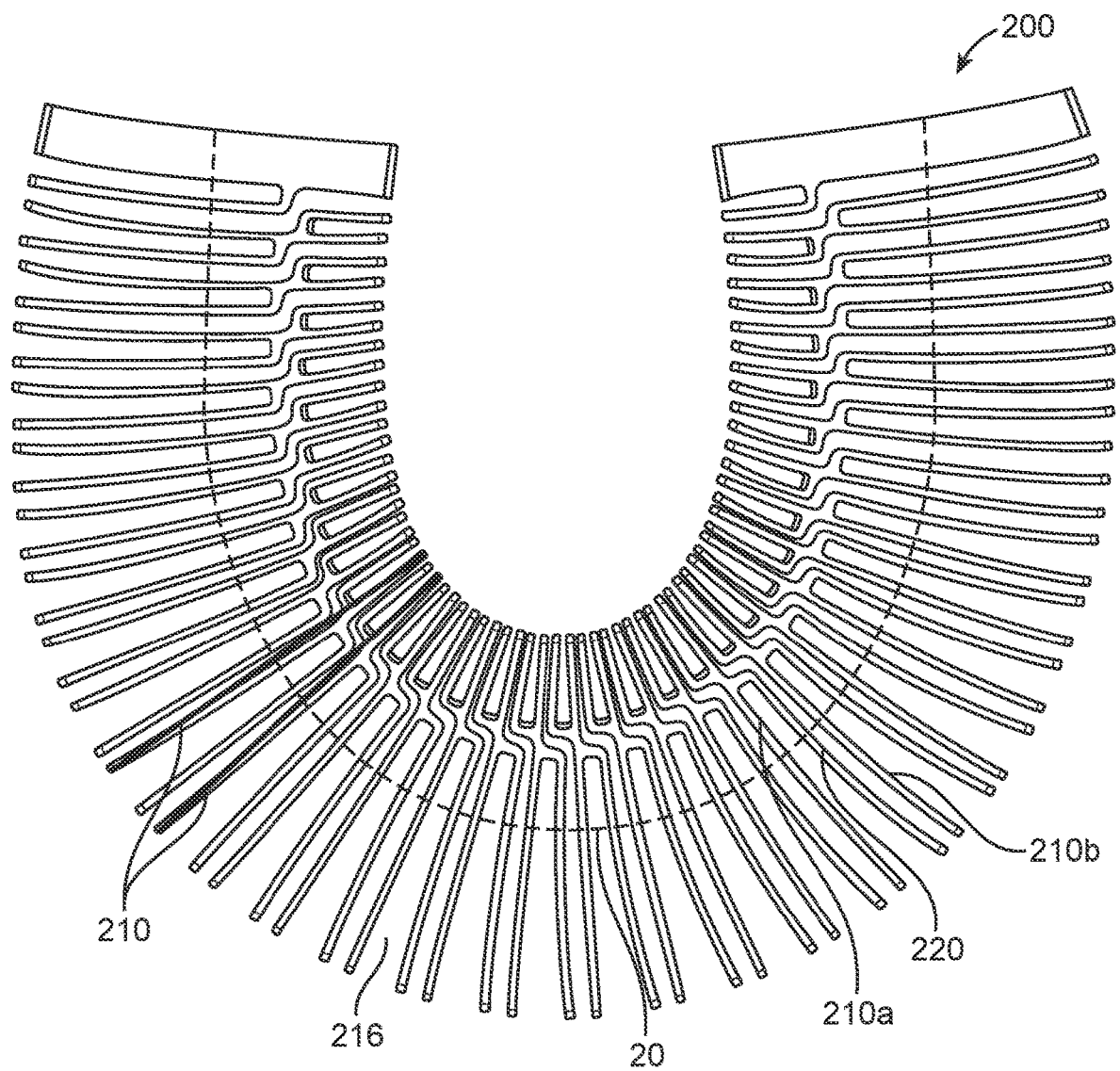
FIG. 6 illustrates a bending of the tubular structure of FIG. 5.

FIG. 6 illustrates a bending of the tubular structure 200 of FIG. 5. As shown in FIG. 6, when the tubular structure 200 is being bent, the ring elements 210 stay substantially perpendicular (e.g., 90 degrees +/−10 degrees) to the longitudinal axis 20. The connecting members 220 are configured to move (e.g., flex and/or rotate) relative to the ring elements 210 in correspondence with the bending of the tubular structure 200. This allows the connecting members 220 to conform to a change in a spacing distance between adjacent ring elements 210 due to the bending of the tubular structure 200. As similarly discussed, the tubular structure 200 is advantageous because the closed-loop ring elements 210 prevent the tubular structure 200 from collapsing radially inward. Thus, the cross-sectional shape of the ring elements 210 are maintained even during bending of the tubular structure 200, and kinking of the catheter 10 is prevented.

Figure 7:
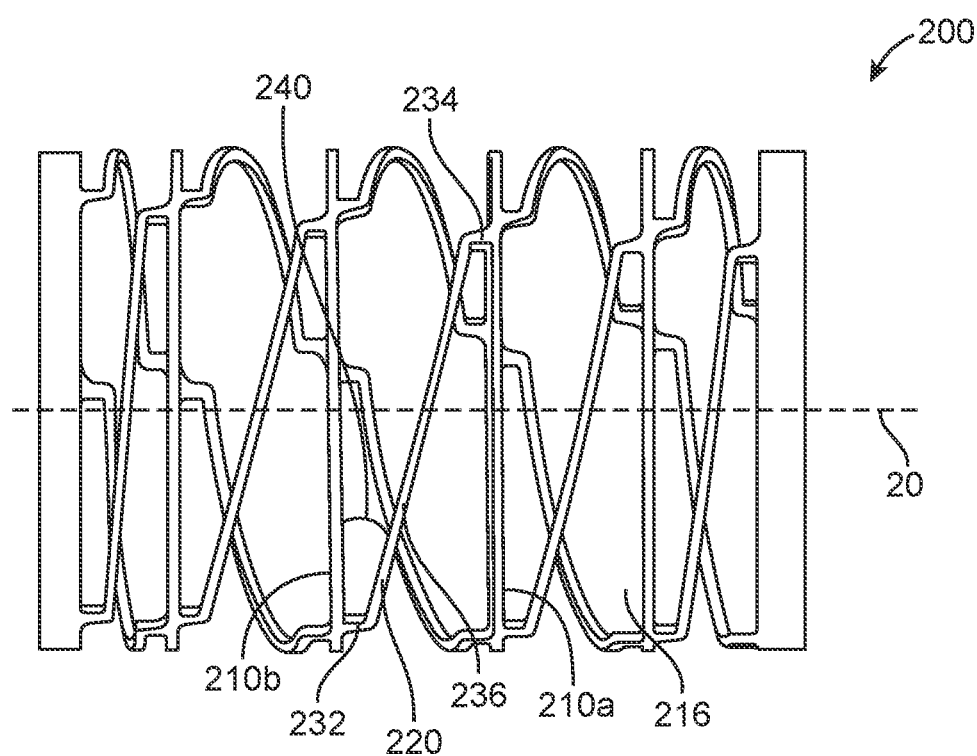
FIG. 7 illustrates a tensioning of the tubular structure of FIG. 5.

FIG. 7 illustrates a tensioning of the tubular structure 200 of FIG. 5. As the tubular structure 200 is being tensioned, the planes in which the respective ring elements 210 (e.g., ring elements 210a, 210b) lie remain substantially perpendicular (e.g., 90 degrees+/−10 degrees) to the longitudinal axis 20. The connecting members 220 between adjacent pairs of the ring elements 210 elastically flex in correspondence with axial movement of the ring elements 210 as the tubular structure 200 is being tensioned. As shown in the figure, the member body 236 of each connecting member 220 rotates and/or bends relative to the adjacent ring element 210 so that the angle 240 changes as the tubular structure 200 is being tensioned. In addition, as the tubular structure 200 is being tensioned to change a spacing between adjacent ring elements 210, the cross-sectional shape of the ring elements 210 are maintained.

Figure 8:
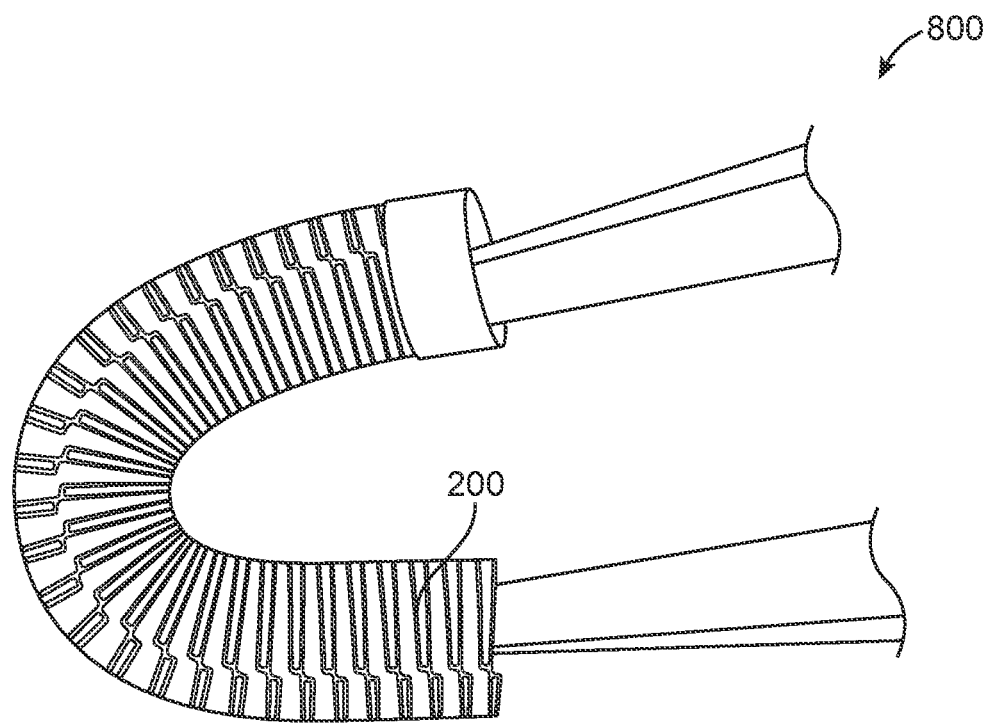
FIG. 8 illustrates a tube segment having the tubular structure of FIG. 5, particularly showing the tube segment being bent.

FIG. 8 illustrates a tube segment 800 having the tubular structure 200 of FIG. 5, particularly showing the tube segment 800 being bent. The tube segment 800 may be a part of the catheter 10 of FIG. 1 in some embodiments. As shown in FIG. 8, the tube segment 800 with the tubular structure 200 can undergo very tight bending to have a bent shape with small radius of curvature. Through the entire length of the bend, the gaps between respective pairs of adjacent ring elements 210 remain substantially even (e.g., the gaps between different pairs of adjacent ring elements 210 do not vary by more than 10%). This is the case for both the gaps on the tension side, and the gaps on the compression side, of the bent tube segment 800.

Figure 9:
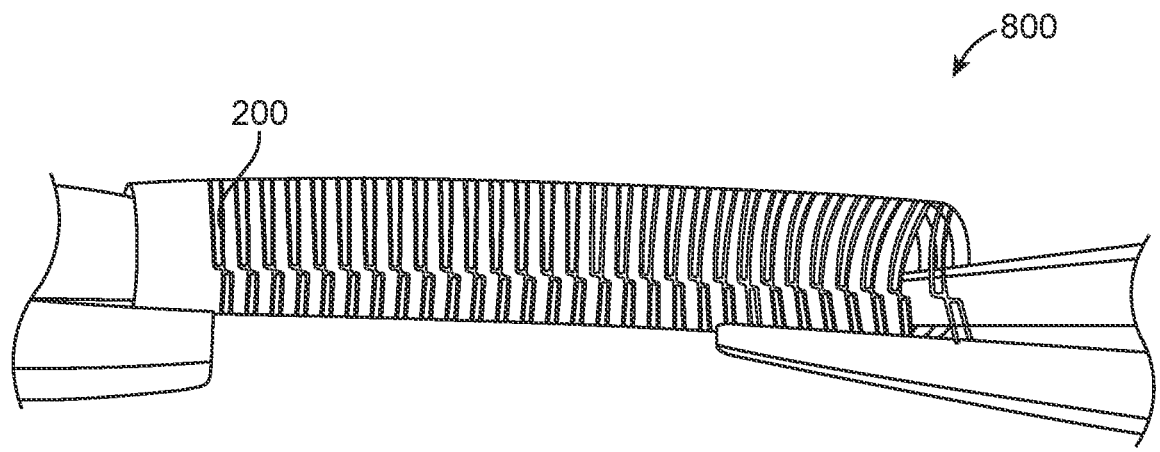
FIG. 9 illustrates the tube segment of FIG. 8, particularly showing the tube segment being tensioned.

FIG. 9 illustrates the tube segment 800 of FIG. 8, particularly showing the tube segment 800 being tensioned. While the tube segment 800 is being tensioned, the gaps between respective pairs of adjacent ring elements 210 remain substantially even (e.g., the gaps between different pairs of adjacent ring elements 210 do not vary by more than 10%).

Figure 10:
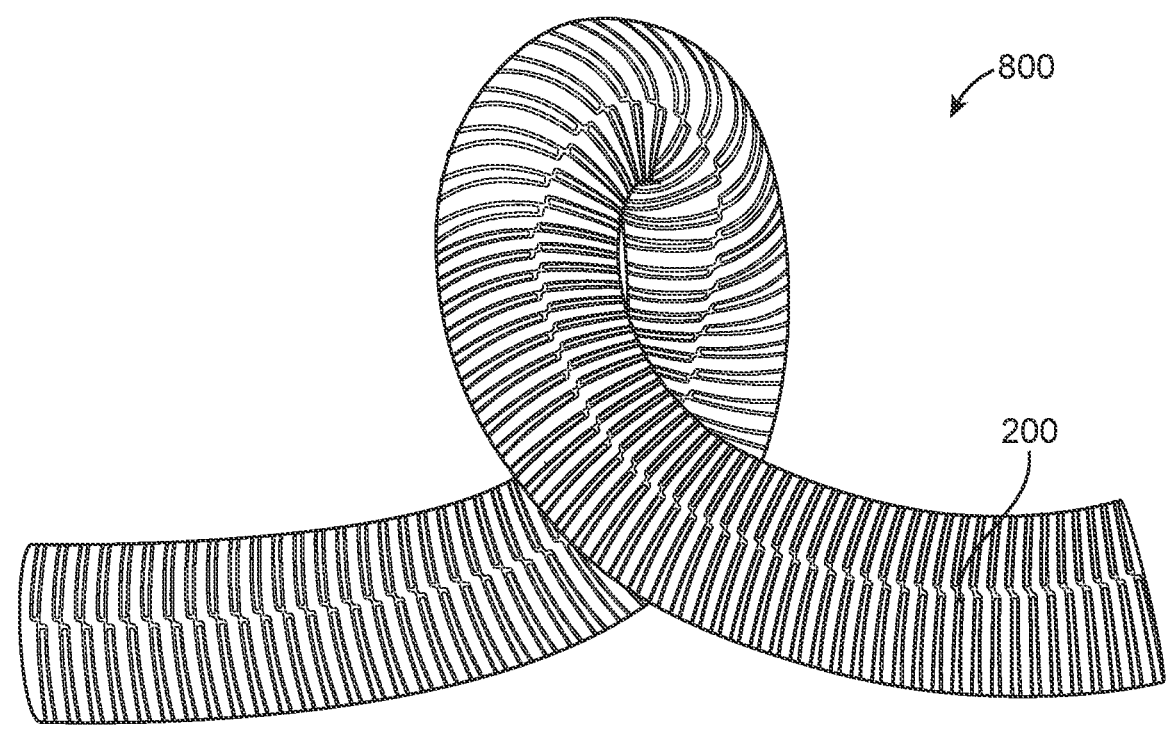
FIG. 10 illustrates the tube segment of FIG. 8, particularly showing the tube segment being tested for kink resistance.

FIG. 10 illustrates the tube segment 800 of FIG. 8, particularly showing the tube segment 800 being tested for kink resistance. As shown in FIG. 10, the tube segment 800 with the tubular structure 200 can undergo 360-degree bending to have a bent shape with small radius of curvature. Through the entire length of the bent, the gaps between respective pairs of adjacent ring elements 210 remain substantially even (e.g., the gaps between different pairs of adjacent ring elements 210 do not vary by more than 10%). This is the case for both the gaps on the tension side, and the gaps on the compression side, of the bent tube segment 800. As shown in the figure, even with such extreme bending, the tube segment 800 forms no kink, and the structural integrity of the tube segment 800 is maintained.

In the above embodiments, the tubular structure 200 is illustrated as having ring elements 210, wherein each ring element 210 has an uniform cross-section along the circumferential length of the ring element 210. In other embodiments, a ring element 210 may have a varying cross-section along the circumferential length of the ring element 210.

Figure 11:
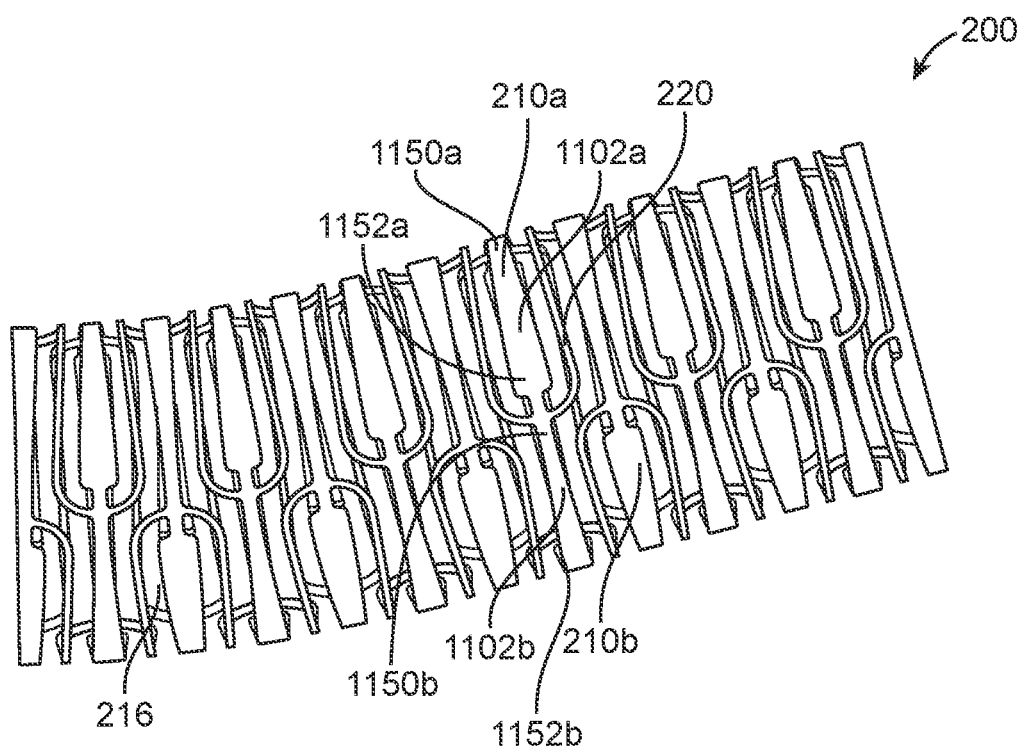
FIG. 11 illustrates another tubular structure.

FIG. 11 illustrates another tubular structure 200. The tubular structure 200 is similar to that of FIG. 5, except that each ring element 210 has a varying cross-section along the circumferential length of the ring element 210. Also, the connecting members 220 have a much smaller cross-sectional dimension compared to that of the ring elements 210. In some embodiments, the connecting member 220 may have a cross-sectional dimension that is less than 50%, or less than 40%, or less than 30%, or less than 20% or less than 10%, of a cross-sectional dimension (e.g., the largest cross-sectional dimension, the smallest cross-sectional dimension, or the average cross-sectional dimension) of the ring element 210. The tubular structure 200 of FIG. 11 may be considered as a variation of the tubular structure 200 of FIG. 5 or FIGS. 2A-2B.

The configuration of the tubular structure 200 of FIG. 11 is advantageous because it provides increased spacing (compared to the tubular structure 200 of FIG. 5) between the ring elements 210 and the connecting members 220. This allows more filler material to be disposed between the ring elements 210 and the connecting members 220. By configuring an amount of filler material that is placed between the ring elements 210 and the connecting members 220, a stiffness and/or a degree of maximum bending (for a medical device incorporating the tubular structure 200) can be tailored. For example, if it is desirable to make the catheter 10 more flexible so that it can be bent more, the spacing between the ring elements 210 and the connecting members 220 can be increased. On the other hand, if it is desirable to make the catheter 10 less flexible so that it cannot bend as much, the spacing between the ring elements 210 and the connecting members 220 can be decreased.

As shown in FIG. 11, two of the ring elements 210 are being identified (i.e., ring element 210a, and ring element 210b). The ring element 210a includes different cross-sectional dimensions along a length of the ring element 210a. In particular, the ring element 210a has multiple ring segments 1102 (e.g., first ring segment 1102a, second ring segment 1102b) connected together, each of the multiple ring segments 1102 having a paddle-shape. In the illustrated embodiments, the first ring segment 1102a of the ring element 210a has a first end 1150a and a second end 1152a opposite from the first end 1150a, wherein the second end 1152a is larger in cross-section compared to the first end 1150a. Similarly, the second ring segment 1102b has a first end 1150b and a second end 1152b opposite from the first end 1150b, wherein the second end 1152b is larger in cross-section compared to the first end 1150b. The first end 1150b of the second ring segment 1102b is connected to the second end 1152a of the first ring segment 1102a. The connecting member 220 extends from the first end 1150b of the second ring segment 1102b.

In other embodiments, the segments 1102 may have other shapes (e.g., non-rectangular shape). Also, in other embodiments, instead of the segments 1102 of each ring element 210 having the same shape, the segments 1102 of each ring element 210 may have different respective shapes.

Figure 12:
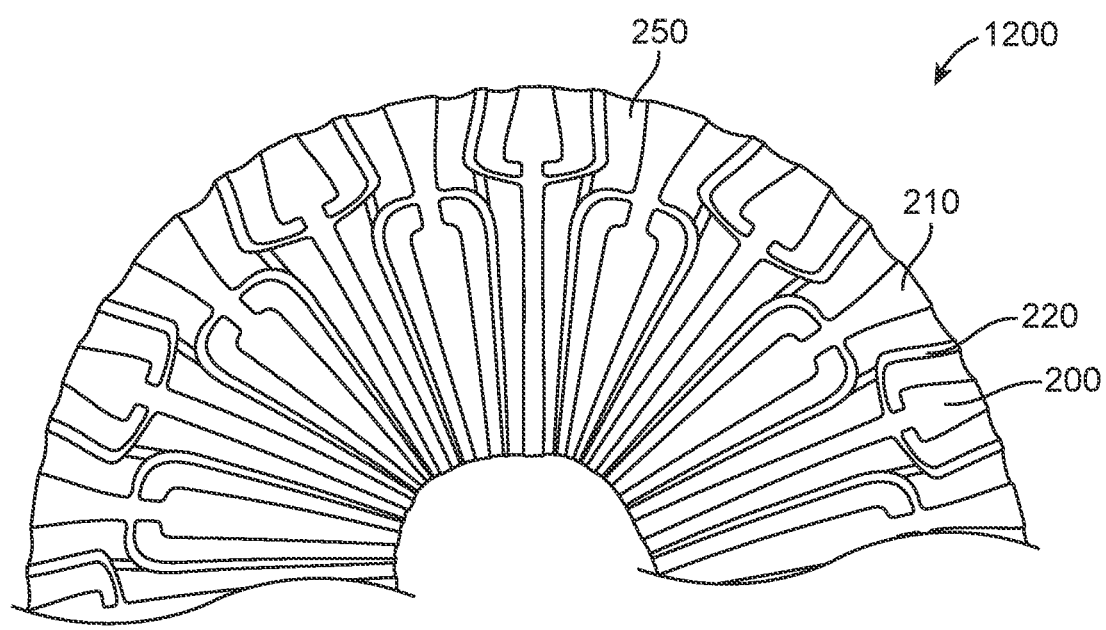
FIG. 12 illustrates a tube segment having the tubular structure of FIG. 11.

FIG. 12 illustrates a tube segment 1200 having the tubular structure of FIG. 11, particularly showing the tube segment 1200 being bent. The tube segment 1200 also includes filler 250 disposed in the space that is between the ring elements 210 and the connecting members 220. The tube segment 1200 may be a part of the catheter 10 of FIG. 1 in some embodiments. As shown in FIG. 12, the tube segment 1200 with the tubular structure 200 can undergo very tight bending to have a bent shape with small radius of curvature. Through the entire length of the bent, the spacing between pairs of adjacent ring elements 210 remain substantially even (e.g., the gaps between different pairs of adjacent ring elements 210 do not vary by more than 10%). This is the case for both the gaps on the tension side, and the gaps on the compression side, of the bent tube segment 800.

Increasing the width of the ring element 210 (e.g., at certain part(s) of the ring element 210) is advantageous. This is because polymers have stretch limit, which can limit the bend radius of a tube formed using polymers. This effect is useful since limiting the bend radius can result in more support for pushing the tube. By increasing the width of the ring elements 210, the amount of space available for the filler 250 becomes reduced, which in turn changes the distance the polymer can stretch within the space 216. Accordingly, the tube behavior (e.g., bending stiffness, bending limit, torsional stiffness, torsional strain limit, axial stiffness, axial strain limit, etc., or any combination of the foregoing) may be selectively adjusted without the added complexity of changing polymer formulation (chemistry). This is especially beneficial to medical devices where each material change requires an enormous amount of paperwork, testing, validation, etc.

Figure 13:
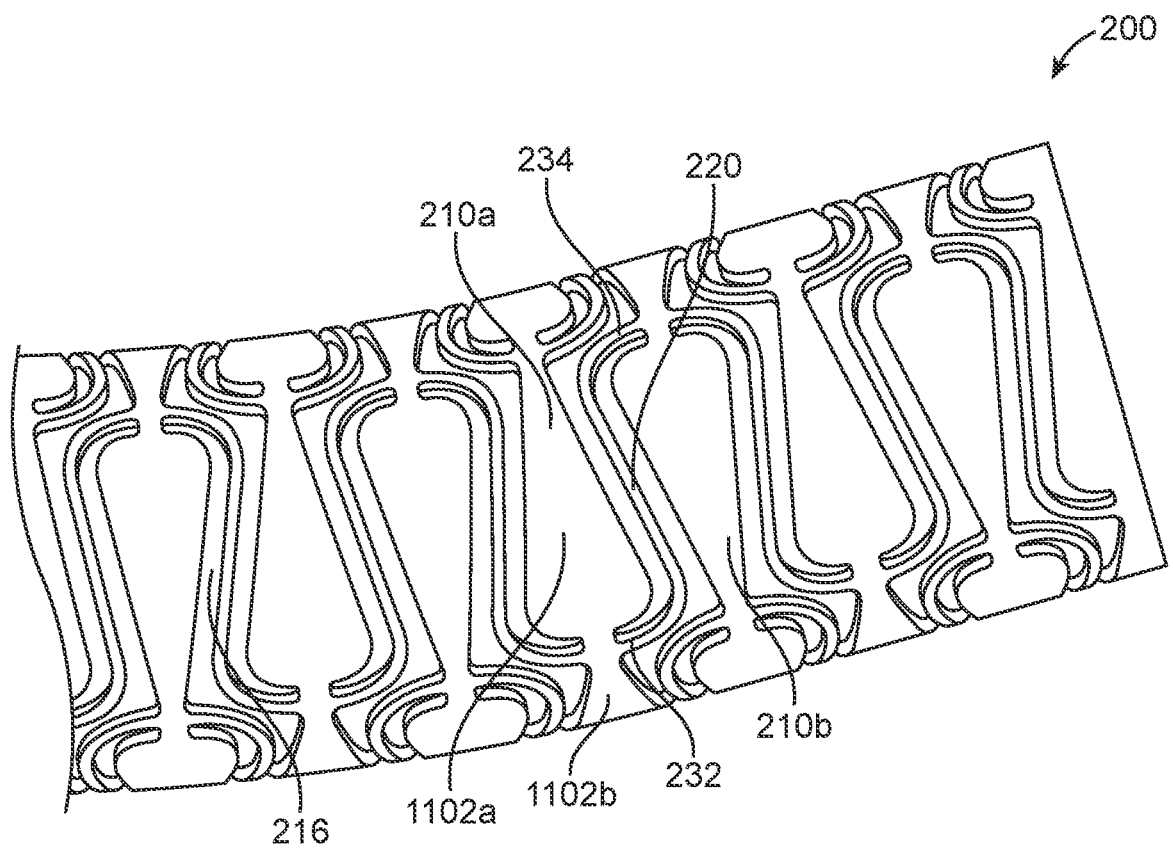
FIG. 13 illustrates another tubular structure.

FIG. 13 illustrates another tubular structure 200. The tubular structure 200 is the same as that shown in FIG. 11, except that the tubular structure 200 of FIG. 13 has ring elements 210 (e.g., ring elements 210a, 210b) that are wider. The wider ring elements 210 occupy more space, thereby reducing an amount of space that is between the ring elements 210 and the connecting members 220. As a result, less filler 250 will be disposed in the space 216 that is between the ring elements 210 and the connecting members 220 (compared to thinner ring elements 210 having the same center-to-center distance), and the resulting tube formed by such tubular structure 200 will be stiffer compared to that of FIG. 11.

Figure 14:
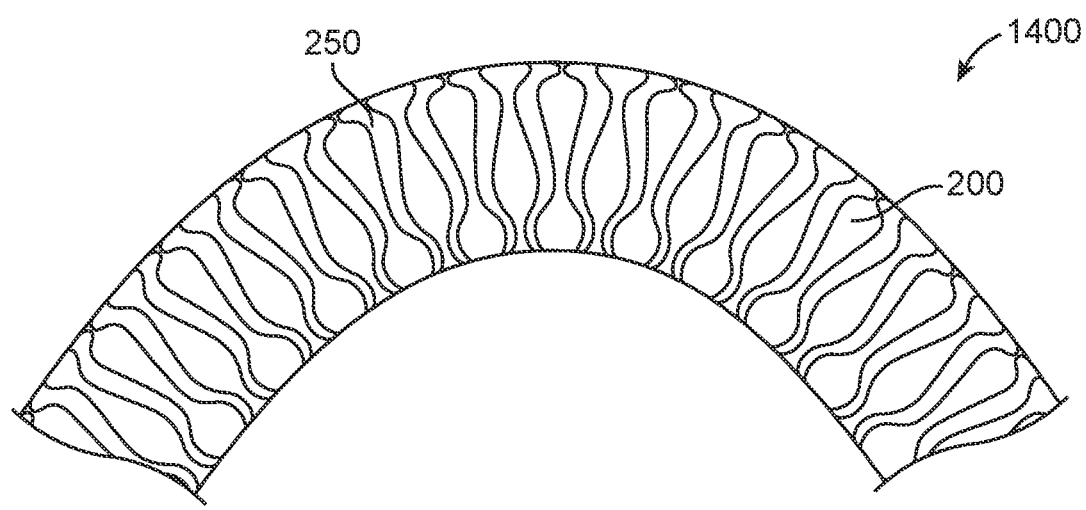
FIG. 14 illustrates a tube segment having the tubular structure of FIG. 13.

FIG. 14 illustrates a tube segment 1400 having the tubular structure 200 of FIG. 13, particularly showing the tube segment 1400 being bent. The tube segment 1400 also includes filler disposed in the space that is between the ring elements 210 and the connecting members 220. The tube segment 1400 may be a part of the catheter 10 of FIG. 1 in some embodiments. As shown in FIG. 14, the tube segment 1400 with the tubular structure 200 can undergo very tight bending to have a bent shape with small radius of curvature. Through the entire length of the bent, the spacing between pairs of adjacent ring elements 210 remain substantially even (e.g., the gaps between different pairs of adjacent ring elements 210 do not vary by more than 10%). This is the case for both the gaps on the tension side, and the gaps on the compression side, of the bent tube segment 800. The tube segment 1400 of FIG. 14 is stiffer, and can undergo less bending, compared to the tube segment 1200 of FIG. 12 because the tube segment 1400 has less amount of filler 250 between the ring elements 210 and the connecting members 220.

Figure 15:
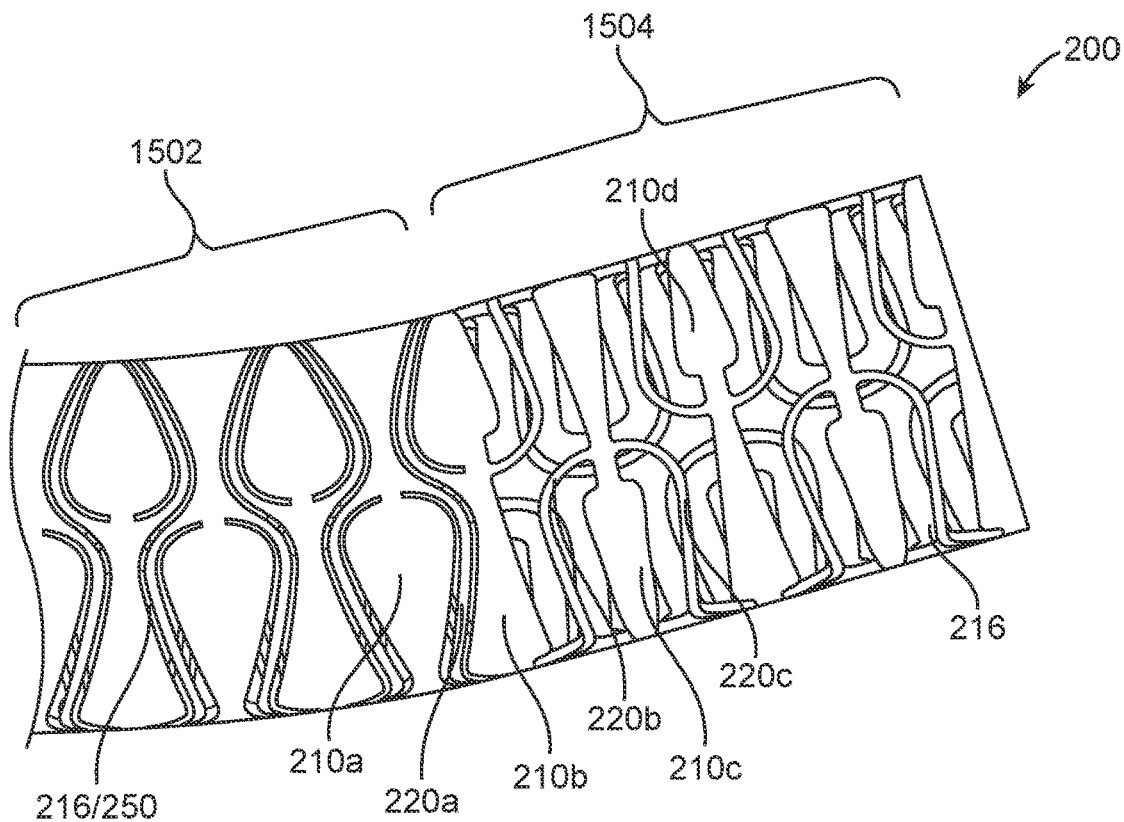
FIG. 15 illustrates another tubular structure.

FIG. 15 illustrates another tubular structure 200. The tubular structure 200 has a first section 1502 and a second section 1504. The first section 1502 and the second section 1504 have different respective stiffness. In the illustrated embodiments, the first section 1502 has a pattern that is similar to the embodiments of FIG. 13, except that the spacing between the ring elements 210 and the adjacent connecting elements 220 is smaller. The second section 1504 has the same pattern as that of the embodiments of FIG. 11. As shown in FIG. 15, the spacing between the connecting member 220a and its adjacent ring elements 210a, 210b in the first section 1502 is less than the spacing between the connecting member 220c and its adjacent ring elements 210c, 210d in the second section 1504. Such configuration allows more filler 250 be placed in the space 216 among the ring elements 210 and connecting members 220 in the second section 1504 than in the space 216 among the ring elements 210 and connecting members 220 in the first section 1502. Since the filler 250 contributes the flexibility of the medical device, the second section 1504 with more filler 250 will be more flexible (having lower stiffness) than the first section 1504.

Figure 16:
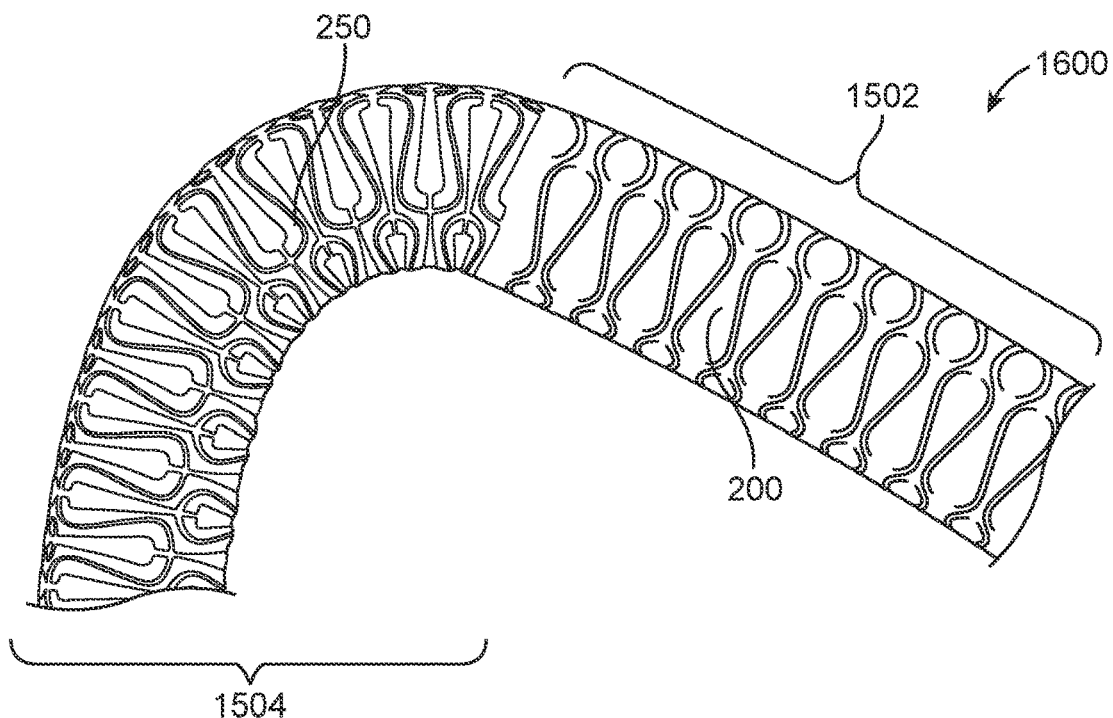
FIG. 16 illustrates a tube segment having the tubular structure of FIG. 15.

In the illustrated embodiments, the first section 1502 has a first bending stiffness, and the second section 1504 has a second bending stiffness, wherein the first bending stiffness is higher than the second bending stiffness. FIG. 16 illustrates a tube segment 1600 having the tubular structure of FIG. 15, and filler 250 disposed among the ring elements 210 and the connecting members 220. As shown in the figure, the section of the tube segment 1600 with the second section 1504 of the tubular structure 200 is more flexible, allowing the tube segment 1600 to undergo more bending, compared to the section of the tube segment 1600 with the first section 1502.

In some embodiments, the first section 1502 of the tubular structure 200 has a first axial stiffness, and the second section 1504 has a second axial stiffness, wherein the first axial stiffness is higher than the second axial stiffness.

Also, in some embodiments, the first section 1502 of the tubular structure 200 has a first torsional stiffness, and the second section 1504 has a second torsional stiffness, wherein the first torsional stiffness is higher than the second torsional stiffness.

In some embodiments, the transition between the first section 1502 and the second section 1504, may be a gradual transition by adjusting the pattern of the tubular structure 200 and/or the size of the spacing between the connecting members 220. A gradual transition between the first section 1502 and the second section 1504 of the tubular structure 200 is configured to have a higher tracking performance of the catheter 10.

Figure 17:
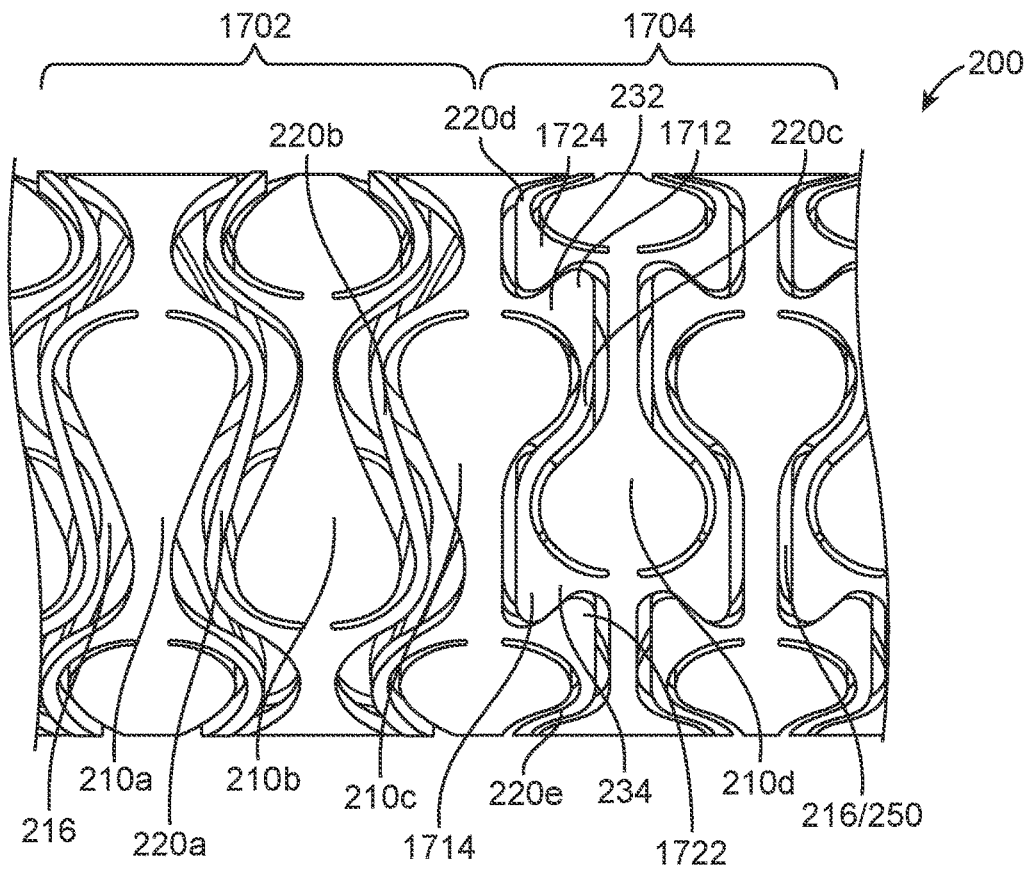
FIG. 17 illustrates another tubular structure.

FIG. 17 illustrates another tubular structure 200. The tubular structure 200 has a first section 1702 and a second section 1704. The first section 1702 and the second section 1704 are the same (and they have patterns that are similar to the embodiments of FIG. 13), except that the second section 1704 has interlocks (e.g., interlocks 1712, 1714, 1722, 1724). The interlocks are configured to keep at least some of the adjacent ring elements 210 from moving too far away from each other during axial loading (e.g., tensioning and/or compression), and/or bending of the tubular structure 200.

As shown in FIG. 17, the first section 1702 of the tubular structure 200 includes ring element 210a and adjacent ring element 210b. The first section 1702 of the tubular structure 200 also includes connecting member 220a connected between the ring element 210a and the ring element 210b. The second section 1704 of the tubular structure 200 includes ring element 210c and adjacent ring element 210d. The second section 1704 of the tubular structure 200 also includes connecting member 220c connected between the ring element 210c and the ring element 210d. The tubular structure 200 also includes connecting member 220b connected between the ring element 210b and the ring element 210c.

The second section 1704 of the tubular structure 200 includes interlocks 1714, 1722 in abutment engagement with each other, and also interlocks 1712, 1724 in abutment engagement with each other. The interlock 1712 is implemented at the first end 232 of the connecting member 220c, and the interlock 1714 is implemented at the second end 234 of the connecting member 220c. The interlock 1712 at the end 232 of the connecting member 220c that is connected to (or extend from) the ring element 210c is configured to engage with another interlock 1724 at an end of connecting member 220d. Similarly, the interlock 1714 at the end 234 of the connecting member 220c that is connected to (or extend from) the ring element 210d is configured to engage with another interlock 1722 at an end of connecting member 220e. In the illustrated embodiments, the connecting members 220c, 220d, 220e are connected between adjacent ring elements 210c, 210d, and are arranged in a same row. Thus, connecting members 220 in the same row between adjacent ring elements 210 are all connected to the same ring element 210 (e.g., ring element 210c) at first respective ends 232 of the connecting members 220, and are all connected to the same adjacent ring element 210 (e.g., ring element 210d) at second respective ends of the connecting members 220. Also, each of the first ends 232 of the connecting members 220 in the same row are in engagement with the second end 234 of the connecting member 220 next in the series along the circumference in the same row.

Figure 18:
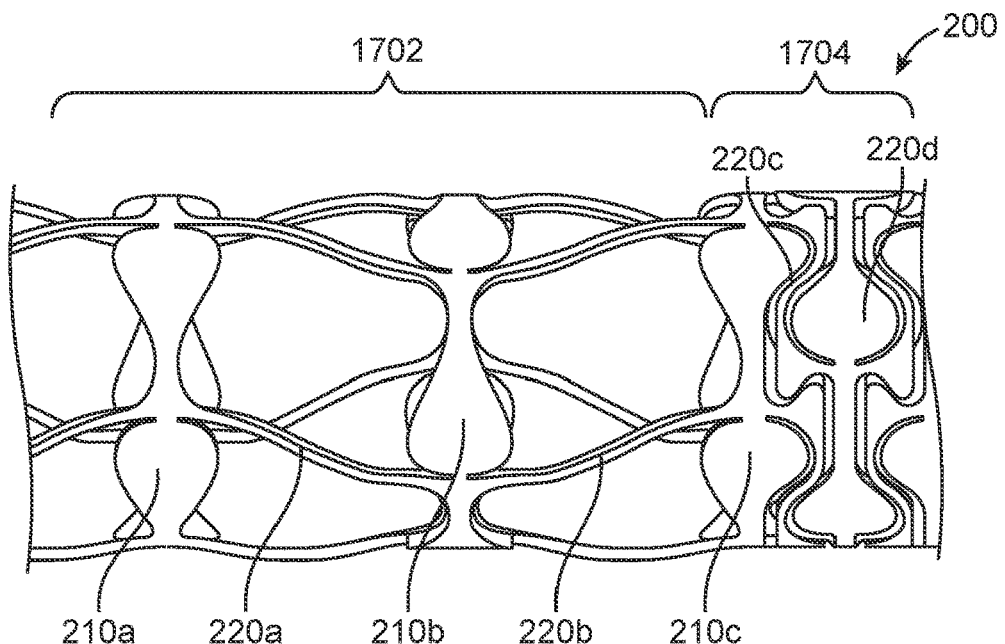
FIG. 18 illustrates a tensioning of the tubular structure of FIG. 17.

FIG. 18 illustrates a tensioning of the tubular structure 200 of FIG. 17. As shown in the figure, because the first section 1702 of the tubular structure 200 has no interlocks, the first section 1702 can deform more in response to axial loading (e.g., tensioning). Without any interlocks locking adjacent ring elements 210a, 210b with respect to each other, the ring elements 210a, 210b in the first section 1702 can move relative to each other (at least more so compared to the second section 1704) when the tubular structure 200 is being tensioned. On the other hand, the interlocks in the second section 1704 maintain the ring elements 210c, 210d in close proximity relative to each other, and prevent the ring elements 210c, 210d from moving too far from each other (e.g., within a certain distance threshold) when the tubular structure 200 is being tensioned.

Figure 19:
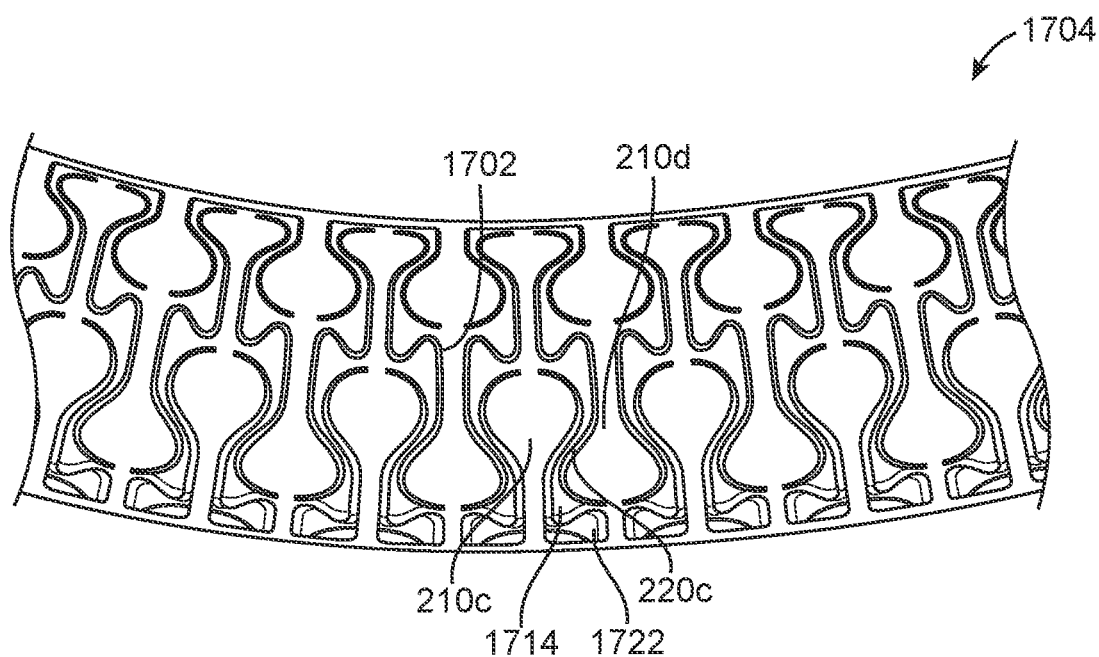
FIG. 19 illustrates a section of the tubular structure of FIG. 17, particularly showing the section undergoing bending.

In some embodiments, the interlocks can also prevent the adjacent ring elements 210c, 210d in close proximity relative to each other, and prevent the ring elements 210c, 210d from moving too far from each other (within a certain distance threshold) when the tubular structure 200 is being bent. FIG. 19 illustrates the second section 1704 of the tubular structure 200 of FIG. 17, particular showing the second section 1704 undergoing bending. As shown in the figure, the interlocks (e.g., interlocks 1714, 1722) are in abutment engagement with each other as the section 1704 of the tubular structure 200 is being bent. This prevents the ring elements 210 (e.g., ring elements 210c, 210d) from moving too far away (e.g., past a certain distance threshold) from each other during bending of the section 1704.

Figure 20:
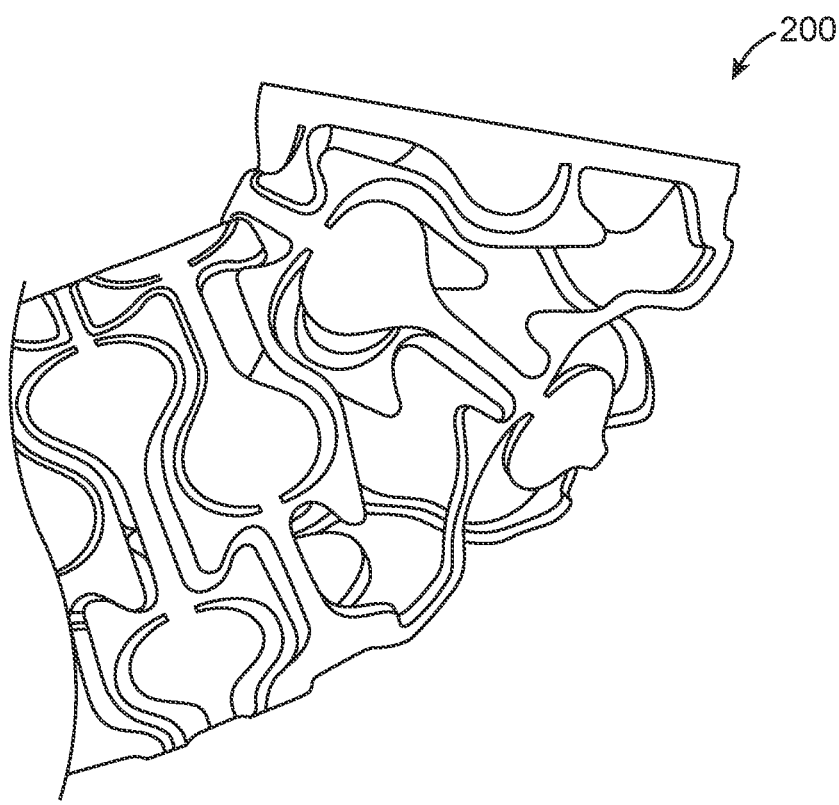
FIG. 20 illustrates the tubular structure of FIG. 17, particularly showing some of the interlocks being disengaged during bending of the tubular structure.

In the embodiments of FIG. 17, each pair of interlocks has respective curvilinear sides at the interlocks that allow them to rotate relative to each other as the connecting members 220 rotate relative to the adjacent ring elements 210. Also, the interface between the pair of interlocks is oriented at a certain angle A so that the interlocks will uncouple and slide off from each other if the relative rotation between the interlocks exceeds a certain limit. The relative rotation between the interlocks may be due to axial-loading and/or bending of the tubular structure 200, which causes the connecting members 220 (with the interlocks at opposite ends of the connecting members 220) to flex and/or rotate. In the illustrated embodiments, the angle A is about 45 degrees (e.g., 45+/−5 degrees). In other embodiments, the angle A may have other values. FIG. 20 illustrates the second section 1704 of the tubular structure 200 of FIG. 17, particularly showing some of the interlocks being disengaged during bending of the tubular structure 200.

Figure 21A:
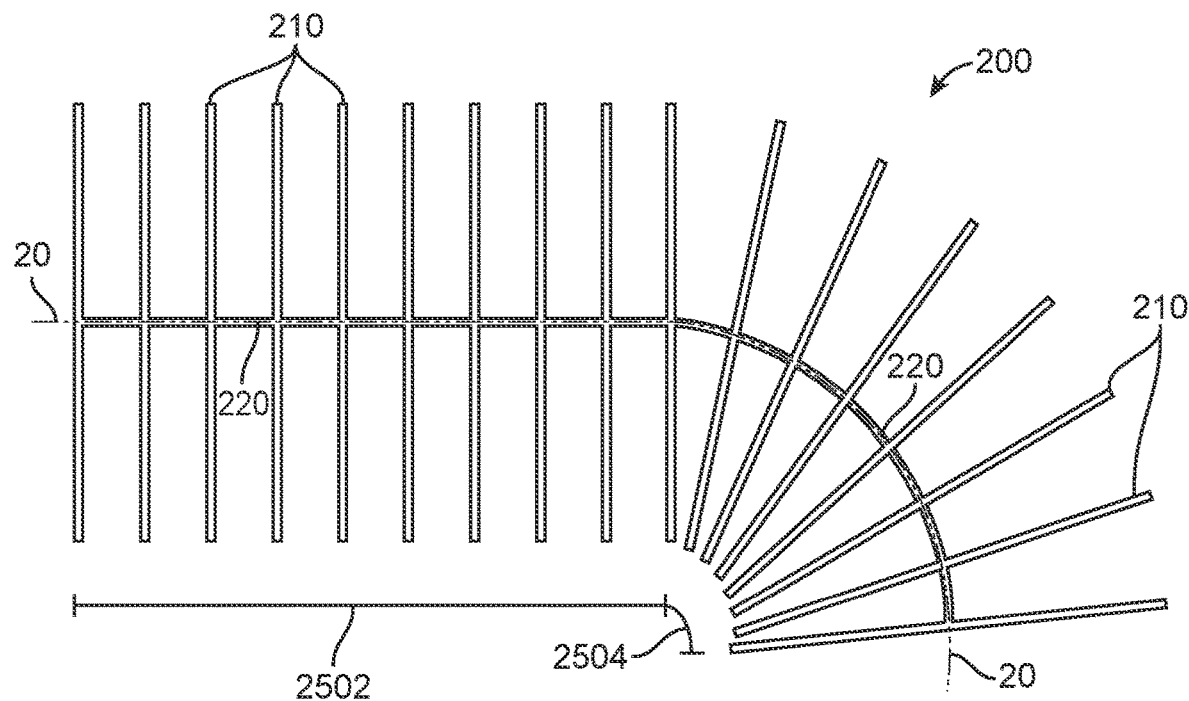
FIGS. 21A-21B illustrate a side and perspective view of another tubular structure.
Figure 21B:
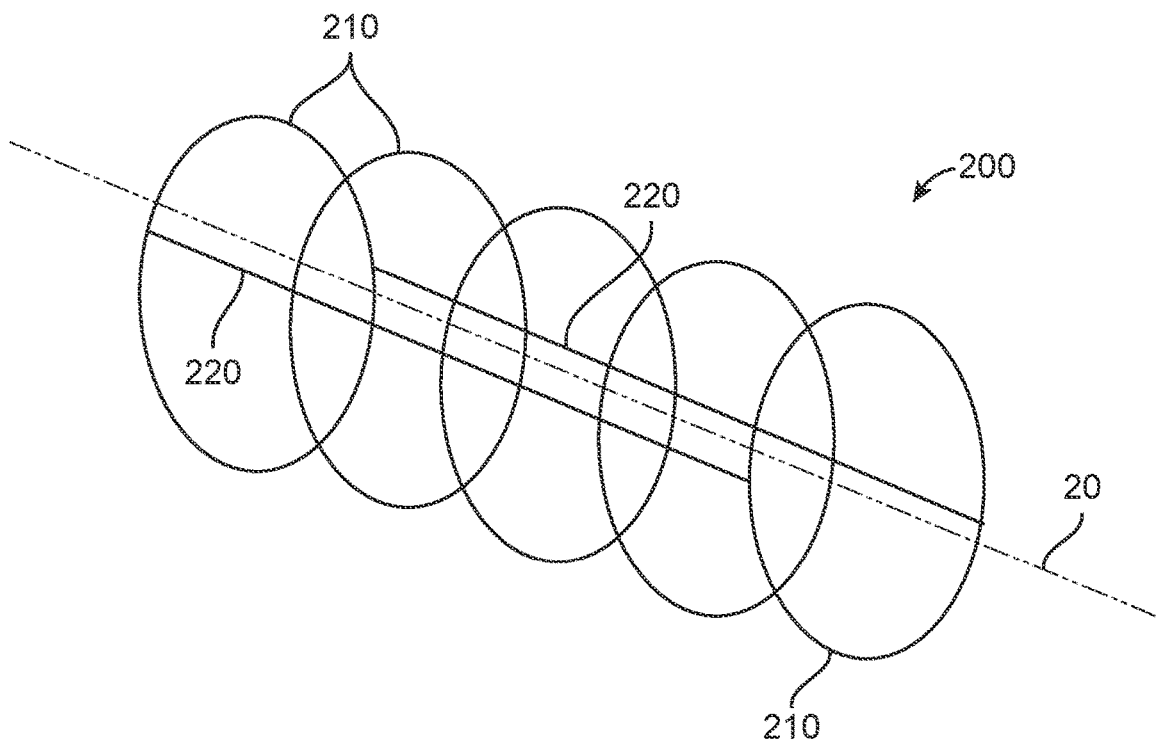

FIGS. 21A-21B illustrates yet another tubular structure 200. The tubular structure 200 has a plurality of ring elements 210 arranged in series along the longitudinal axis 20. The ring elements 210 lie within respective planes, substantially parallel to each adjacent ring element 210 when the tubular structure 200 is in a relaxed state. Further, the planes in which the ring elements 210 lie are substantially perpendicular (e.g., 90 degrees+/−10 degrees) to the longitudinal axis 20, when the tubular structure 200 is in a relaxed state. In the illustrated embodiments, the ring elements 210 are respective closed-loops; better appreciated in FIG. 21B, which illustrates a perspective view of a portion of the tubular structure 200.

The tubular structure 200 of FIGS. 21A-21B may be considered as a variation of the tubular structure 200 of FIGS. 2A-2B. The tubular structure 200 of FIGS. 21A-21B are similar to that of FIGS. 2A-2B, except that the connecting members 220 are substantially perpendicular between adjacent ring elements 210 and/or substantially parallel to the longitudinal axis 20, when the tubular structure 200 is in a relaxed state, as shown in section 2502.

In the embodiments of FIGS. 21A-21B, the tubular structure 200 includes a pair of connecting members 220 between adjacent ring elements 210. The pair of connecting members 220 have a rectilinear configuration and are disposed substantially at π distance (e.g. 0 and 180 degrees) of a respective ring element 210 of the tubular structure 200, as shown in FIG. 21B. In further embodiments, the tubular structure 200 may include only one connecting member 220 between adjacent ring elements 210.

Figure 22:
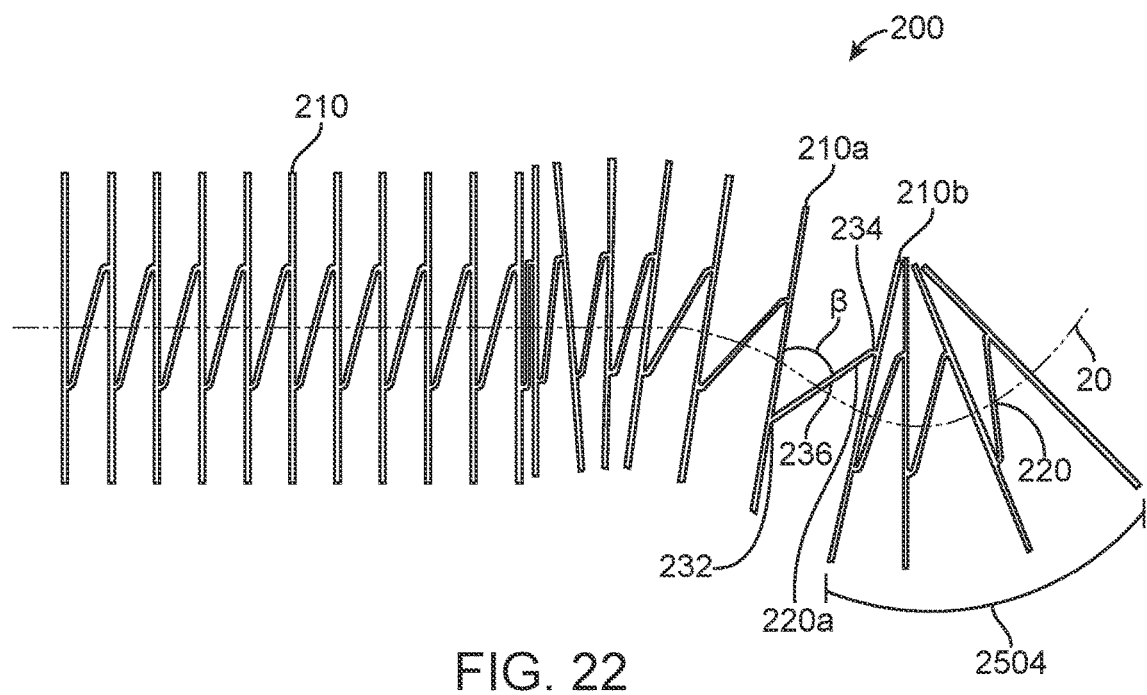
FIG. 22 illustrates another tubular structure with a section being bent.

FIG. 22 illustrates another tubular structure 200. The tubular structure 200 of FIG. 22 is similar to, and may be considered a variation of FIGS. 2A-2B and FIGS. 21A-21B. Similarly to FIGS. 2A-2B and FIGS. 21A-21B, the tubular structure 200 of FIG. 22 has a plurality of closed-loops ring elements 210 arranged in series along the longitudinal axis 20 and substantially parallel to each adjacent ring element 210 when the tubular structure 200 is in a relaxed state. Another similitude to FIGS. 2A-2B is that the connecting members 220 of FIG. 22 includes a first member end 232, a second member end 234 opposite from the first member end 232, and a member body 236 extending between the first member end 232 and the second member end 234.

A difference with FIGS. 2A-2B is that the tubular structure 200 of FIG. 22 includes a pair of connecting members 220 between adjacent ring elements 210. A difference with FIGS. 21A-21B is that the each pair of connecting members 220 of FIG. 22 forms an obtuse angle β with respect to the ring element 210 proximately disposed to another adjacent ring element 210 (e.g., angle β between 210a and 210b, as the angle is measured with respect to 210a as the base). For example, the member body 236 forms an obtuse angle α with respect to the ring element 210a. In some cases, the angle α may be measured with the tubular structure 200 being "un-rolled" to a flat configuration. In view of the angle α, the first member end 232 of the connecting member 220a and the second member end 234 of the connecting member 220a define a line that is non-parallel to the longitudinal axis 20 of the tubular structure 200. Further, first member end 232 and the second member end 234 include an arcuate configuration while the member body 236 includes a rectilinear configuration.

Figure 23:
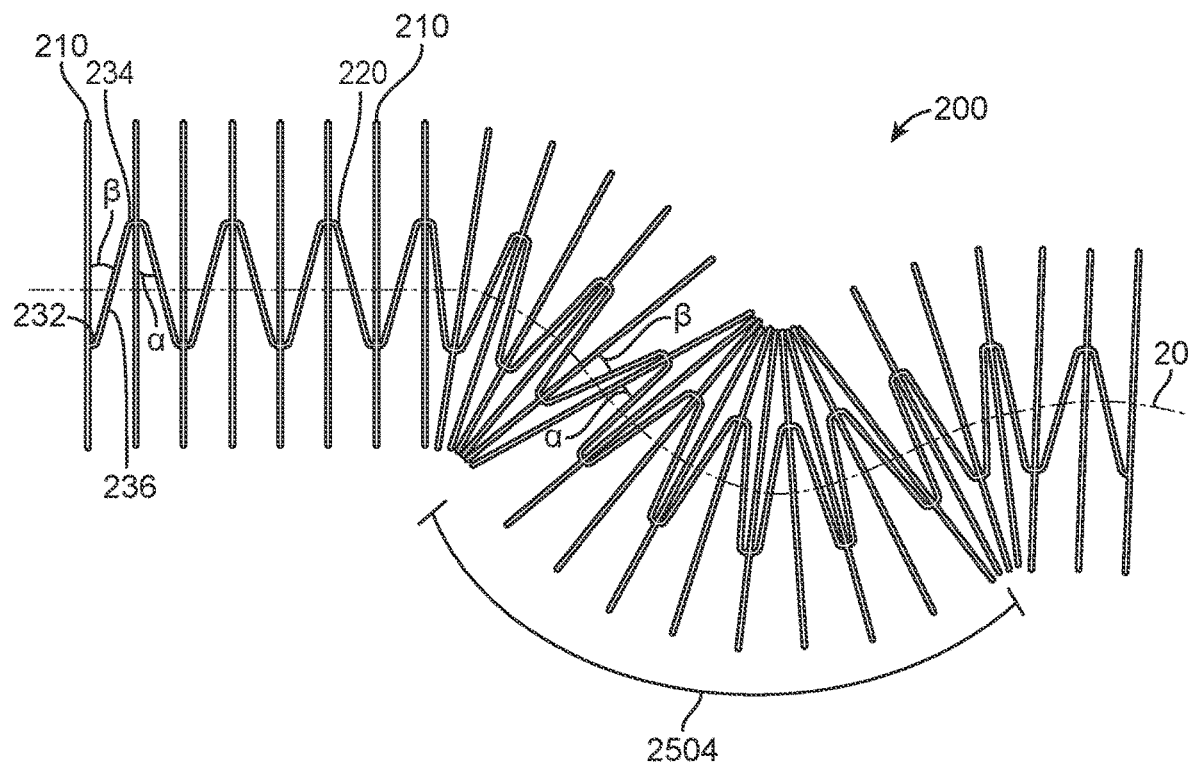
FIG. 23 illustrates another tubular structure a section being bent.

FIG. 23 illustrates an alternative embodiment to the tubular structure 200 of FIG. 22. Similar to FIG. 22, tubular structure 200 of FIG. 23 includes a plurality of closed-loops ring elements 210 arranged in series along the longitudinal axis 20 and substantially parallel to each adjacent ring element 210 when the tubular structure 200 is in a relaxed state. FIG. 23 includes a pair of connecting members 220 between adjacent ring elements 210. Also, the connecting members 220 of FIG. 23 includes a first member end 232, a second member end 234 opposite from the first member end 232, and a member body 236 extending between the first member end 232 and the second member end 234. Further, first member end 232 and the second member end 234 include an arcuate configuration while the member body 236 includes a rectilinear configuration.

A difference with FIG. 22 is that each pair of connecting members 220 in FIG. 23 forms alternating acute α and obtuse β angles with respect to the ring element 210 proximately disposed to another adjacent ring element 210. The alternating angles α and β illustrate a zig-zag configuration of the connecting members 220 of the tubular structure 200, as shown in FIG. 23.

FIG. 21, FIG. 22 and FIG. 23 further illustrates respective bending sections 2504 of the tubular structures 200. As shown by sections 2504, when the tubular structure 200 is being bent, the ring elements 210 stay substantially perpendicular (e.g., 90 degrees+/−10 degrees) to the longitudinal axis 20. The connecting members 220 are configured to move (e.g., flex, bend, and/or translate) relative to the ring elements 210 in correspondence with the bending of the tubular structure 200. This allows the connecting members 220 to conform to a change in a spacing distance between adjacent ring elements 210 due to the bending of the tubular structure 200. As similarly discussed, the tubular structure 200 is advantageous because the closed-loop ring elements 210 prevent the tubular structure 200 from collapsing radially inward. Thus, the cross-sectional shape of the ring elements 210 are maintained even during bending of the tubular structure 200, and kinking of the catheter 10 is prevented. For example, a circular inner diameter cross-section of tubular structure 200 is substantially maintain when the tubular structure 200 is subjected to tension and/or bending forces, while avoiding and/or minimizing ovalization of the circular inner diameter.

FIGS. 24A-24B illustrate another tubular structure 200. FIG. 24A depicts the pattern of the ring elements 210 and connecting members 220 in a 2D configuration (e.g., cutting pattern on a sheet of material), while FIG. 24B depicts the tubular structure 200 formed with the FIG. 24A pattern (e.g. cut sheet is rolled and ends are coupled to form the tubular structure 200). The tubular structure 200 of FIG. 24B is similar to and may be considered a variation of FIG. 5, such as the majority of the body 236 of each connecting member 220 is parallel to an adjacent ring element 210 when the tubular structure 200 is in a relaxed state. A difference of the tubular structure 200 of FIGS. 24A-24B with respect to FIG. 5 is that a ratio of ring elements 210 to connecting members 220 is higher (e.g. 2:1) than in FIG. 5 (e.g. 1:1). Another difference of the tubular structure 200 of FIG. 24B with respect to FIG. 5 is that the first member end 232 and the second member end 234 of a connecting member 220 are substantially parallel to each other, since the body 236 of each connecting member 220 forms a substantially complete circumference, as shown in FIG. 24B.

Figure 26:
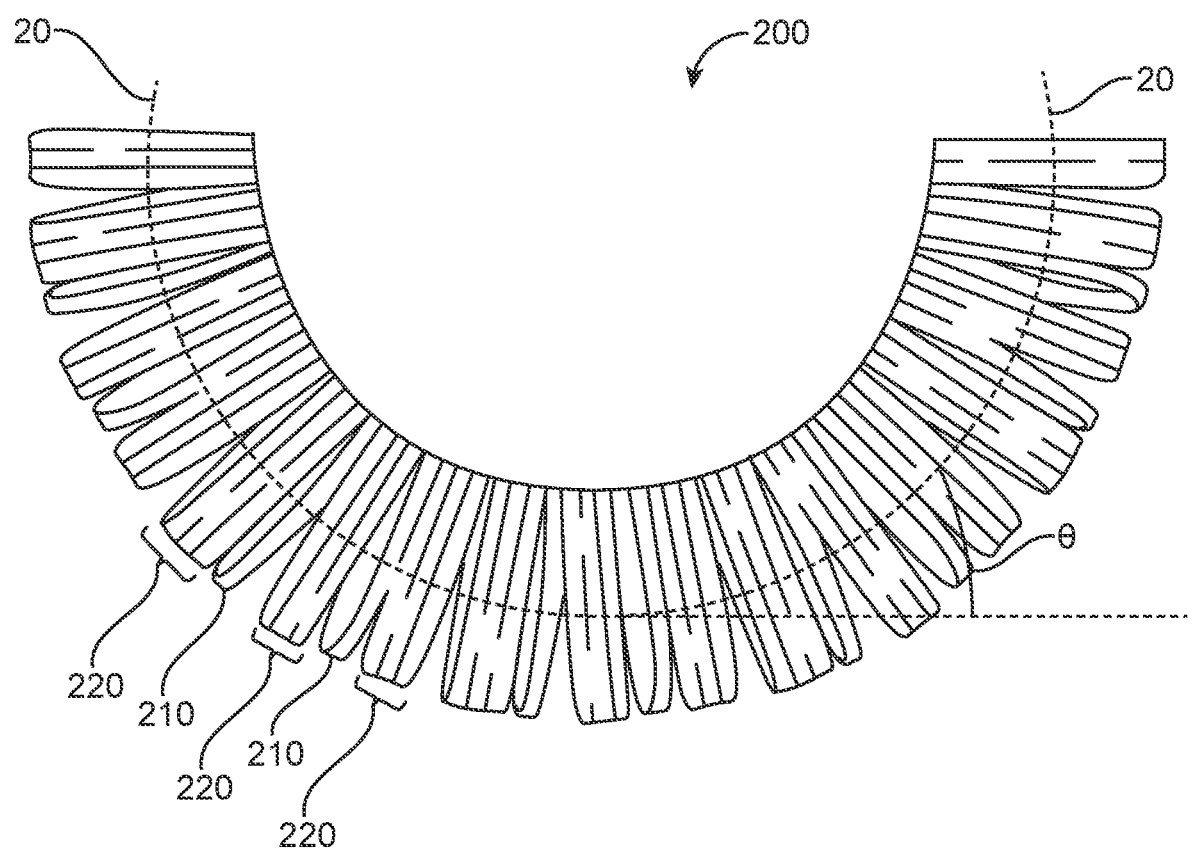
FIG. 26 illustrates a bending of the tubular structure of FIG. 25.
Figure 27:
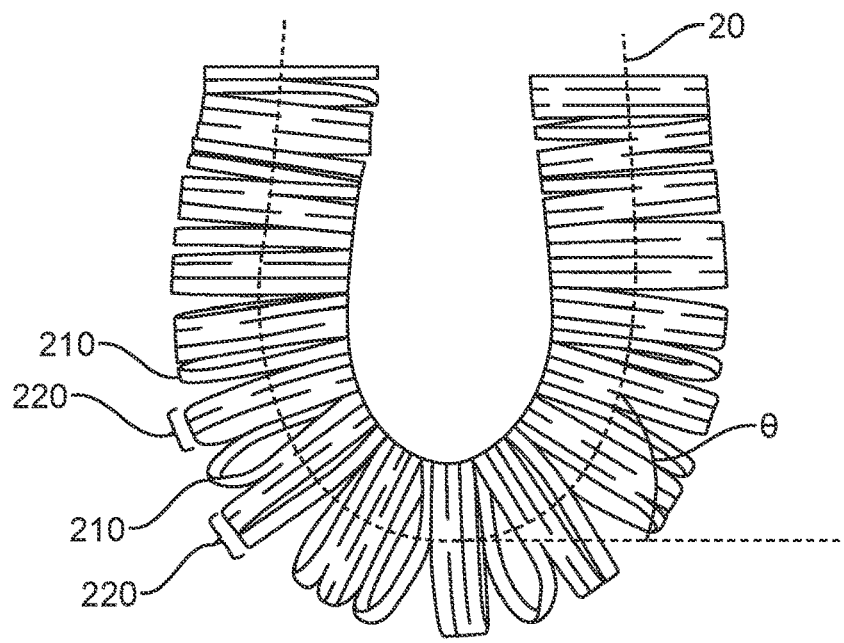
FIG. 27 illustrates a further bending of the tubular structure of FIG. 5.

FIG. 25 illustrates another tubular structure 200. FIG. 25 depicts a pattern of cuts in the tubular structure 200, wherein the cuts are created in a high frequency sinusoidal wave pattern forming interrupted articulation sections 235 between ring elements 210 in the tubular structure 200. The cut pattern as shown in FIG. 25 is configured to balance the forces exerted in the tubular structure 200 when it bends, as shown in FIG. 26 and FIG. 27. The high frequency sinusoidal wave cuts of FIG. 25 creates a ratio of at least 1:3 of ring elements 210 to connecting members 220, as better appreciated in FIG. 26 and FIG. 27.

FIG. 26 and FIG. 27 illustrate bending of the tubular structures 200 of FIG. 25. FIG. 26 shows the tubular structure 200 having a bending angle of 30 degrees (e.g., +/−10 degrees) with respect to the longitudinal axis 20, and FIG. 27 shows the tubular structure 200 having the bending angle at 60 degrees (e.g., +/−10 degrees) with respect to the longitudinal axis 20. When the tubular structure 200 is being bent, the ring elements 210 stay substantially perpendicular (e.g., 90 degrees+/−10 degrees) to the longitudinal axis 20. The connecting members 220 are configured to move (e.g., flex, bend, and/or translate) relative to the ring elements 210 in correspondence with the bending of the tubular structure 200. The connecting members 220 are configured to move in a set of three, as shown in FIG. 26 and FIG. 27, according to the cut pattern shown in FIG. 25, and the ring elements 210 maintain hoop strength allowing the tubular structure 200 to resist kinking while preventing and/or minimizing ovalization of the circular inner diameter of the tubular structure 200.

Figures 28A, 28B:
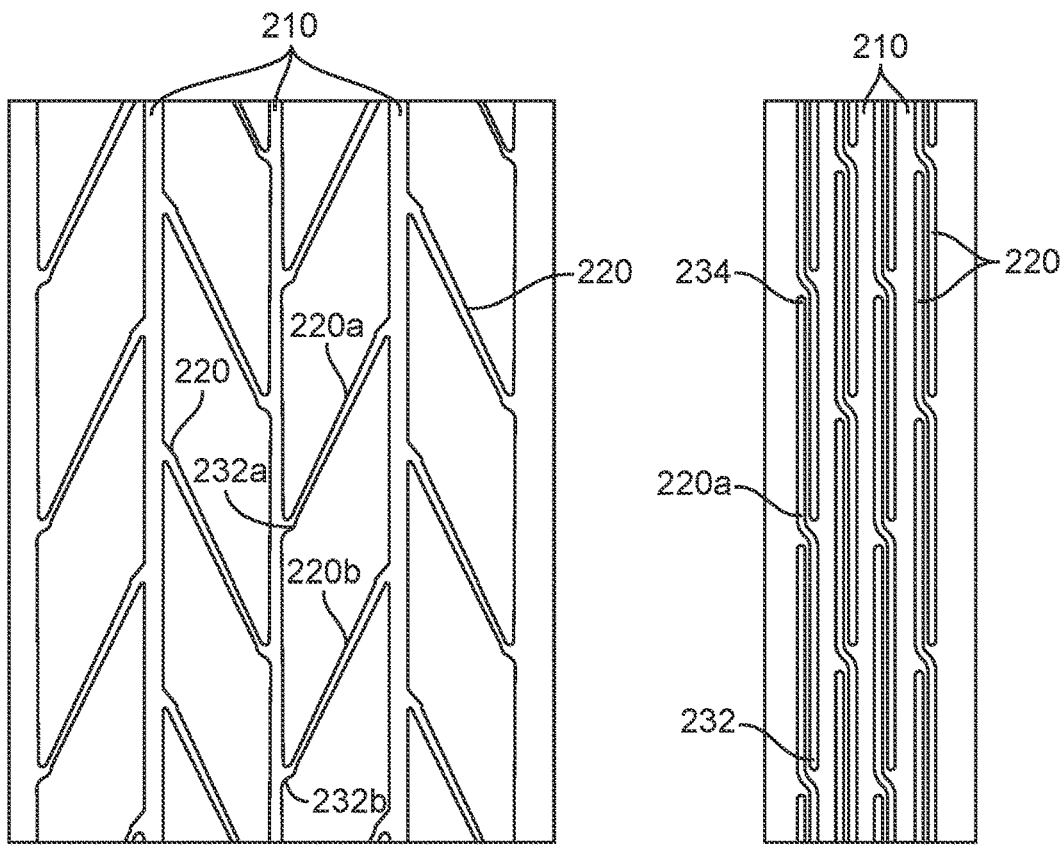
FIGS. 28A-28B illustrate 2D patterns of the others tubular structure.

FIGS. 28A-28B illustrate patterns of ring elements 210 and connecting members 220 in 2D configurations (e.g., cutting patterns on sheets of material) to form other embodiments of the tubular structure 200. FIG. 28A is similar to FIGS. 2A-2B, except that the first member ends 232 and second member ends 234 of respective connecting members 220 are offset (e.g., first member ends 232a and 232b of respective connecting members 220a and 220b, as shown in FIG. 28A). FIG. 28A may be considered as a variation of FIGS. 2A-2B. FIG. 28B is similar to FIG. 24A, except that in in FIG. 28B, the first member end 232 and the second member end 234 of a connecting member 220 (e.g., 220a) are offset, and not substantially parallel to each other, as shown in FIG. 24B. FIG. 28B may be considered as a variation of FIG. 24A.

Figure 29A:
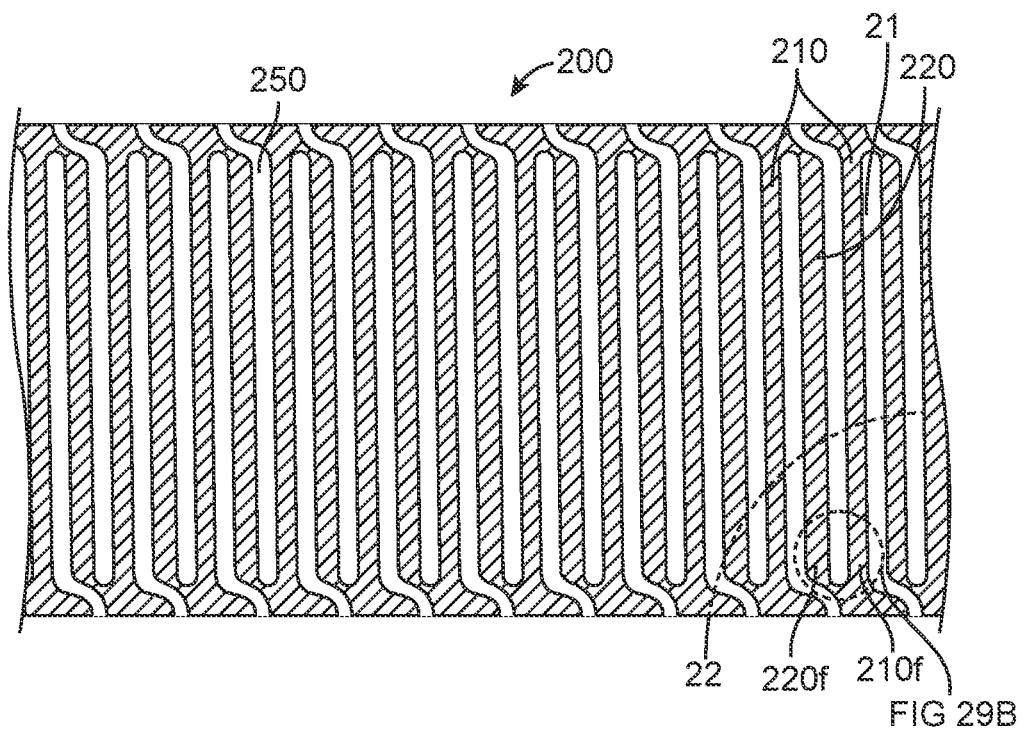
FIGS. 29A-29B illustrate another tubular structure and detailed section thereof.
Figure 29B:
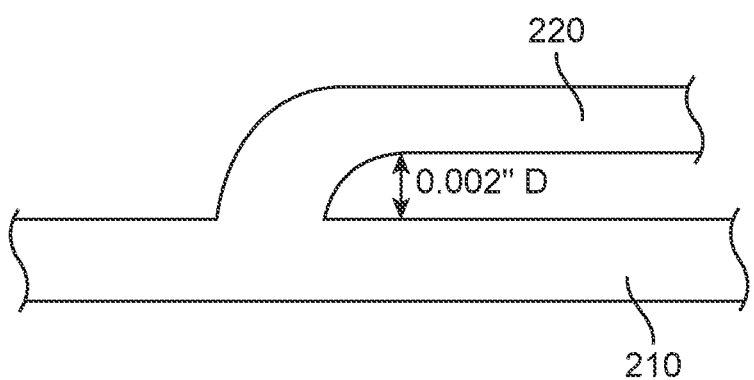

FIG. 29A illustrates another tubular structure 200 with a pattern similar to the one disclosed in FIG. 28B. FIG. 29B illustrates a detailed section of FIG. 29A. As shown in FIG. 29A, the tubular structure 200 includes ring elements 210 and connecting members 220, where each connecting member 220 is parallel to an adjacent ring element 210 when the tubular structure 200 is in a relaxed state. The tubular structure 200 is encapsulated in a biocompatible polymer creating a fluid seal and smooth outer surface 21 and inner surface 22 of tube 11, as described in FIG. 1. The detailed section of the tubular structure 200 of FIG. 29B illustrates a portion of a connecting member 220f parallel to an adjacent ring element 210f and having a distance "D" of 0.002" in between.

Figure 30A:
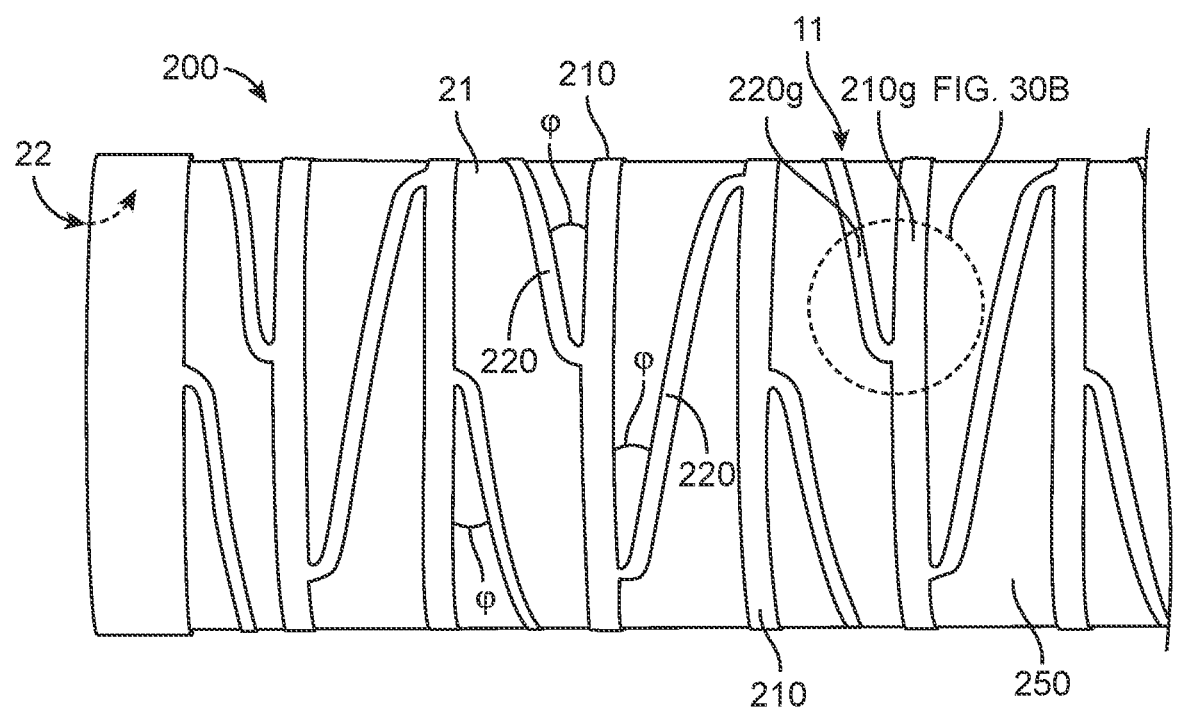
FIGS. 30A-30B illustrate another tubular structure and detailed section thereof.
Figure 30B:
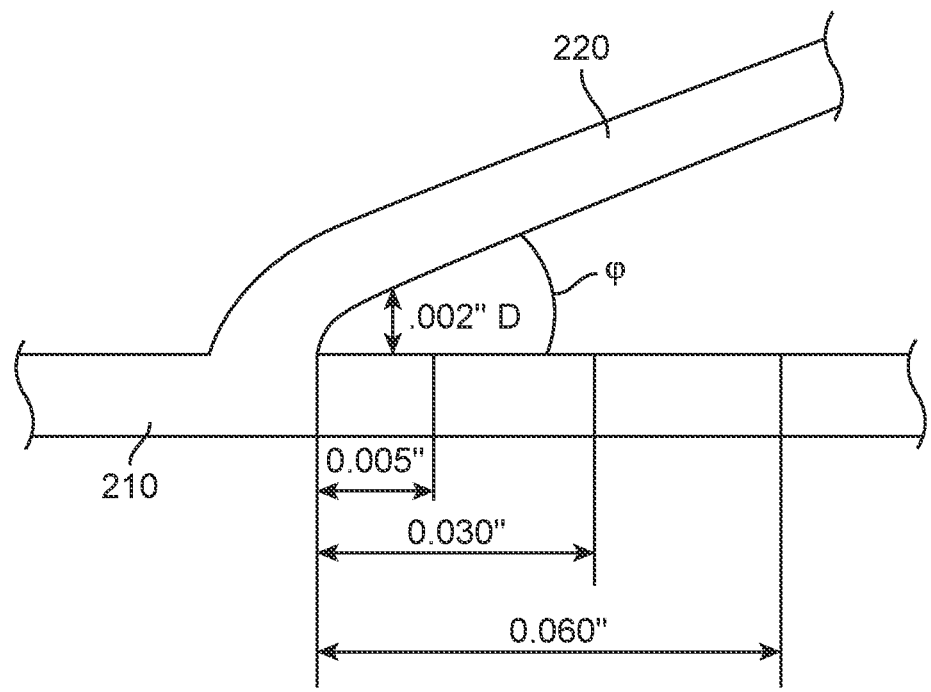

FIG. 30A illustrates another tubular structure 200 with a pattern similar to the one disclosed in FIG. 28A. FIG. 30B illustrates a detailed section of FIG. 30A. As shown in FIG. 30A, the tubular structure 200 includes ring elements 210 and connecting members 220, where the tubular structure 200 is encapsulated in filler 250 (e.g., polymer, plastic, foam, polymeric solution or any of other elastic materials) creating a fluid seal and smooth outer surface 21 and inner surface 22 of tube 11 of catheter 10, as described in FIG. 1. The filler 250 and the tubular structure 200 behave as a composite by sharing tensile and bending loads between the filler 250 and tubular structure 200. The tubular structure 200 having ring elements 210 and connecting members 220 is configured to evenly distribute the loads in the filler 250, such that peak stresses (e.g., quantified by percent of elongation) in the filler 250 are minimized, which ensures higher tensile strength and resistance to rupture of the filler 250. For example, when the tubular structure 200 is elongated (e.g., in tension or in bending), the filler 250 elongation can be more evenly distributed, which allows for an effective load distribution between the filler 250 and tubular structure 200 of the tube 11. Some of these advantages are achieved by having an angle φ between the connecting members 220 and the ring elements 210 (FIGS. 30A-30B) that creates uniform strains in the filler 250 during elongation/bending of the tubular structure 200. The angle φ of the connecting members 220 relative to their respective ring elements 210 is about 10 degrees (e.g., +/−5 degrees) and can be increased or decreased to allow compliance of the filler 250 in order to match the compliance of the tubular structure 200. The detailed section of the tubular structure 200 of FIG. 30B illustrates a portion of a connecting member 220g forming the angle φ of about 10 degrees with respect to an adjacent ring element 210g and having a distance "D" of about 0.002" in between. The angle φ of the connecting members 220 relative to their respective ring elements 210 is configured to increase the tensile strength of the tube 11. For example, variations of the angle φ may increase the peak tensile strength of the tube 11 to at least 200% (e.g., prior to filler 250 failure, break, rupture or the like). The composite effects of sharing tensile and bending loads between the filler 250 and tubular structure 200 may be adjusted (e.g., increase or decrease) by for example, a) varying the angle φ between the connecting members 220 and their respective ring elements 210, b) varying the width and/or the radius of the ring elements 210 and/or connecting members 220, and/or c) varying the amount of connecting members 220 with respect to their respective ring elements 210, among other suitable variations.

In some embodiments, the space between the ring elements 210 and the connecting members 220 may be increased or decrease by varying the length of the connecting members 220, such as to tailor the space to the properties of the filler 250.

FIGS. 31 and FIG. 32 depict data tables with the percentage in length change of the filler 250 as the connecting members 220 of the tubular structure 200 of their respective FIG. 29A-29B and FIG. 30A-30B extends, bends or rotates. The data shown in FIGS. 31 and FIG. 32 reflects the percent of elongation (i.e., stretching) of the filler 250 as their respective tubular structure 200 are stretched causing their respective connecting members 220 to deflect a total of 20 degrees from their starting neutral position (i.e., tubular member 200 in a relaxed state). The elongation of the filler 250 is calculated at 0.005", 0.030" and 0.060" away from a vertex between the connecting members 220 and the ring elements 210. The connecting members 220 of FIG. 29A-29B usually form a non-uniform elongation of the filler 250 versus the connecting members 220 of FIG. 30A-30B. For example, at 20 degrees of total connecting members 220 deflection, the tubular structure 200 of FIG. 29A-29B shows a minimum of 86% elongation and a maximum percent elongation of 1026%, which is above the predicted rupture point of most elastomeric polymers. In contrast, at 20 degrees of total connecting members 220 deflection, the tubular structure 200 of FIG. 30A-30B shows a minimum elongation of 57% and maximum elongation of 158%, such as evenly distributing the strain load and the peak strains (i.e., elongation) are well below the rupture point of most elastomeric polymers.

Figure 33:
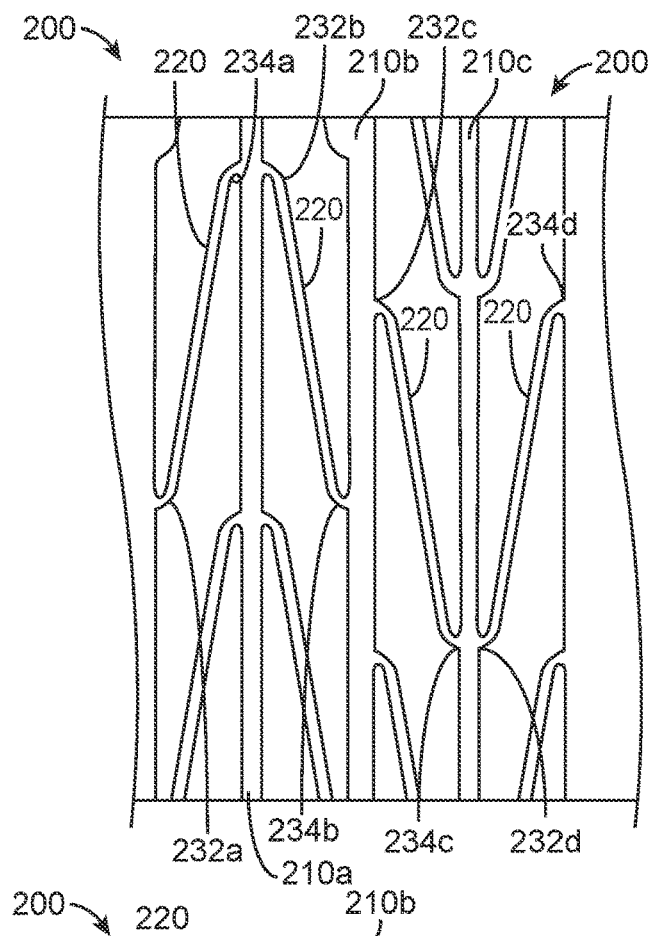
FIG. 33 illustrates another tubular structure 2D pattern.

FIG. 33 illustrates a pattern of ring elements 210 and connecting members 220 in a 2D configuration (e.g., cutting patterns on sheets of material) to form another embodiment of the tubular structure 200. The pattern of FIG. 33 is similar to the one disclosed in FIG. 28A, except that some of the first member ends 232 and some of the second member ends 234 of respective connecting members 220 are substantially parallel to each other (e.g., 234a with 232b, and 234c with 232d) and some of them are offset (e.g., 234b with 232c). Having the connecting members 220 coupled around the ring elements 210 in a parallel and offset pattern, as shown in FIG. 33, is configured to improve the flexibility of the tubular structure 200 when subjected to tensile or bending forces. Further, the ring elements 210 of FIG. 33 have substantially the same length, width and thickness throughout the tubular structure 200 (e.g., 210a, 210b, 210c). FIG. 33 may be considered as a variation of FIG. 28A.

Figure 34:
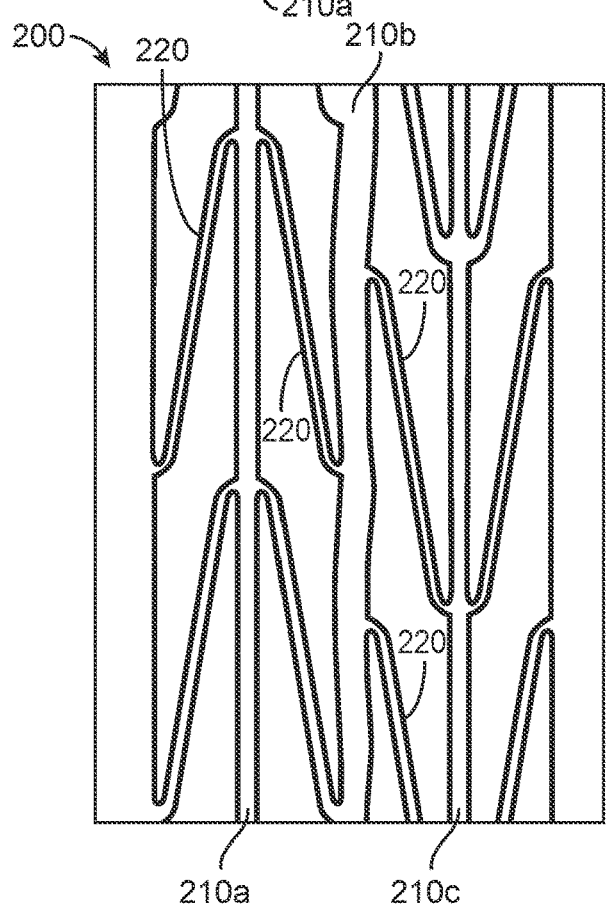
FIG. 34 illustrates a variation of the tubular structure 2D pattern of FIG. 33.

FIG. 34 illustrates a pattern of ring elements 210 and connecting members 220 in a 2D configuration to form another embodiment of the tubular structure 200. The pattern of FIG. 34 is similar to the one disclosed in FIG. 33, except that some of the ring elements 210 of FIG. 34 varied in width and thickness (e.g., 210b). As shown in FIG. 34, the ring element 210b includes an increased width and/or thickness compared to the ring element 210a. Further, the ring element 210b includes curvatures between connecting members 220. The curved and increased width/thickness of the ring element 210b is configured to balance and counteract tensile forces and avoid deformation or ovalization of the ring elements 210 and the tubular structure 200. It should be appreciated that one or more curved thicker ring elements 210 may be disposed throughout the tubular structure 200. FIG. 34 may be considered as a variation of FIG. 33.

FIGS. 35A-37B illustrate other tubular structures 200. FIGS. 35A-35B and 36A-36B depict patterns of cuts made in the tubular structure 200 similar to FIG. 25, wherein the cuts are created in a high frequency sinusoidal wave pattern forming interrupted articulation sections 235 between ring elements 210 in the tubular structure 200. FIGS. 37A-37B depict a pattern of cuts made in the tubular structure 200 similar to FIG. 29A, except that the cuts have a higher frequency and are offset to each adjacent cut, as shown in FIGS. 37A-37B.

Figure 35A:
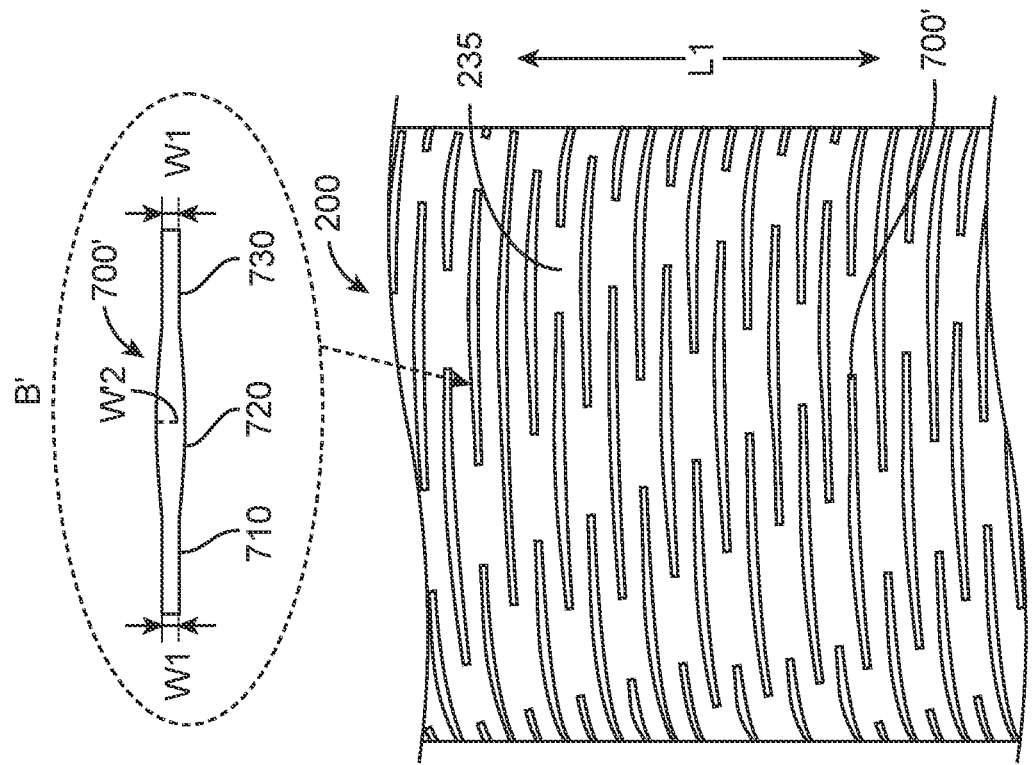
FIGS. 35A-35B illustrate another tubular structure in respective relaxed and stretched configurations.

The cut patterns made in the tubular structures 200 of FIGS. 35A-37B creates slits 700 (e.g., kerfs, slots or their like). Each slit 700 have a first end portion 710, a middle portion 720 and a second end portion 730. The tubular structure 200 of FIG. 35A, FIG. 36A and FIG. 37A are in relaxed state and the tubular structure 200 of FIG. 35B, FIG. 36B and FIG. 37B are longitudinally stretched, as shown by arrows L1. The slits 700 of the tubular structure 200 in FIG. 35A, FIG. 36A and FIG. 37A have a uniform configuration, such as having a substantially constant width W1 along their respective first end portion 710, middle portion 720 and second end portion 730. For example, as shown in detailed and enlarged view A' of a single slit 700 of FIG. 35A. In contrast, the slits 700' of the tubular structure 200 of FIG. 35B, FIG. 36B and FIG. 37B have a non-uniform configuration, due to the longitudinally stretching of the tubular structure 200. For example, the slits 700' have a substantially constant width W1 along the first end portion 710 and the second end portion 730, having a larger width W2 along the middle portion 720; as shown in detailed and enlarged view B' of a single slit 700' of FIG. 35B. In another example, the slits 700' have a substantially constant width W1 along the first end portion 710 and the second end portion 730, having a reduced width W3 along the middle portion 720; as shown in detailed and enlarged view C' of a single slit 700' of FIG. 37B.

Figure 35B:
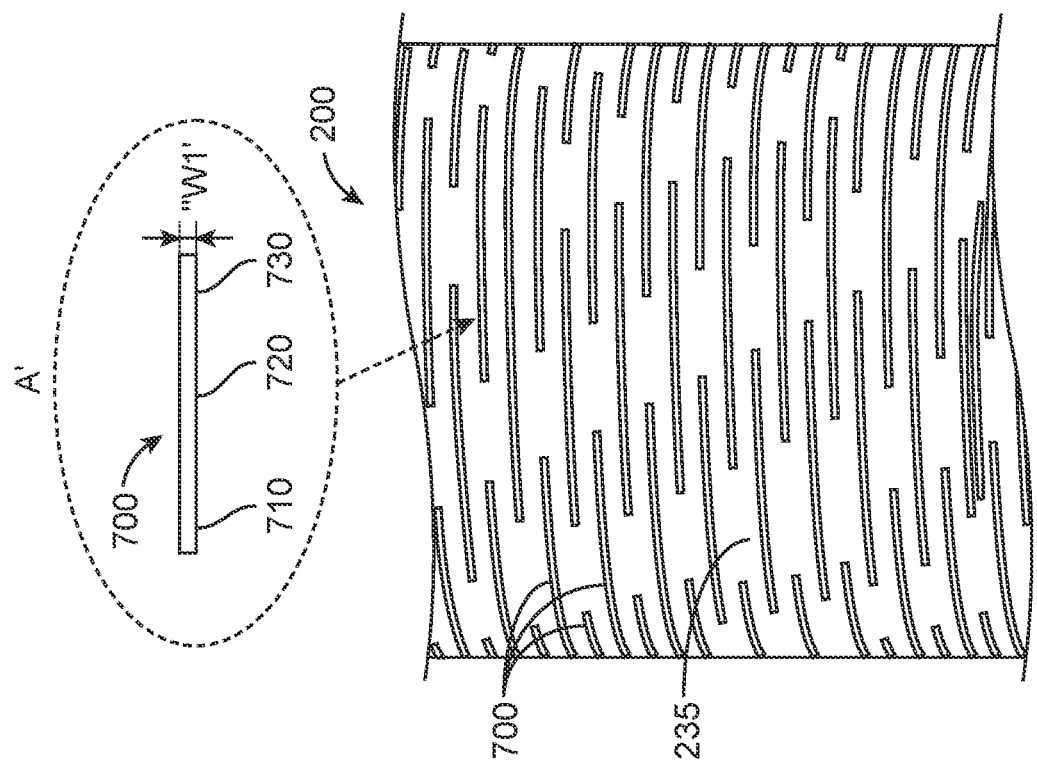

In the embodiments of FIG. 35B, FIG. 36B and FIG. 37B, the tubular structures 200 are created by longitudinally stretching and heat setting the respective tubular structures 200 of FIG. 35A, FIG. 36A and FIG. 37A. In some embodiments, the tubular structures 200 of FIG. 35A, FIG. 36A and FIG. 37A are composed of super-elastic Nitinol, such that when stretched and heat set, results in the tubular structures 200 of FIG. 35B, FIG. 36B and FIG. 37B having wider slits 700'. It should be appreciated that the tubular structures 200 of FIG. 35A, FIG. 36A and FIG. 37A may be composed of any other suitable metal, alloy, polymer, and/or material configured to maintain a stretched or plastic deformed configuration by heat setting, shot-peening or laser shock peening or any other suitable techniques.

The tubular structures 200 of FIG. 35B, FIG. 36B and FIG. 37B having wider slits 700', due to stretching and heat set configuration, allow tighter bend radius of the tubular structures 200 without fully closing the slits 700' (e.g., 'crashing' adjacent ring elements). The condition called crashing is produced when tubular structures have narrow slits (e.g., about 15 microns), since such narrow slits allow limited bending of tubular structures before the slits on the inside of the bend fully close at their center points. Additionally, the narrow slits exacerbate the stiffening of the tubular structures, which along with the crashing condition; limit the performance of tubular structures manufacture with a cost-effective interrupted-helix slit pattern.

The slits 700' in the tubular structures 200 of FIG. 35B, FIG. 36B and FIG. 37B are manufactured by stretching tubular structures 200 such as to open and/or widen of the slits 700 of FIG. 35A, FIG. 36A and FIG. 37A to about 100%. For example, slits 700 having a width of 15 microns each are opened to form the slits 700' having a width of 30 microns each, by the widening of about 100% of slits 700. Further, it should be appreciated that the widening of the slits 700 may range from 50% to 150%, or any other suitable stretching, opening or widening, to avoid or minimize crashing condition and allow tighter bend radius in a flexible section of the tubular structures 200.

Additionally, the tubular structure 200 of FIG. 35B, FIG. 36B and FIG. 37B may be encapsulated in filler 250 (e.g., polymer, plastic, foam, polymeric solution or any of other elastic materials) creating a fluid seal and smooth outer surface (not shown); where the wider slits 700' are configured to reduce the degree of stiffening of the filler 250 when the tubular structure 200 is subjected to bending forces. As such, when the tubular structure 200 having wider slits 700' bend laterally through a curve, the filler 250 spanning the slits 700' stretch allowing the slits 700' on the outside of the curve to open. The wider slits 700' are configured to lower the strain percentage required in the filler 250 to allow the slots to open.

Some of the further advantages of the wider slits 700' in the tubular structures 200 of FIG. 35B, FIG. 36B and FIG.

37B, are: a) improvement in the wicking of adhesive from the exterior to the interior of the tubular structures 200, flow of laminate or dip coat, and ability to visually confirm the extent of adhesive wicking, flow of laminate or dip coat, b) improvement in the UV light penetration to the interior diameter of the tubular structures 200 for the purpose of curing UV adhesives, and c) avoid or minimize entrapment of air inside the slits 700' of the tubular structures 200 in the coating process.

Figure 38A:
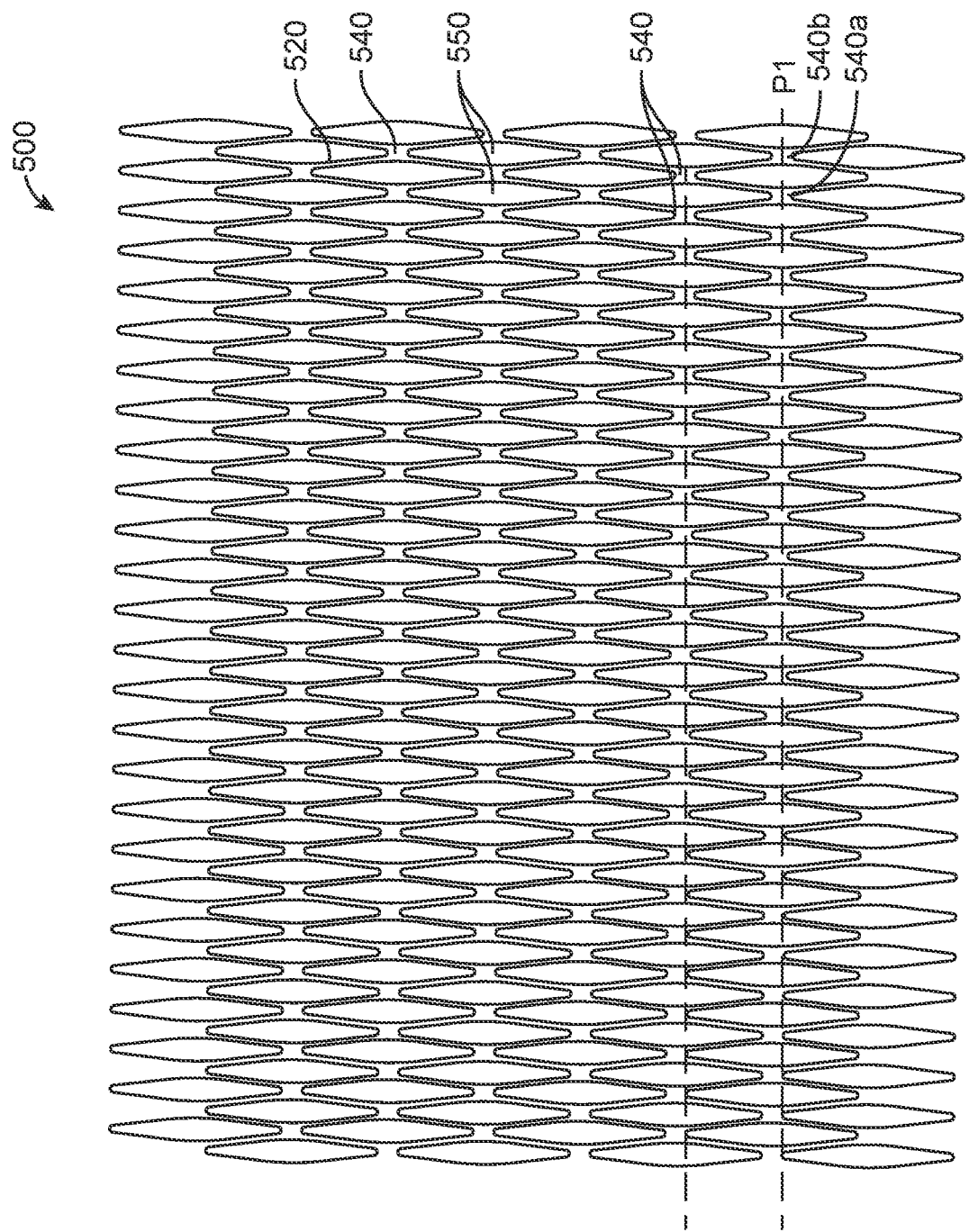
FIGS. 38A-38H illustrate another tubular structure and various bending of the same.
Figure 38B:
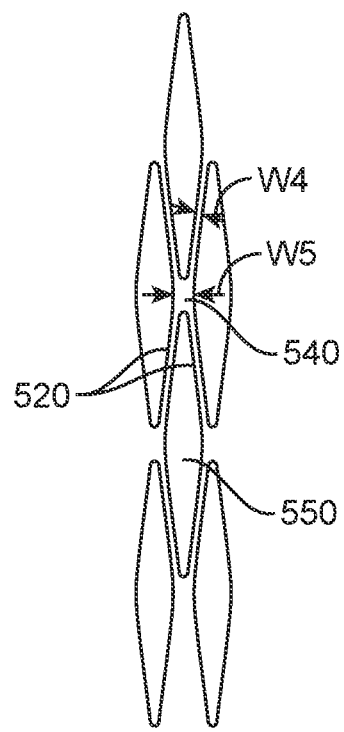
Figure 38C:
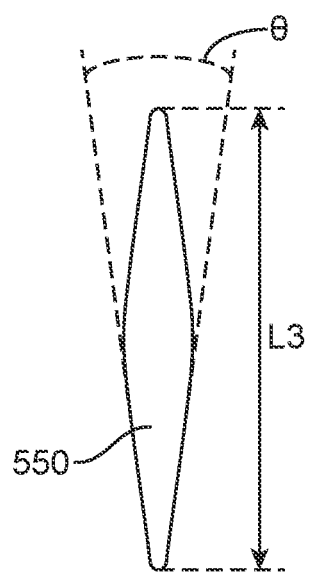

FIGS. 38A-38H illustrate another tubular structure 500. FIG. 38A illustrates part of the tubular structure 500 and FIGS. 38B-38C illustrate enlarged sections of FIG. 38A. The tubular structure 500 comprises elongated members 520 that are arranged in crisscross configuration. The tubular structure 500 further comprises articulation sections 540 coupling the elongated members 520 and defining diamond-shaped cells 550. Each member 520 is coupled to an adjacent member 520 by an articulation section 540. Adjacent articulation sections 540 of the tubular structure 500 are disposed in the same longitudinal plane, as shown in FIG. 38A, as for example the adjacent articulation sections 540a and 540b under longitudinal plane P1. In the embodiment of FIGS. 38A and 38B, each articulation section 540 comprises four members 520 forming respective cells 550, as better appreciated in FIG. 38A-38C. Unlike the tubular structure 200, the tubular structure 500 does not have any closed-loop ring elements that lie in respective planes.

Figure 39:
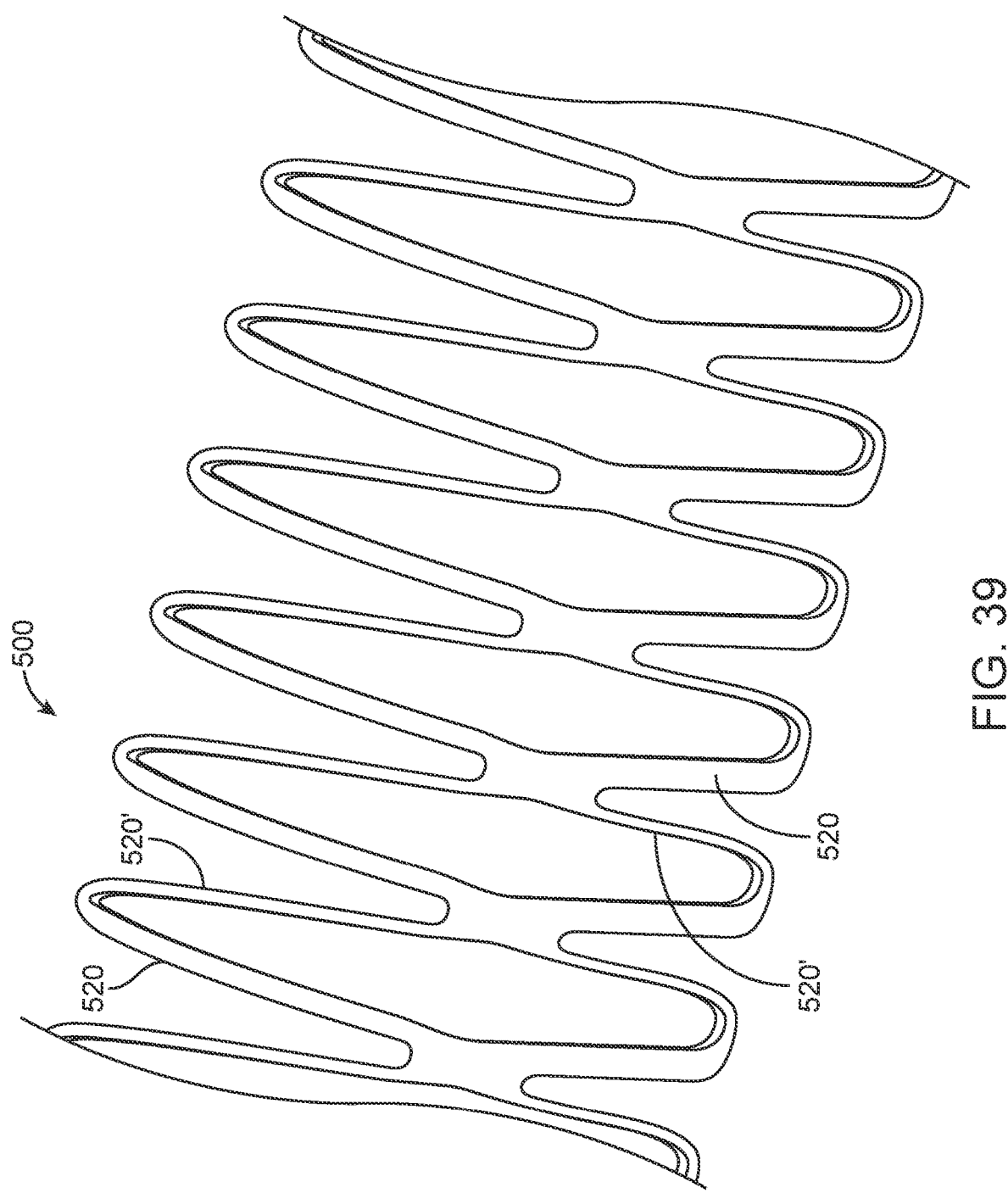
FIG. 39 illustrates a variation of the tubular structure of FIGS. 38A-38H.

In some embodiments, the members 520 may have a width W4 that ranges between 0.002 to 0.003 inches and the articulation sections 540 may have a width W5 that ranges between 0.005 to 0.017 inches, as shown in FIG. 38B. In other embodiments, the members 520 may have a width that is less than 0.01 inches or less than 0.005 inches. Also, in other embodiments, the articulation section 540 may have any width that is larger than the width of the member 520. In further embodiments, the articulation section 540 may have a width that is larger than 0.017 inches. The cells 550 may have a length L3 that ranges between 0.0618 and 0.127 inches and an angle θ that ranges between 13 to 15 degrees in a relaxed configuration, as shown in FIG. 38C. It should be appreciated that variation and/or combinations of dimensions of the elements of the tubular structure 500 may be desired. For example, FIG. 39 illustrates an alternative embodiment of the tubular structure 500, comprising members 520 having a width of 0.003 inches and members 520' having a width of 0.002 inches.

Figure 38D:
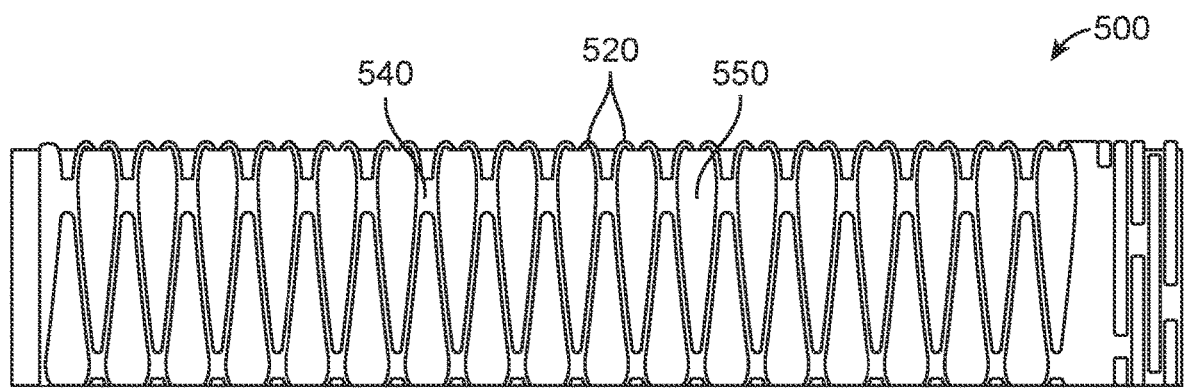
Figure 38E:
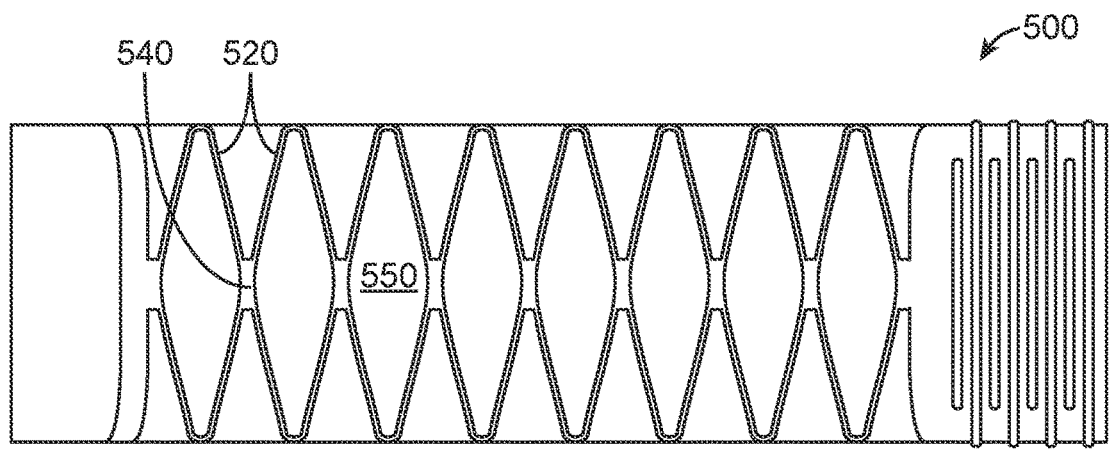
Figure 38F:
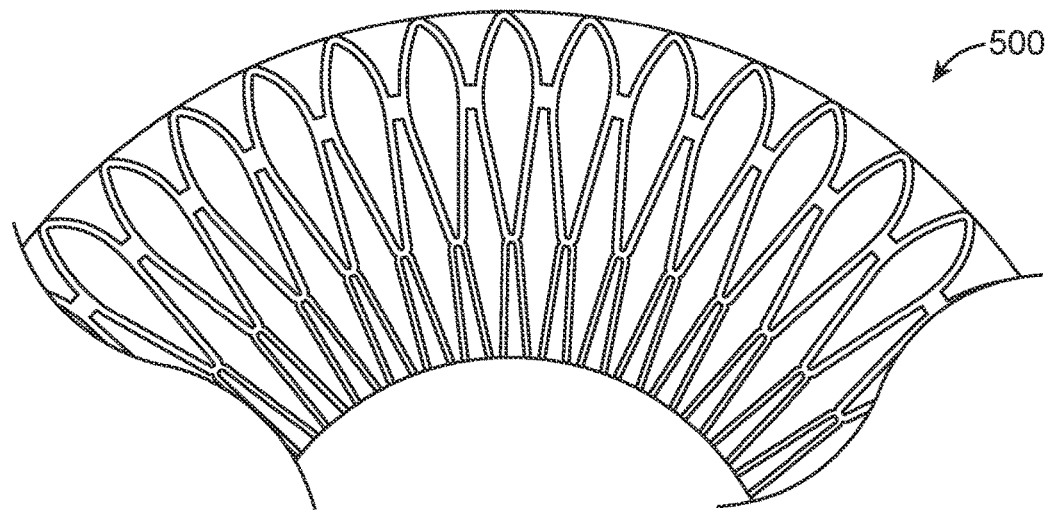
Figure 38G:
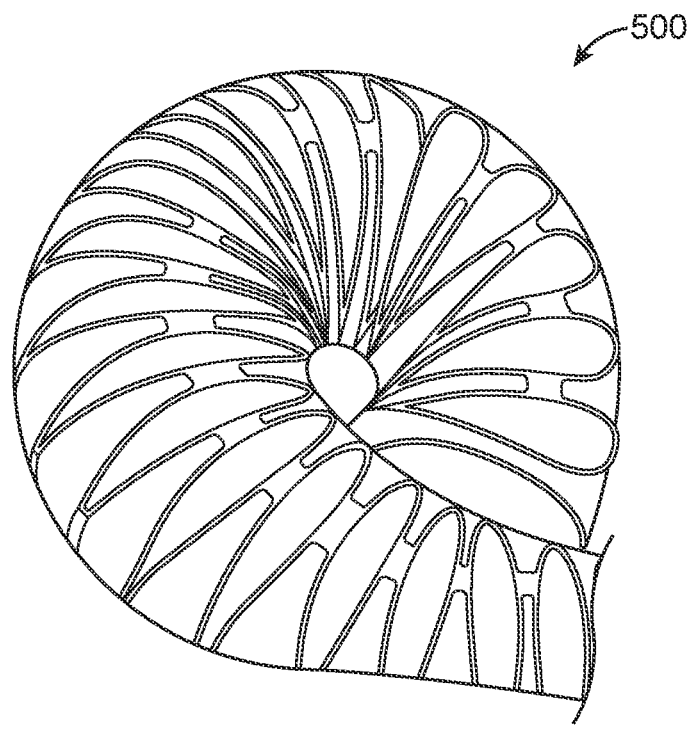
Figure 38H:
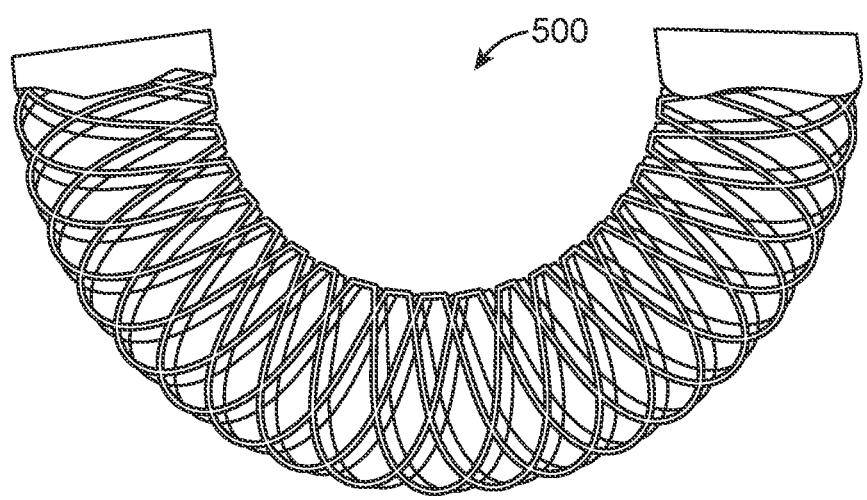

FIG. 38D illustrates the tubular structure 500 comprising elongated members 520, articulation sections 540 and defining diamond-shaped cells 550 in a relaxed configuration and FIG. 38E illustrates the tubular structure 500 in a longitudinal stretched configuration. FIGS. 38F-38H illustrate various bending of the tubular structure 500, configured to be flexible and kink resistance during bending.

Figure 40:
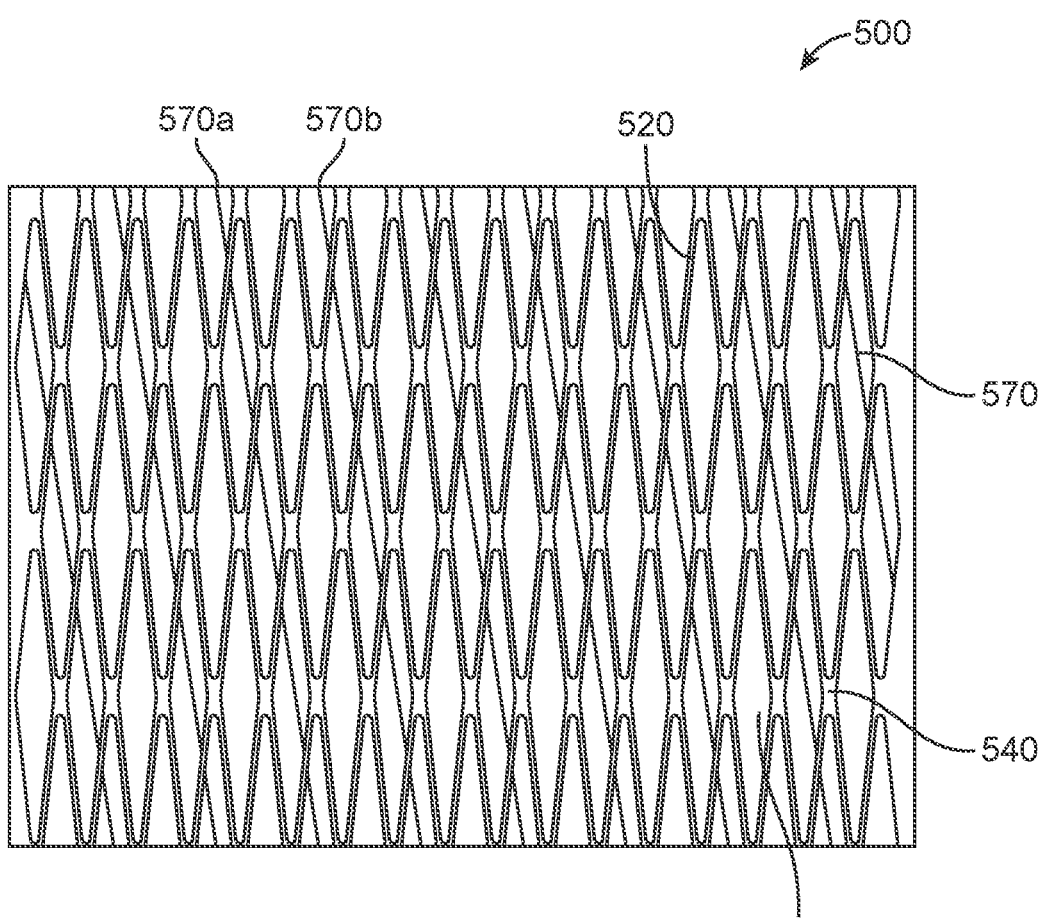
FIG. 40 illustrates another variation of the tubular structure of FIGS. 38A-38H.

FIG. 40 illustrates an alternative embodiment of the tubular structure 500 of FIGS. 38A-38H. The tubular structure 500 comprises the elongated members 520 and articulation sections 540 defining diamond-shaped cells 550, and further comprises one or more tensile members 570 helically wound around the tubular structure 500. The tensile members 570 are configured to intersect some cells 550, and are offset from each adjacent tensile member 570, as shown in FIG. 40, for example in the tensile members 570a and 570b. The tensile members 570 are configured to increase flexibility and improve load distribution of the tubular structure 500.

Figure 41A:
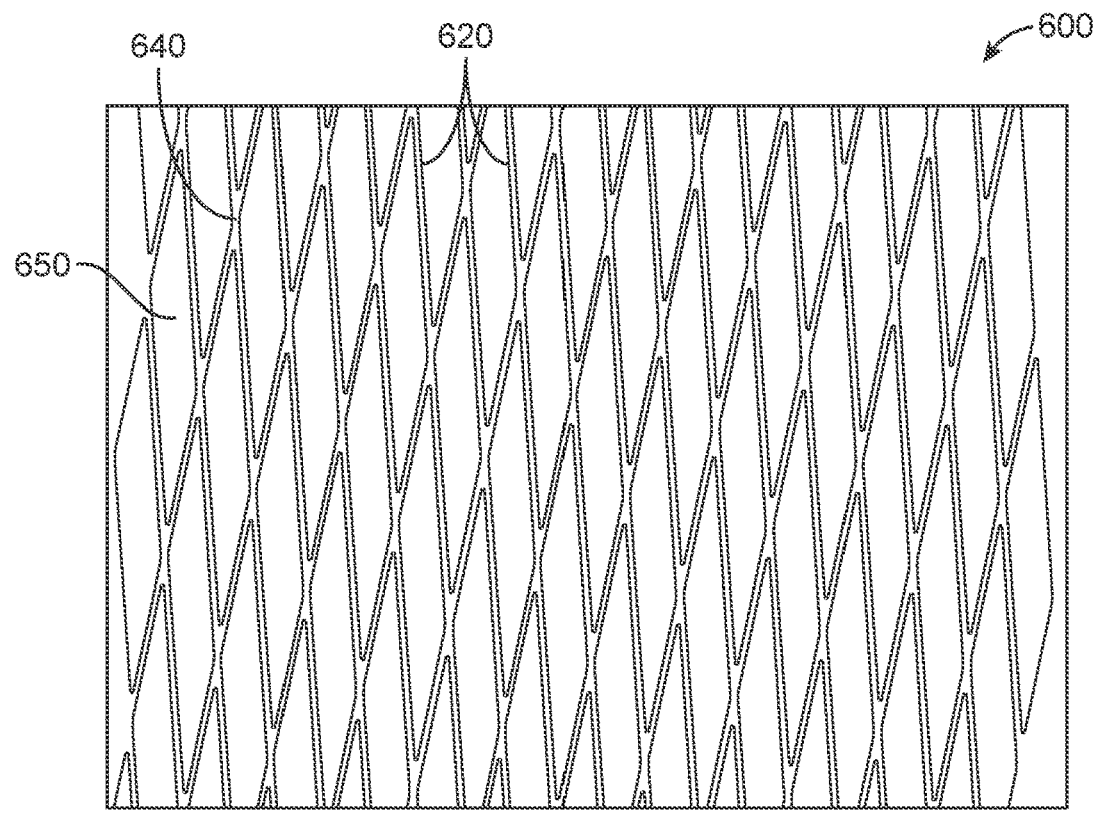
FIGS. 41A-41C illustrates another tubular structure and bending of the same.
Figure 41B:
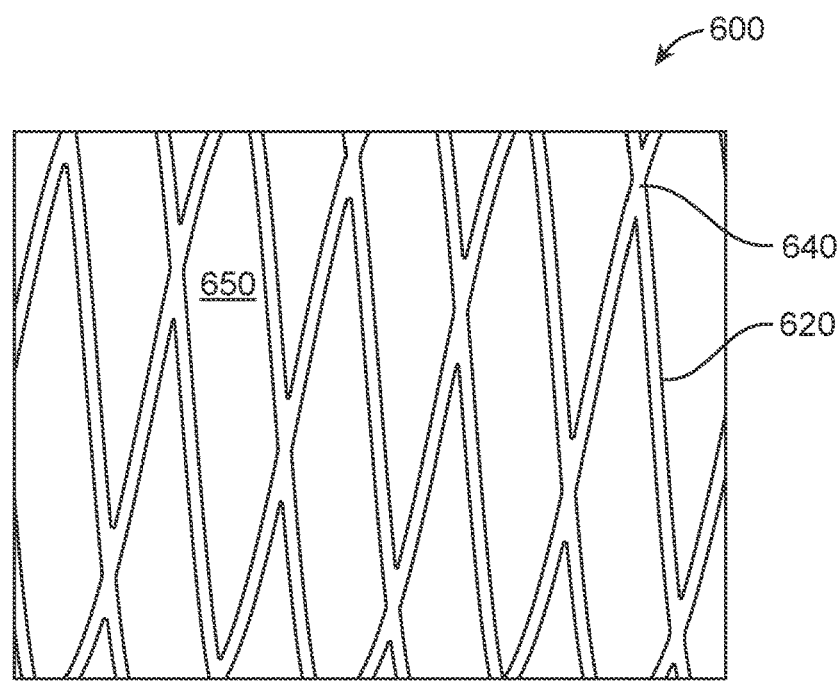
Figure 41C:
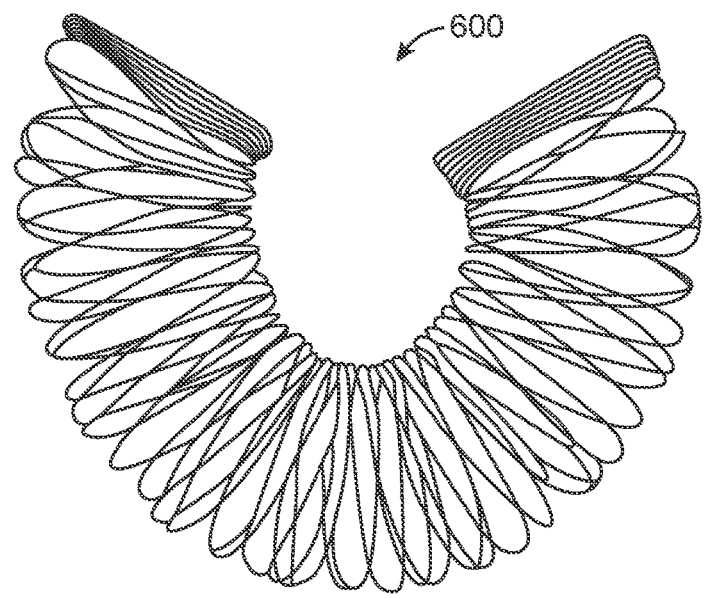

FIGS. 41A-41C illustrate another tubular structure 600. FIG. 41A illustrates part of the tubular structure 600, FIG. 41B illustrates an enlarged section of FIG. 41A, and FIG. 41C illustrates the bending of the tubular structure 600. Similar to the tubular structure 500 of FIGS. 38A-38H, the tubular structure 600 comprises elongated members 620 and articulation sections 640 coupling the elongated members 620, except that the articulation sections 640 are off-set (i.e., not in the same longitudinal plane) and define cells 650 comprising a parallelogram shape (i.e., off-set diamond shape). The parallelogram-shaped cells 650 are configured to increase flexibility of the tubular structure 600.

Figure 42A:
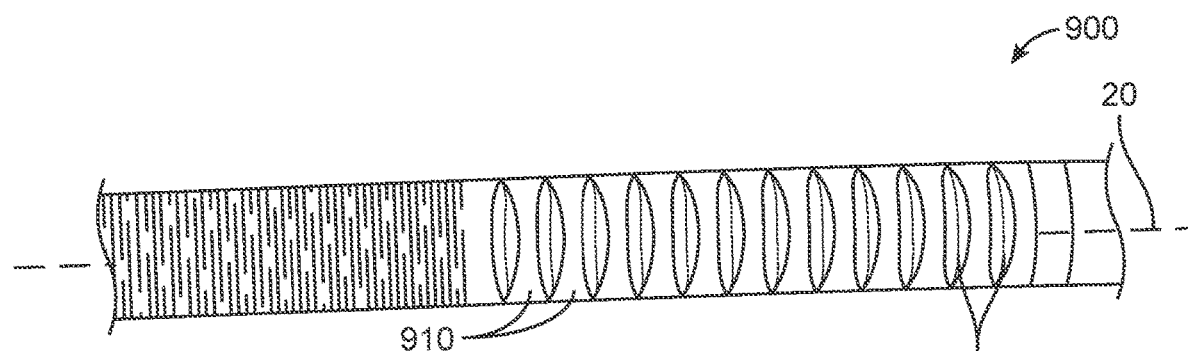
FIGS. 42A-42F illustrate another tubular structure and bending of the same.
Figure 42B:
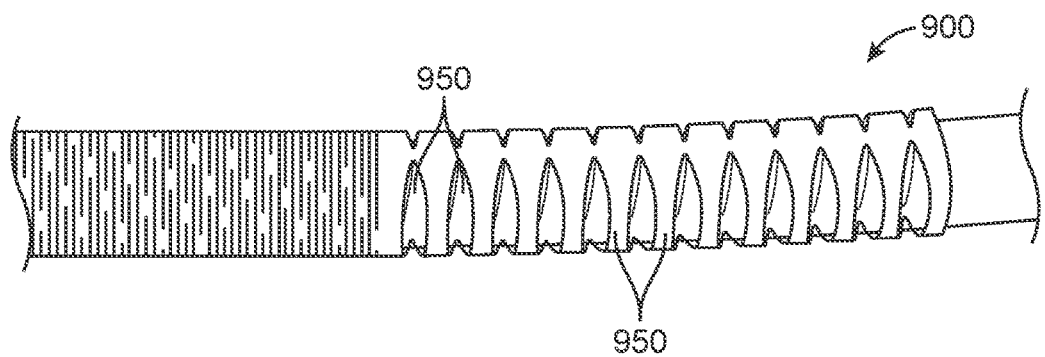
Figure 42C:
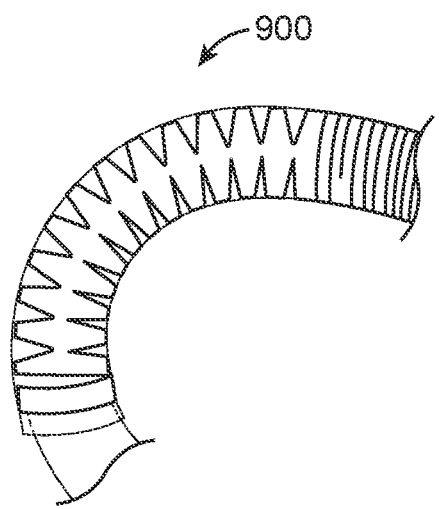
Figure 42D:
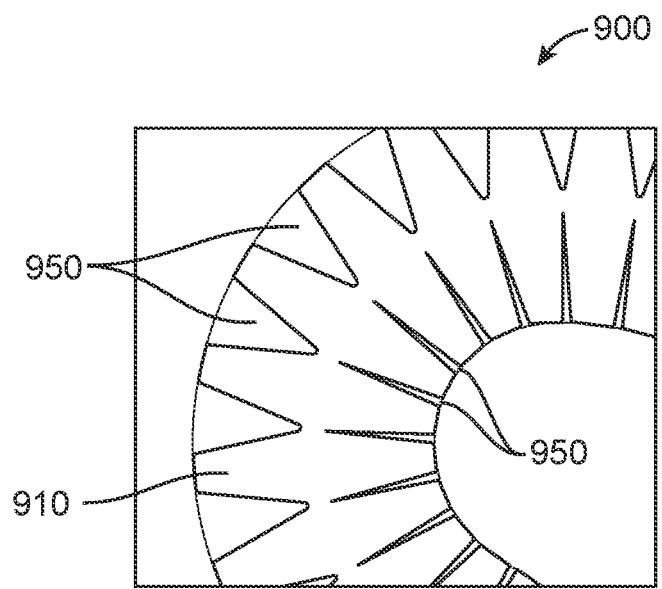
Figure 42E:
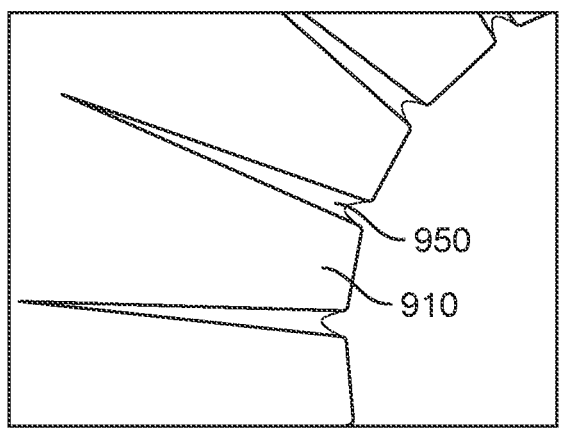
Figure 42F:
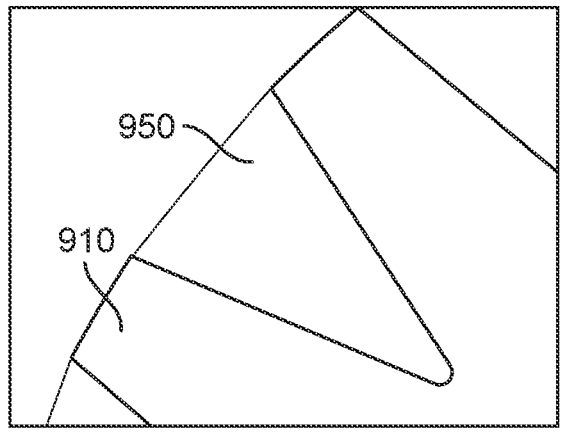

FIGS. 42A-42F illustrate another tubular structure 900. The tubular structure 900 comprises a plurality of diamond-shaped ring elements 910 and V-cuts 950 along a longitudinal axis 20. As shown in FIG. 42A, the tubular structure 900 is in a relaxed configuration and in FIG. 42B where the tubular structure 900 is in a longitudinally stretched configuration. FIGS. 42C-42F illustrate the bending and bending sections of the tubular structure 900. It should be appreciated that the frequency and dimensions of the cuts 950 may vary to increase flexibility of the tubular structure 900.

Figure 43:
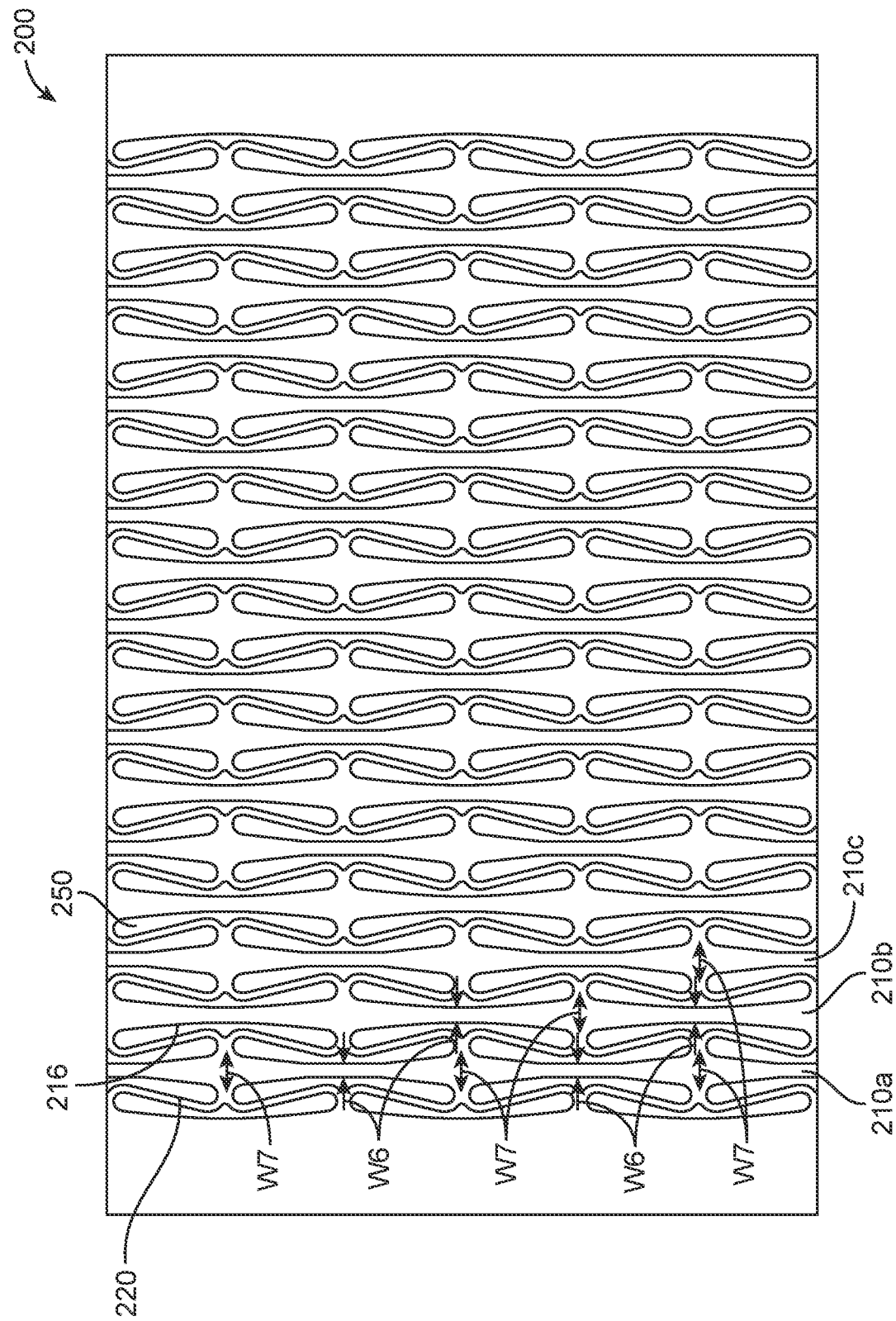
FIG. 43 illustrates another tubular structure.

FIG. 43 illustrates another tubular structure 200. The tubular structure 200 is similar to that of FIGS. 11-13, except that the tubular structure 200 of FIG. 43 comprises ring elements 210 that alternate width along the respective length of each ring (e.g. width W7 wider than width W6 along the length of ring 210a) and with respect to each adjacent ring (e.g., ring element 210a wider width W7 is laterally disposed to adjacent ring element 210b narrower width W6, and ring element 210b narrower width W6 is laterally disposed to adjacent ring element 210c wider width W7). The alternating narrower width W6 and wider width W7 of the ring elements 210 occupy alternating more and less space, as shown in FIG. 43, thereby reducing or augmenting the amount of space that is between the ring elements 210 and the connecting members 220. As a result, more or less filler 250 will be disposed in the space 216 that is between the ring elements 210 and the connecting members 220, depending on the width of the ring elements 210. By configuring an alternating amount of filler material that is placed between the ring elements 210 and the connecting members 220, stiffness, flexibility and/or degree of maximum bending (for a medical device incorporating the tubular structure 200) can be tailored.

Figure 44A:
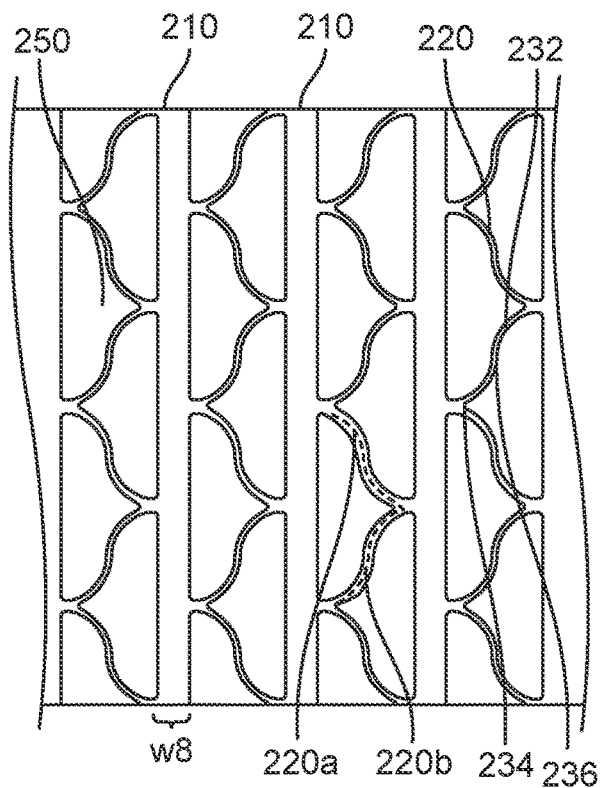
FIGS. 44A-44E illustrate another tubular structure, stretching and bending of the same.
Figure 44B:
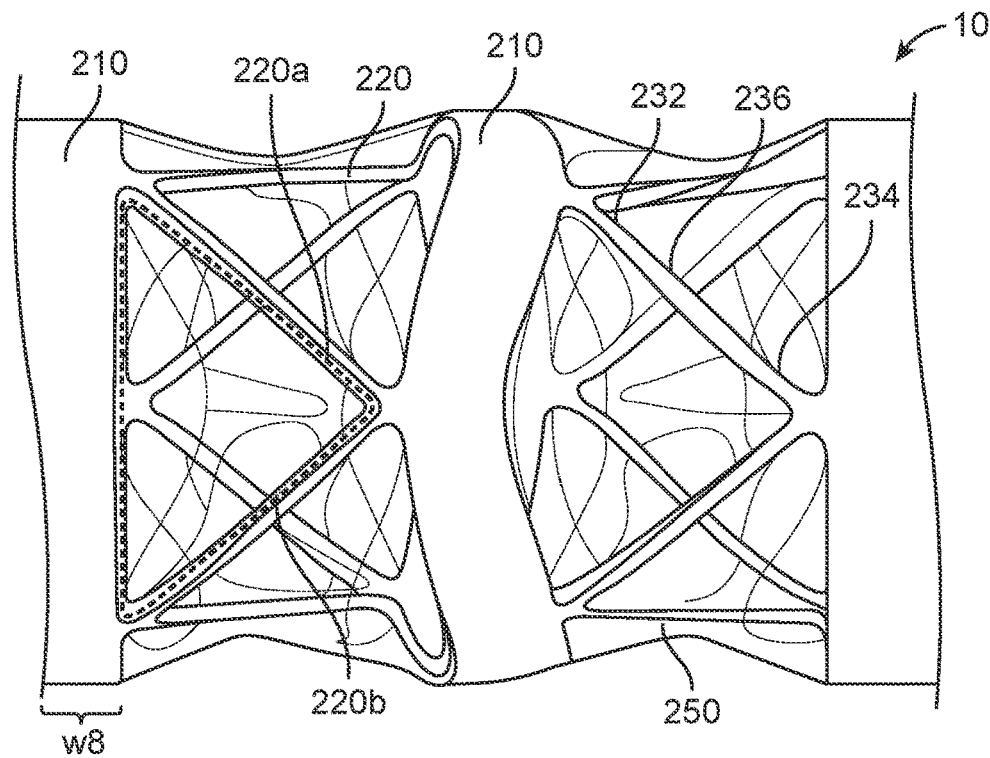
Figure 44C:
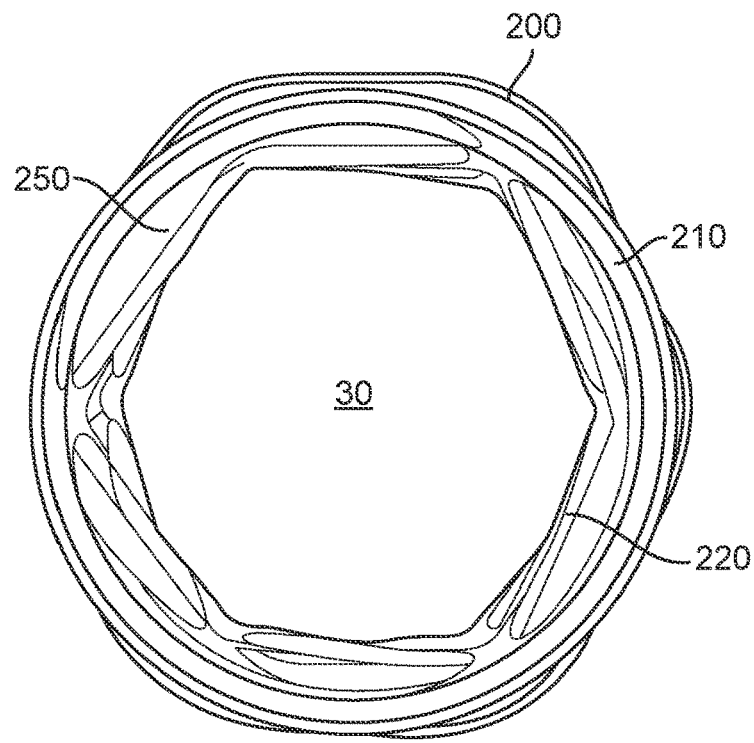
Figure 44D:
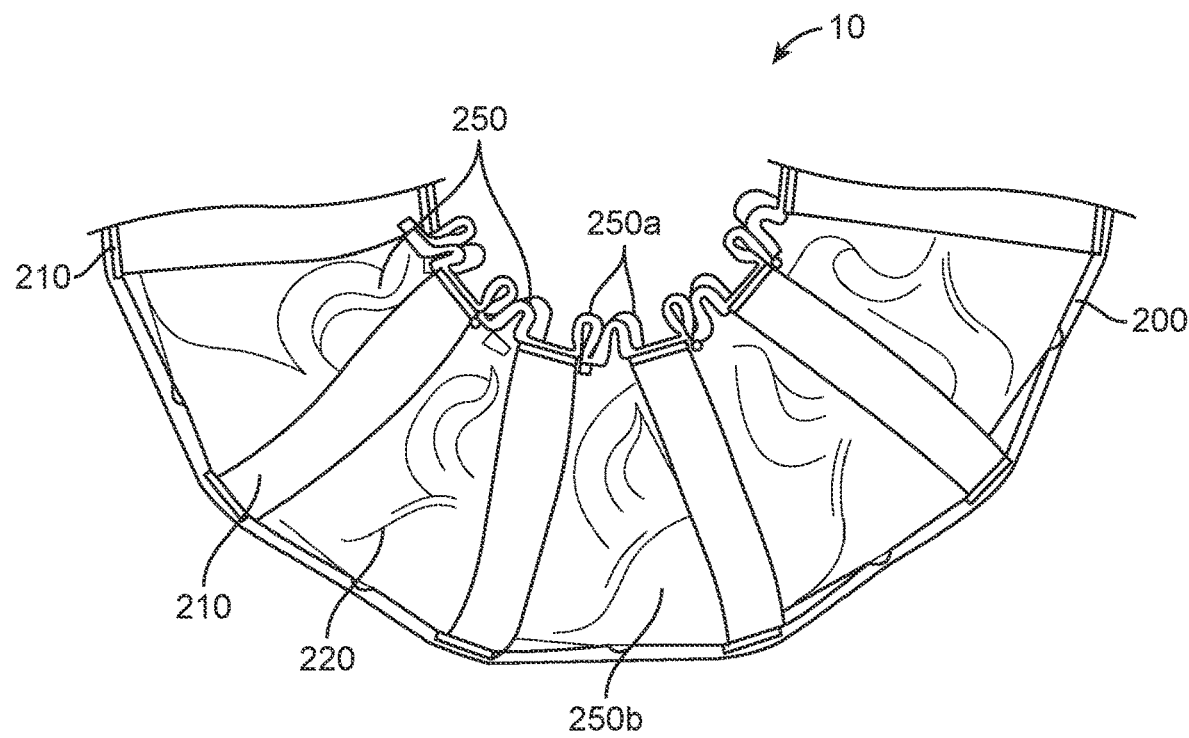
Figure 44E:
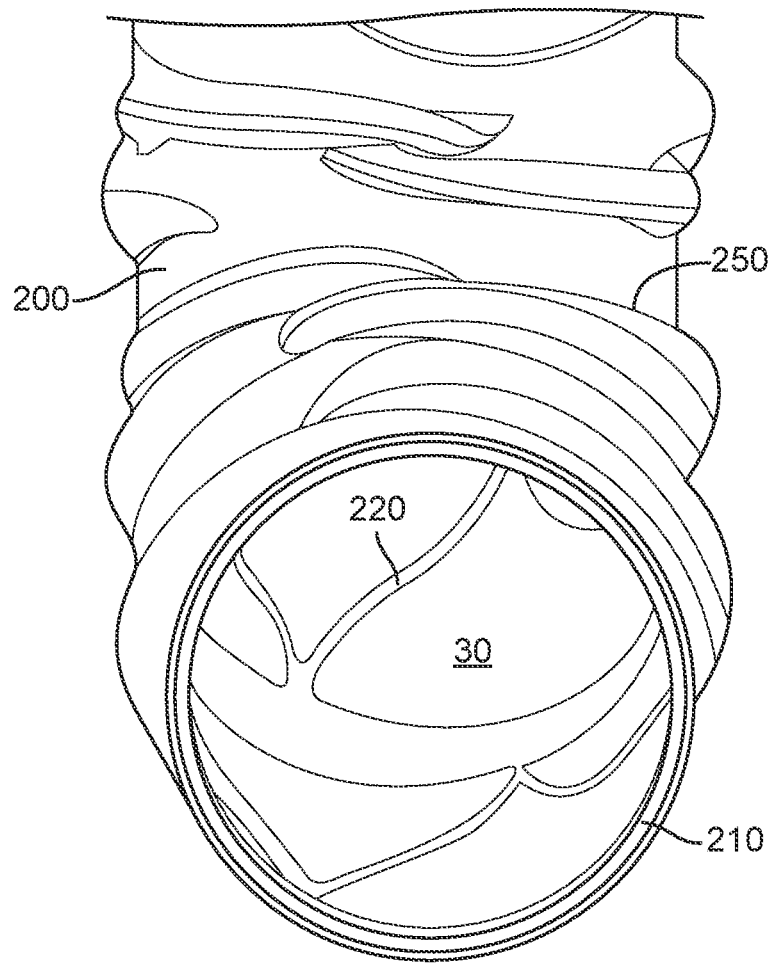

FIGS. 44A-E illustrate another tubular structure 200. Particularly, FIG. 44A illustrates the tubular structure 200 in a relaxed configuration, FIGS. 44B-44C illustrate the tubular structure 200 in a longitudinally stretched configuration and FIGS. 44D-44E illustrate the tubular structure 200 in a curved or bent configuration. The tubular structure 200 is similar to that of FIG. 43, except that the tubular structure 200 of FIGS. 44A-E comprises ring elements 210 having a constant width W8. The tubular structure 200 of FIGS. 44A-E further comprises connecting members 220 and filler 250.

As shown in FIG. 44A, the tubular structure 200 has a plurality of connecting members 220 (e.g., three pairs of connecting members 220a/220b) between respective ring elements 210. The ring elements 210 comprise a width W8 in a range of 0.1 to 1.0 mm. In some embodiments, the number of connecting members 220 and the width W8 may vary. Such variations may depend on the needs and requirements of the catheter 10.

Each connecting member 220 includes a first member end 232, a second member end 234 opposite from the first member end 232, and a member body 236 extending between the first member end 232 and the second member end 234. Each connecting members 220 from their respective first member end 232 to the second member end 234 have an arcuate configuration, such that a pair of connecting members (e.g., 220a, 220b) form a V-shaped furcular or parenthesis-like configuration, as shown in dashed-line in FIG. 44A. The arcuate configuration of the connecting members 220 allow longitudinal stretching and further degrees of freedom to the connecting members 220 when the tubular structure 200 is longitudinally stretched, translated, bent, or moved. Further, the arcuate configuration of the connecting members 220 avoids or minimizes relative rotation of adjacent ring elements 210.

When the tubular structure 200 is longitudinally stretched and subjected to tensile loads, the connecting members 220 stretched out of their arcuate configuration, such that the pair of connecting members 220a, 220b form a triangle-like loading configuration with their respective ring element 210, as shown in dashed-line in FIG. 44B. The triangle-like loading configuration of the stretched connecting members 220 and ring elements 210 with the filler 250, allow for tensile load sharing between the tubular structure 200 and the filler 250 avoiding or minimizing compression of the tubular structure 200 (e.g., collapsing of the catheter). FIG. 44C illustrate a down-the-barrel view of the longitudinally stretched tubular structure 200 of FIG. 44B, where the lumen 30 is opened (e.g., no collapsed catheter maintaining patency of the lumen).

FIGS. 44D-44E illustrate the tubular structure 200 in a curved configuration when subjected to bending loads. The composite interaction of the tubular structure 200 and the filler 250 increases bending load sharing between the tubular structure 200 and the filler 250, allowing the filler 250 to compress (e.g., wrinkle filler 250a in the inner curvature) and to expand (e.g., stretched filler 250b in the outer curvature), as shown in FIG. 44D. The composite interaction of the tubular structure 200 and the filler 250 during bending is configured to avoid or minimize kinking of catheter 10 when subjected to bending loads. FIG. 44E illustrate a down-the-barrel and perspective view of the curved tubular structure 200 of FIG. 44D, where the lumen 30 is opened (e.g., no collapsed catheter maintaining patency of the lumen).

Figure 45A:
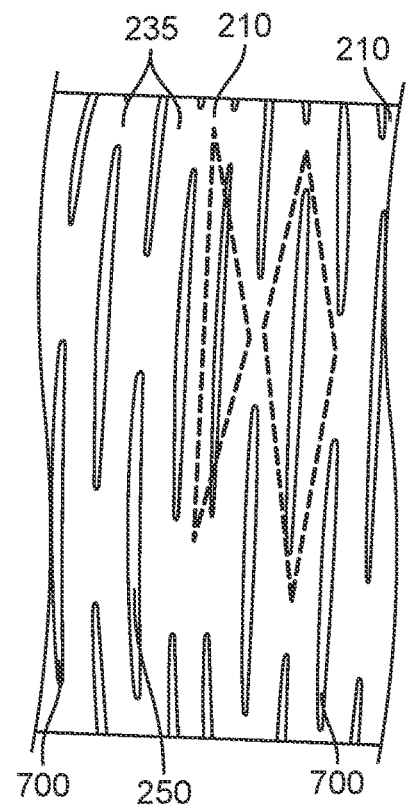
FIGS. 45A-45B illustrate another tubular structure having a cut pattern and loading configuration.
Figure 45B:
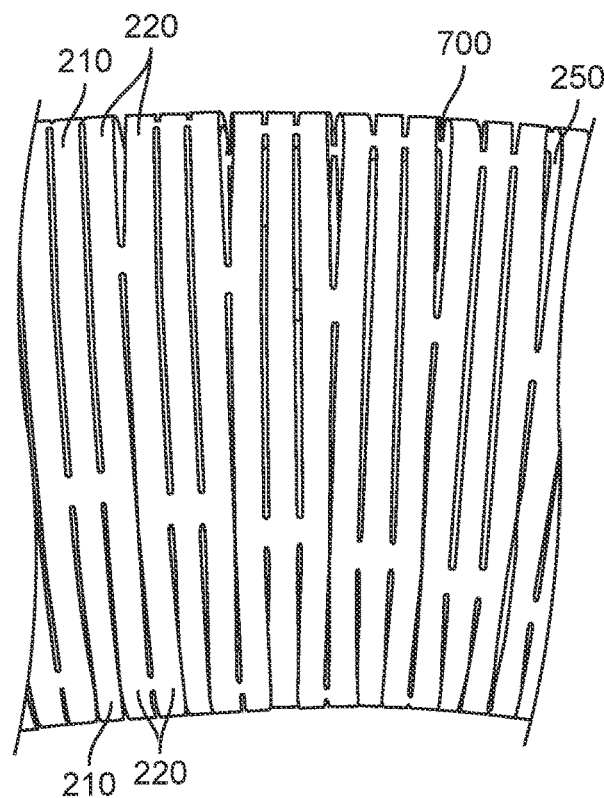

FIGS. 45A-45B illustrate yet another tubular structure 200. FIGS. 45A-45B depict a pattern of cuts made in the tubular structure 200 similar to FIG. 25, FIG. 35A, and/or FIG. 36A, wherein the cuts are created in a sinusoidal wave pattern forming interrupted articulation sections 235 between ring elements 210 in the tubular structure 200. The cut pattern made in the tubular structures 200 creates slits 700 (e.g., kerfs, slots or their like). The sinusoidal wave cuts of FIGS. 45A-45B create a ratio of at least 1:4 of ring elements 210 to connecting members 220, such as, forming a tubular structures 200 having a ring element 210 every five slits 700.

When the tubular structure 200 is longitudinally stretched and subjected to tensile loads, the connecting members 220 form alternating triangle and diamond loading configurations with their respective ring element 210, as shown in dashed-line in FIG. 45A. The triangle and diamond loading configuration of the connecting members 220 and ring elements 210 along with the filler 250, allow for tensile load sharing between the tubular structure 200 and the filler 250 avoiding or minimizing compression of the tubular structure 200 (e.g., collapsing of the catheter).

Figure 46A:
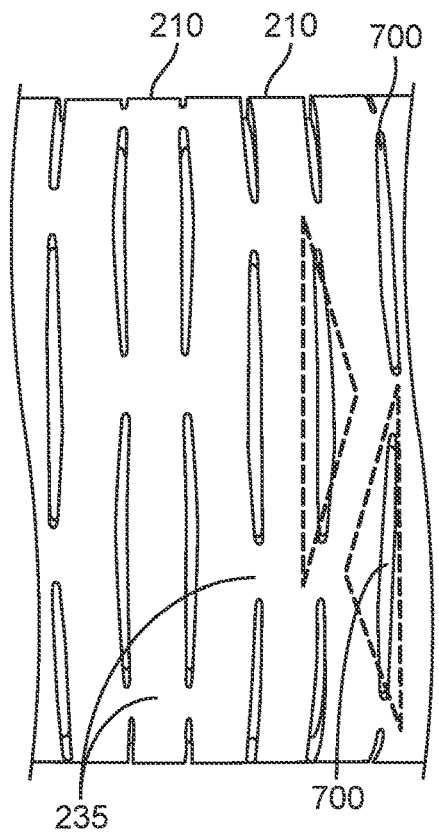
FIGS. 46A-46B illustrate a tubular structure having another cut pattern and loading configuration.
Figure 46B:
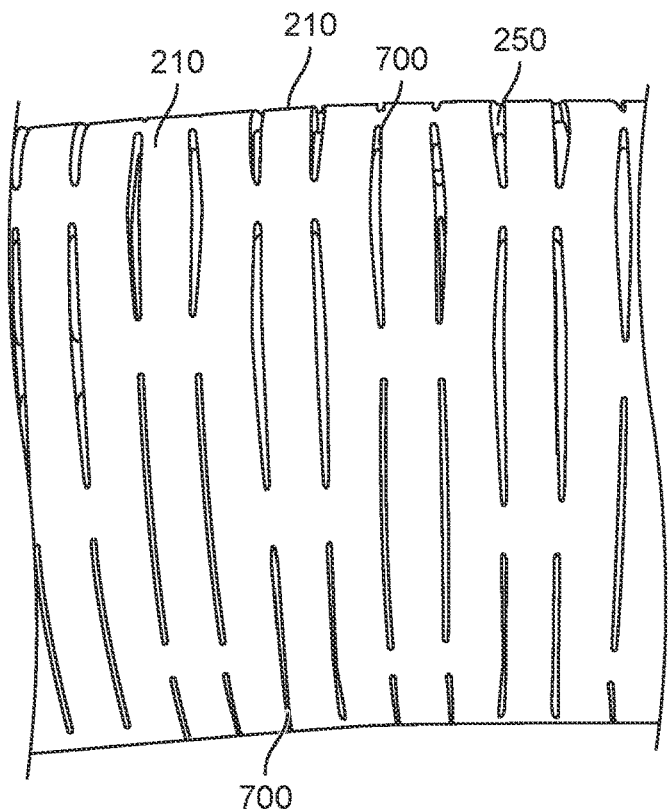

FIGS. 46A-46B illustrate another tubular structure 200. FIGS. 46A-46B depict a pattern of cuts made in the tubular structure 200 similar to FIGS. 45A-45B having interrupted articulation sections 235 between ring elements 210 in the tubular structure 200. The cut pattern made in the tubular structures 200 of FIGS. 46A-46B creates slits 700 (e.g., kerfs, slots or their like) forming a tubular structure 200 having a ring element 210 every two slits 700.

When the tubular structure 200 of FIGS. 46A-46B is longitudinally stretched and subjected to tensile loads, the connecting members 220 form triangle loading configurations with their respective ring element 210, as shown in dashed-line in FIG. 46A. The triangle loading configurations of the connecting members 220 and ring elements 210 along with the filler 250, allow for tensile load sharing between the tubular structure 200 and the filler 250 avoiding or minimizing compression of the tubular structure 200.

The cut patterns of FIGS. 45A-45B and FIGS. 46A-46B are configured to balance the forces exerted in the tubular structure 200 when it translates and/or bends. Additionally, the cut patters are configured to optimize kink resistance and tensile strength of their respective tubular structures 200 and fillers 250. Depending on the slits 700 (e.g., quantity, spacing and further features of the slits) between the ring elements 210 and connecting members 220, either a combination of triangle and diamond loading configurations (FIGS. 45A-45B) or only triangle loading configuration (FIGS. 46A-46B) are formed.

The triangle loading configuration is stiffer than the diamond loading configuration. The triangle loading configuration is less flexible in bending and tension (e.g., elongation of connecting members 220 occurs when subjected to tension and bending loads). The diamond loading configuration is more flexible in bending and tension (e.g., no need for elongation of connecting members 220 when subjected to tension and bending loads).

FIGS. 47A-47C illustrate another tubular structure 500. FIG. 47A illustrates part of the pattern to produce the tubular structure 500. The pattern depicted in FIG. 47A is similar to the pattern of FIG. 38B except that the tubular structure 500 of FIGS. 47A-47C defines triangular-shaped cells 555 and comprises ring elements 510.

The tubular structure 500 comprises elongated members 520 that are arranged in crisscross configuration and ring elements 510 disposed between respective elongated members 520. The tubular structure 500 further comprises articulation sections 540 coupling the elongated members 520 to the ring elements 510, defining triangular-shaped cells 555. Adjacent articulation sections 540 of the tubular structure 500 are disposed in the same longitudinal plane, as shown in FIG. 47B (e.g., along the longitudinal axis 30).

In some embodiments, the members 520 may have a width W9 that ranges between 0.002 to 0.003 inches, the articulation sections 540 may have a width W10 that ranges between 0.005 to 0.017 inches and the ring elements 510 may have a width W11 that ranges between 0.002 to 0.003 inches, as shown in FIG. 47A. The cells 555 may have a length L4 that ranges between 0.0700 and 0.151 inches. It should be appreciated that variation and/or combinations of dimensions of the elements of the tubular structure 500 may be desired.

FIG. 47B illustrates the tubular structure 500 comprising elongated members 520, ring elements 510, articulation sections 540, all defining triangle-shaped cells 555 in a relaxed configuration and FIG. 47C illustrates bending of the tubular structure 500.

The tubular structure 500 of FIGS. 47A-47C is configured to be flexible and kink resistance during bending. Additionally, the ring elements 510 are configured to provide hoop strength, avoid or minimize ovalization of the tubular structure 500 while bending to preserve lumen patency. In some embodiments, the ring elements 510 may have the width W11 larger than 0.003 inches. In other embodiments, the width W11 of the ring elements 510 may vary along the length of the tubular structure 500. For example, the width W11 may be larger than 0.003 inches, decreasing the flexibility of the tubular structure 500 and gradually the width W11 may decrease, increasing the flexibility of the tubular structure 500. In some embodiments the width W9 of the members 520 should be similar to the width of the filler 250 to maximize tensile force. Additionally, the number of cells 555 can be varied to increase or decrease stiffness and kink of the tubular structure 500.

FIG. 48 illustrates a two-dimensional (2D) pattern of another tubular structure. In particular, FIG. 48 shows a pattern of ring elements 210 and connecting members 220 in a 2D configuration (e.g., cutting patterns on sheets of material) to form another embodiment of the tubular structure 200 (shown in FIG. 49). The connecting members 220 are disposed between adjacent ring elements 210, such as the ring elements 210a and 210b shown in FIG. 49. The connecting members 220 include first member ends 232; second member ends 234 opposite from the first member ends 232, and member bodies 236 extending between the respective first member ends 232 and second member ends 234. The member bodies 236 form an acute angle 240 (e.g., any angle that is less than 90 degrees, such as 0 degree) with respect to the ring element 210. In some cases, the angle 240 may be measured with the tubular structure 200 being "un-rolled" to a flat configuration, as in FIG. 48.

In the illustrated embodiments of FIGS. 48-49, the connecting members 220 have curvilinear configurations at their respective first member ends 232 and second member ends 234, and a rectilinear configuration at the member bodies 236. In other embodiments, the bodies 236 may each have a curvilinear configuration.

The tubular structure of FIGS. 48-49 may be considered as a variation of that shown in FIG. 33. In particular, the tubular structure of FIGS. 48-49 is similar to the one disclosed in FIG. 33, except that one or more of the connecting members 200 comprise a plurality of sub-connecting members 222a-222d. In the embodiments of FIGS. 48-49, each connecting member 220 has at least four sub-connecting members 222a-222d in which their respective member bodies are substantially parallel (e.g., forming an angle that is less than 5 degrees, such as 0 degree) to each other. The cross-sectional shapes of the respective sub-connecting members 222a-222d are the same (i.e., they have the same width and thickness). In other embodiments, at least two of the sub-connecting members 222a-222d may have respective cross-sectional shapes that are different from each other (i.e., they have different widths and/or different thicknesses). Also, in other embodiments, the connecting member 220 may include more than four sub-connecting members 222 or fewer than four (e.g., three or two) sub-connecting members 222 between adjacent ring elements 210. As shown in the figure, majority parts of the respective sub-connecting members 222 are substantially parallel to each other. In other cases, majority parts of the respective sub-connecting members 222 may form acute angle with respect to each other. The sub-connecting members 222 may be parts of a structure that is cut to form the sub-connecting members 222.

The tubular structure of FIGS. 48-49 with the connecting member 220 having multiple sub-connecting members 222a-222d is advantageous over a tubular structure in which the connecting member 220 has a single elongated body.

Figure 50:
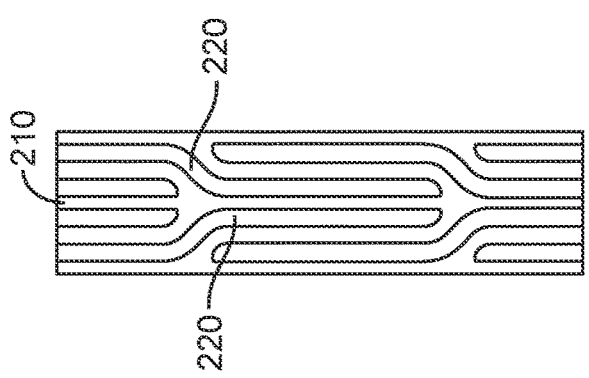
FIG. 50 illustrates another 2D pattern of a tubular structure.

FIG. 50 illustrates a 2D pattern of another tubular structure, which comprises the ring elements 210 and connecting members 220. The tubular structure of FIG. 50 is similar to that of FIG. 48, except that each connecting member 220 has a single elongated body (i.e., each connecting member 220 in the tubular structure of FIG. 50 does not have multiple sub-connecting members 222 like that of FIG. 48).

Figure 52:
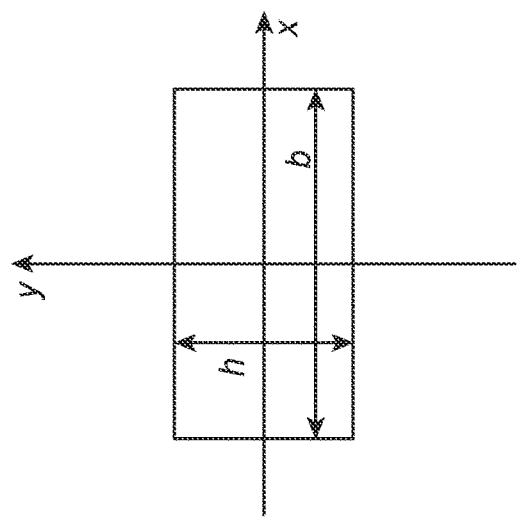
FIG. 52 illustrates a cross-sectional shape of the connecting member of FIGS. 50-51.
Figure 51:
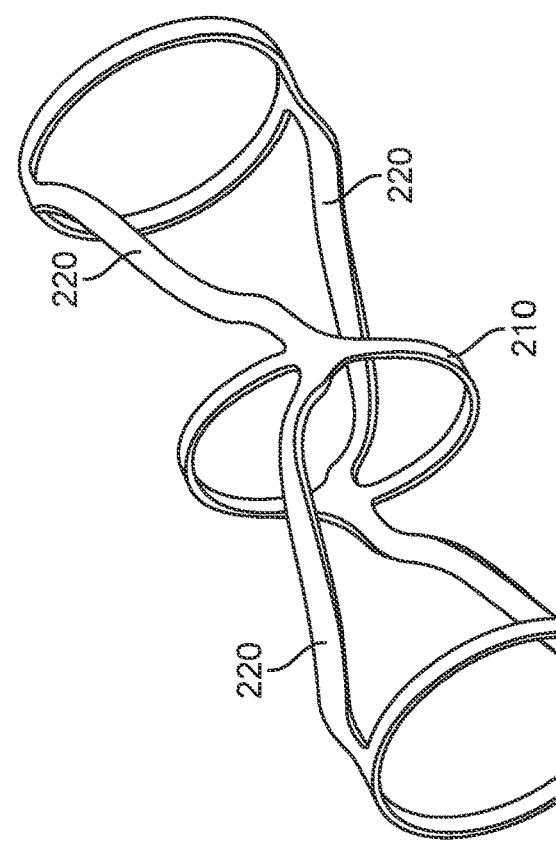
FIG. 51 illustrates the tubular structure of FIG. 50 in a stretched configuration.

In the case of FIG. 50, the tensile strength of each connecting member 220 is related to the width and wall thickness of the connecting members 220. For example, assuming the width of each connecting member 220 is b, and the wall thickness of each connecting member 220 is h (see FIG. 52), the tensile strength of the connecting member 220 is a function of the area of the cross-sectional shape, which area is b×h. If the connecting member 220 has no shear stress, the connecting member 220 can withstand a maximum tensile loading that is based on b×h. On the other hand, during use of the tubular structure, the tubular structure may undergo bending and/or twisting, which causes the connecting member 220 to twist (as shown in FIG. 51). The direction of twisting of the connecting member 220 depends on the dimensions of the thickness h and width b of the cross-sectional shape of the connecting member 220. In the illustrated example, the width b is larger than h, and the connecting member 220 twists in the manner shown in FIG. 51. The twisting imposes shear stress on the connecting members 220 and can lead to poor clinical performance such as early fracture, poor tensile performance, and/or undesirable deflected geometries of the tubular structure 200.

Figure 53:
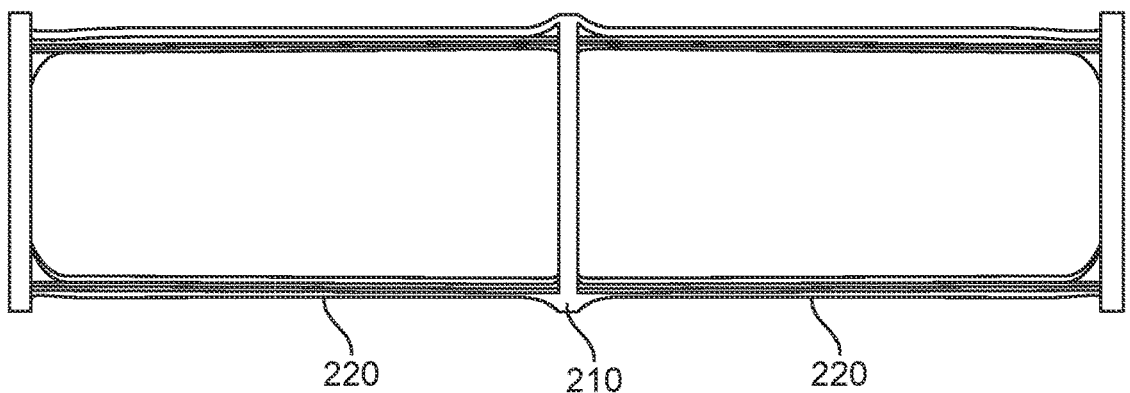
FIG. 53 illustrates the tubular structure of FIGS. 48-49 in a stretched configuration.
Figure 54:
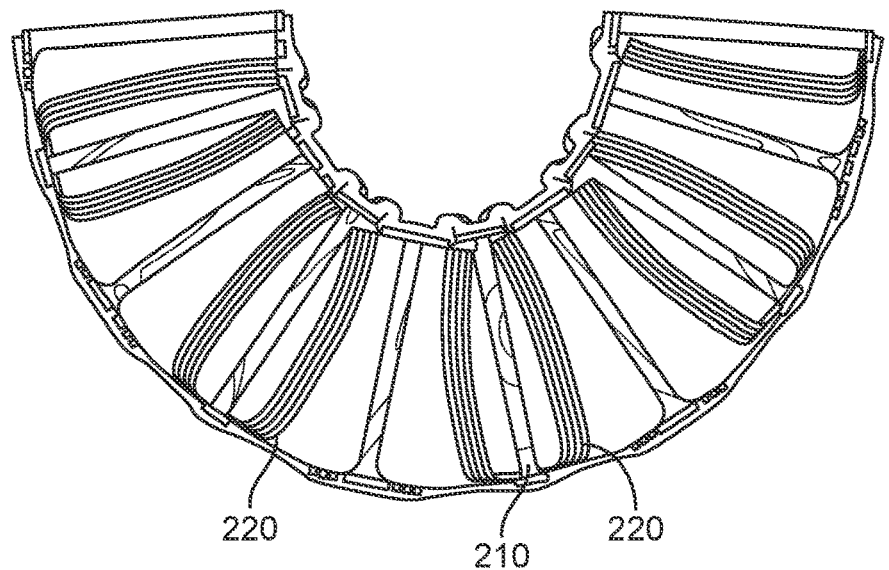
FIG. 54 illustrates a bending of the tubular structure of FIGS. 48-49.

Having the connecting members 220 comprise a plurality of sub-connecting members (e.g. 222a-222d in FIGS. 48-49) improves flexibility and pushability of the tubular structure 200 when subjected to tensile or bending forces. Also, the plurality of sub-connecting members (e.g. 222a-222d) of the connecting members 220 are configured to move (e.g., flex, bend, and/or translate) relative to the ring elements 210 in correspondence with the flexing, bending, and/or translation of the tubular structure 200, as shown in FIG. 53 and FIG. 54. The plurality of sub-connecting members (e.g., 222a-222d) eliminates or reduces the sheer stress of the connecting members 220 when the tubular member 200 is deflected, since the plurality of sub-connecting members (e.g. 222a-222d) are allowed to move (e.g., translate, slide, etc.) relative to each other. Since sheer stress is reduced or eliminated, the sub-connecting members 222 of the connecting member 220 can withstand higher tensile stress (compared to the scenario in which the connecting member 220 has no sub-connecting members 222 and has higher shear stress). Reducing shear stress in a structural member can allow the structural member to withstand higher tensile stress because the structural member's structural capacity can be utilized to handle other stress (e.g., tensile stress). For example, if a structural member has stress capacity C, the structural member can handle a combined stress (e.g., tensile stress TS, shear stress SS, etc.) that is equal to C. If shear stress SS and tensile stress TS are present, the combined stress demand on the structural member is TS+SS, and the structural member will fail when TS+SS>C. This means that the structural member can withstand tensile stress TS=C−SS. On the other hand, if shear stress is eliminated, then the structural member will fail when TS>C. In this case, the structural member can withstand tensile stress TS=C.

In addition, each sub-connecting member 222 of FIGS. 48-49 has a smaller cross-sectional width b compared to the connecting member 220 of FIG. 50. For example, the cross-section width b of the connecting member 220 of FIG. 50 may be X, and the cross-sectional width b of each of the sub-connecting members 222a-222d of FIG. 48 may be X/4. Despite the total cross-sectional area (A=4×h×X/4=hX) of all of the sub-connecting members 222 of FIGS. 48-49 being equal to the cross-sectional area (A=hX) of the connecting member 220 of FIG. 50, the combined shear stress in all of the sub-connecting members 222a-222d of the connecting member 220 of FIG. 48 is smaller than the shear stress in the connecting member 220 of FIG. 50 (given the same force-loading condition and same wall thicknesses for both devices) because the sub-connecting members 222 can move relative to each other as discussed. The plurality of sub-connecting members 222 of FIGS. 48-49 further allows the sub-connecting members 222 to collectively handle higher tensile stress (see FIG. 53) compared to the connecting member 220 of FIG. 50, because the sub-connecting members 222 have less shear stress compared to the connecting member of FIG. 50 (assuming with the same loading conditions), as discussed. The sub-connecting members 222 also increases flexibility of the tubular structure 200 as shown in FIG. 54, compared to the embodiments of FIGS. 50-51.

In the embodiments of FIGS. 48-49 and FIGS. 53-54, the wall thickness h of each sub-connecting member 222 is smaller than the width b of the connecting member 222. In other embodiments, the wall thickness h of each sub-connecting member 222 may be larger than the width b of the connecting member 222. In some cases, the thickness h is measured in a radial direction extending from a longitudinal axis of the tubular member 200. The thickness h may also be the wall thickness of the tubular member 200. In some cases, the width may be measured along a direction that is perpendicular to the radial direction.

Figure 55:
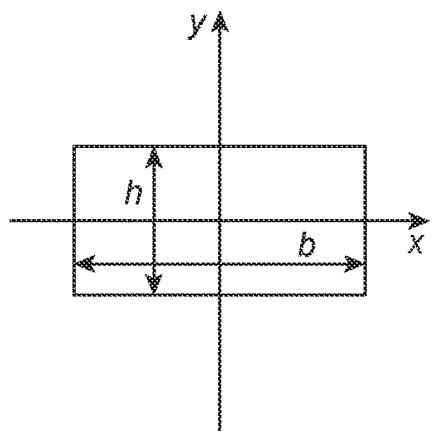
FIG. 55 illustrates a cross-sectional shape of a structural member, and associated moments of inertial with respect to two different axes.
Figure 56:
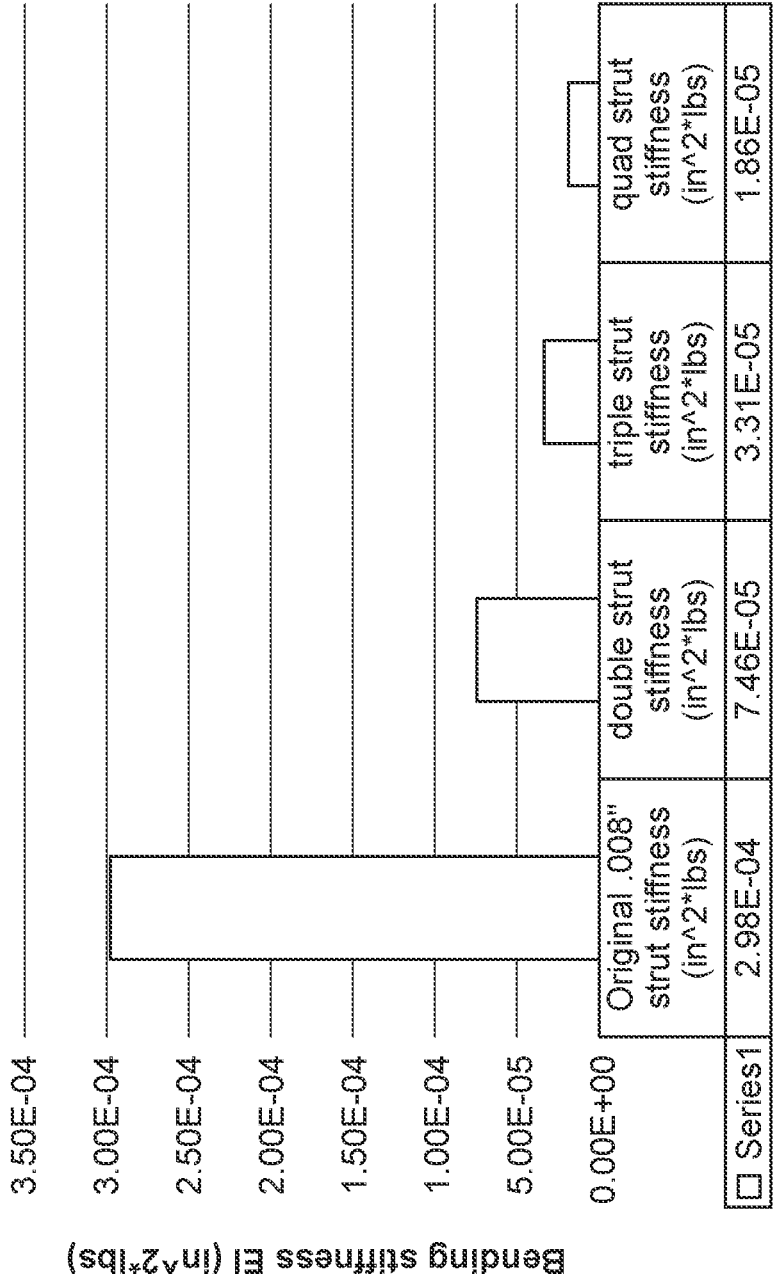
FIG. 56 is a table comparing stiffness of different connecting members.

Additionally, having the connecting member 220 comprising a plurality of sub-connecting members (e.g. sub-connecting members 222a-222d in FIGS. 48-49) allows the connecting member 220 to have reduced bending stiffness compared to the connecting member 220 in FIG. 50, because the sum of the cross-sectional stiffnesses of the sub-connecting members 222 of the connecting member 220 in FIG. 48 is less than the cross-sectional stiffness of the single connecting member 220 in FIG. 50. In particular, the bending stiffness of a member is based on a cross-sectional stiffness of the member, and the cross-sectional stiffness of the member is in turn based on a moment of inertia of the cross-sectional shape of the member. The moment of inertia I of the cross-sectional shape of a member is a function of the width of the member raised to the third power (see FIG. 55). For example, a connecting member 220 including two sub-connecting members 222 having a width b of 0.004" each, would have a stiffness of $K \times (0.004)^3 = K \times 6.4E-8$ per sub-member 222, where K is a constant. Thus, the total bending stiffness of the connecting member 220 with two sub-connecting members 222 is $2K \times 6.4E-8 = K \times 12.8E-8$. On the other hand, a single connecting member 220 having a width of 0.008" would have a stiffness of $K \times (0.008)^3 = K \times 51.2E-8$. Therefore, the stiffness of a connecting member 220 with two sub-connecting members 222 would be four times more flexible (i.e., less stiff) that a connecting member 220 without sub-connecting members 222 (e.g. 51.2E-8/ 12.8E-8=4). As a result, the overall structural stiffness of the tubular structure 200 can be adjusted by configuring a number of the sub-connecting members 222. Exemplary data table comparing the stiffness of a connecting member 220 (without sub-connecting members 222) to stiffnesses of connecting members 220 with double, triple or quadruple sub-connecting members 222, respectively, having the same base geometry is shown in FIG. 56.

In some embodiments, when sub-connecting members 222 are being created, such as by laser cutting, some materials may be removed by the laser. For example, if the width of the connecting member 220 is 0.008 inch, and if one laser cut is applied to the middle to create two sub-connecting members 222, each sub-connecting member 222 may have a width that is less than 0.004 inch (=0.008/2 inch). For example, the laser cut may remove a width of 0.0008 inch. In such cases, the width of each of the two sub-connecting members 222 may be (0.008–0.0008)/ 2=0.0036 inch.

In any of the embodiments of the tubular structure 200 described herein, the tubular structure 200 may be made from a raw tube. The raw tube may be a metal tube, an alloy tube, a plastic tube, a polymeric tube, or a tube made from any of other materials. The raw tube is then cut to form the ring elements 210 and connecting members 220. In such cases, the ring elements 210 and the connecting members 220 are parts of a cut tube. The cutting of the raw tube may be performed using laser cutting in some embodiments. For example, an electronic file storing geometric information (e.g., shape information, dimension information, etc.) regard the tubular structure 200 to be formed may be created. The electronic file may be provided to a processing unit of a laser cutting machine. The processing unit processes the electronic file to operate a laser cutter of the laser cutting machine to cut geometric pattern(s) defined by the information in the electronic file. In some embodiments, the laser cutting may be performed on the raw tube. In other embodiments, instead of a raw tube, a raw sheet of material may be provided, and the laser cutting may be performed on the raw sheet. After the laser cutting is performed, the cut sheet may be rolled to form the tubular structure 200. Edges (that are parallel to the longitudinal axis) of the rolled sheet may be connected together to form a closed loop tube. Other techniques involve forming the desired pattern into a sheet or a tube by chemical etching or electrical discharge machining.

In other embodiments, the ring elements 210 and the connecting members 220 may be integrally formed together. For example, a mold having a rod with protrusions on the surface of the rod may be provided. The protrusions correspond with the space 216 to be formed between the ring elements 210 and the connecting members 220. Then the material for forming the ring elements 210 and the connecting members 220 is deposited onto the mold. The material is then cured to form the ring element 210 and the connecting members 220.

In further embodiments, the ring elements 210 and the connecting members 220 may be separately formed, and are then connected to each other after they are formed. In one implementation, a plurality of ring elements 210 may be provided. Then a tubular mesh may be used to connect the ring elements 210 in series. In particular, the ring elements 210 in spaced-away configuration may be disposed over the tubular mesh, and are arranged in series along a longitudinal axis of the tubular mesh. The ring elements 210 may then be secured to the tubular mesh, such as via an adhesive, glue, weld, etc. Parts of the tubular mesh between the ring elements 210 become and function as the connecting members 220.

As discussed, the tubular structure 200 described herein may be utilized to form a tube of a catheter. For example, filler 250 may be disposed in the space (e.g., gaps) 216 between the ring elements 210 and the connecting members 220. In some embodiments, the tubular structure 200 may be dipped into a polymeric solution to allow the polymeric solution to fill the space 216. The polymeric solution may then be cured to form the filler 250. Excess filler material may be removed using agent, by cutting, sanding, etc.

Also, in some embodiments, the filler 250 occupying the space 216 may have the same thickness as the thickness of the wall of the tubular structure 200. In other embodiments, the filler 250 may be thicker than the thickness of the wall of the tubular structure 200.

In addition, in some embodiments, the material of the filler 250 may extend pass the exterior surface of the tubular structure 200. In some cases, the material of the filler 250 may be disposed on the exterior surface of the tubular structure 200 to form an outer layer covering the tubular structure 200. The outer layer may be formed integrally together with the filler 250 in the space 216. In other embodiments, the outer layer may be formed separately from the filler 250, and is disposed on the exterior surface of the tubular structure 200 after the filler 250 is disposed (e.g., formed) in the space 216. In such cases, the outer layer may be made from the same material as the filler 250, or may be made from a material that is different from the filler 250.

Similarly, in some embodiments, the material of the filler 250 may extend pass the inner surface of the tubular structure 200. In some cases, the material of the filler 250 may be disposed on the inner surface of the tubular structure 200 to form an inner layer covering the inner wall of the tubular structure 200. The inner layer may be formed integrally together with the filler 250 in the space 216. In other embodiments, the inner layer may be formed separately from the filler 250, and is disposed on the inner surface of the tubular structure 200 after the filler 250 is disposed (e.g., formed) in the space 216. In such cases, the inner layer may be made from the same material as the filler 250, or may be made from a material that is different from the filler 250.

The filler 250 is not limited to being polymeric material, and may be made from other materials in other embodiments. For example, in other embodiments, the filler 250 may be made from plastic, foam, or any of other elastic materials.

In any of the embodiments of the tubular structure 200 (or any of the further tubular structures described herein), the filler 250 and the tubular structure 200 behave as a composite by sharing tensile and bending loads between the filler 250 and tubular structure 200. The tubular structures 200 having ring elements 210 and connecting members 220 is configured to evenly distribute the loads in the filler 250, such that peak stresses (e.g., quantified by percent of elongation) in the filler 250 are minimized, which ensures higher tensile strength and resistance to rupture of the filler 250. For example, when the tubular structure 200 is elongated (e.g., in tension or in bending), the filler 250 elongation can be more evenly distributed, which allows for an effective load distribution between the filler 250 and tubular structure 200 of the catheter 10. Some of these advantages are achieved by having an angle between the connecting members 220 and the ring elements 210 that creates uniform strains in the filler 250 during elongation/bending of the tubular structure 200. The angle of the connecting members 220 relative to their respective ring elements 210 is about 10 degrees (e.g., +/−5 degrees) and can be increased or decreased to allow compliance of the filler 250 in order to match the compliance of the tubular structure 200. Further advantages of the composite effects of sharing tensile and bending loads between the filler 250 and tubular structure 200 are achieve by varying the width and/or the radius of the ring elements 210 and/or connecting members 220, such as for example, having thicker ring elements 210 avoids or minimize the bending of the rings when the catheter 10 is subjected to bending loads. Further advantages of the composite effects of sharing tensile and bending loads between the filler 250 and tubular structure 200 are achieve by varying and/or increasing the ratio of connecting members 220 to their respective ring elements 210 (e.g., ratio of connecting members per ring, such as 3:1, 4:1, 5:1, 6:1, etc.). It should be appreciated that the patterns of the tubular structures disclosed herein are produced to optimize the interaction with the filler, such that the tubular structures and the filler act in a composite, combined and compounded manner sharing tensile and bending loads. The composite interaction between the tubular structures and the filler increases tensile and bending load sharing while reducing compression of the catheter. The composite interaction between the tubular structures and the filler further increases trackability of the catheter (e.g., advancing the catheter within a body lumen without a guidewire).

In other embodiments, the catheter 10 may not include filler 250. Instead, the catheter 10 may include an outer sheath and an inner sheath, with the tubular structure 200 sandwiched there-between. Other techniques of sealing the space 216 may be employed. For example, in other embodiments, a filler may be applied to the tubular structure 200 to seal the space 216.

In addition, in some embodiments, the ring elements 210 may have the same thickness as the connecting members 220. In other embodiments, the ring elements 210 and the connecting members 220 may have different thicknesses. For example, in other embodiments, the ring elements 210 may have a first thickness, and the connecting members 220 may have a second thickness, wherein the first thickness may be larger or smaller than the second thickness.

Tube Manufacturing Processes

Various techniques may be employed to make the tube 11 having the tubular structure 200. In some embodiments, a filler may be applied so that the material is disposed in the openings of the tubular structure 200 and forms an outer layer covering the exterior surface of the tubular structure 200. The filler and tubular structure 200 forms the tube 11. In other embodiments, the filler may encapsulate the tubular structure 200 to form the tube 11. In such cases, the filler covers the exterior surface of the tubular structure, covers the interior surface of the tubular structure, as well as filling the openings (e.g., slots, kerf, slits) through the wall of the tubular structure 200.

In some embodiments, the filler forming part of the tube 11 may have a modulus of elasticity that is lower than the modulus of elasticity of the tubular structure 200. For example, the filler may have a modulus of elasticity that is less than 50%, or more preferably less than 30%, or more preferably less than 20%, or more preferably less than 10%, or more preferably less than 5%, or more preferably less than 1%, of that of the tubular structure 200. In one implementation, the filler may have a modulus of elasticity that is less than 15 Mpa (e.g., 10 Mpa or less).

Also, the filler forming part of the tube 11 may have the ability to undergo significant elongation before break point. For example, in some embodiments, the filler may be capable of having a strain (defined as an amount of elongation of the material divided by the length of the material) of at least: 20%, 40%, 60%, 80%, 100%, 200%, 300%, 400%, 500%, 600%, 700%, 800%, 900%, 1000%, or greater.

Various materials may be utilized as the filler material. The filler may be made from polymer, plastic, foam, polymeric solution or any of other elastic materials. By means of non-limiting examples, the filler material may include polyurethane, polyurethane-based material, silicon-based material, any material having polyurethane dispersion or silicon-based dispersion, etc. Examples of filler material that may be used include CD102® or AD111® from Covestro, Gelest Ex-sil50® from Gelest, etc.

In some embodiments, because the filler is significantly softer than the material of the tubular structure 200, the resulting tube 11 will have one or more mechanical properties that are contributed predominantly (e.g., more than 50%, more than 60%, more than 70%, more than 80%, more than 90%, more than 95%, more than 99%, etc.) by the tubular structure 200. By means of non-limiting examples, the one or more mechanical properties may be a bending stiffness, an axial stiffness, a torsional stiffness, shear stiffness, or any combination of the foregoing.

In one or more embodiments, the tube 11 may optionally further include a lubricious coating (e.g., hydrophilic or any other suitable coating) that is disposed on the exterior surface of the tube 11 and/or on the interior surface of the tube 11. In some cases, an initial coating material may first be applied on the tubular structure 200 to fill the openings at the wall of the tubular structure 200, and optionally to cover the exterior and/or interior surface of the tubular structure 200. Then the lubricious coating is applied over the initial coating material.

Constructing the tube 11 using the tubular structure 200 (providing a majority of the mechanical properties), and using the very soft filler, is advantageous because it prevents the distal end of the tube 11 from being too stiff, and because it allows design of catheter to be easier with resulting behavior of the catheter being more predictable (because computational modeling of the catheter may be made based on the tubular structure design only).

Various techniques may be employed to apply the filler to the tubular structure 200 in different embodiments. For example, in some embodiments, a deposition technique may be employed to deposit the filler onto the tubular structure 200. In other embodiments, a dipping process may be utilized to apply the filler onto the tubular structure 200.

Dipping Process

In some embodiments, when using a dipping technique to apply the filler onto the tubular structure 200, a barrier may be provided inside the central lumen of the tubular structure 200 to prevent the filler from entering into the central lumen. For example, in some embodiments, the interior surface of the tubular structure 200 may be masked to prevent the filler from outside the tubular structure 200 from flowing into the central lumen through the openings at the wall of the tubular structure 200. In other embodiments, a tube or rod may be placed inside the central lumen of the tubular structure 200 to act a barrier for preventing the filler from entering into the central lumen. The tube or the rod may be made from PTFE, HDPE, stainless steel, or any of other suitable materials.

The tubular structure 200 may then be placed into a reservoir of the filler in liquid or viscous form. The filler may be tailored to have certain specific viscosity to assist with the filler/coating process. In some cases, the tubular structure 200 may be placed vertically into the reservoir with the longitudinal axis of the tubular structure 200 forming an angle that is 90°+/−25° with respect to a top surface of the liquid in the reservoir. In other cases, the tubular structure 200 may be placed horizontally into the reservoir with the longitudinal axis of the tubular structure 200 forming an angle that is 0°+/−25° with respect to a top surface of the liquid. In other embodiments, the tubular structure 200 may be placed into the reservoir at other angles that are different from the above examples.

In some embodiments, the tubular structure 200 may be inserted into the reservoir at a certain rate, such as anywhere from 0.01 cm/sec to 5 cm/sec. In other embodiments, the tubular structure 200 may be inserted at a rate that is slower or faster than the above range of rates. Also, in some embodiments, as the tubular structure 200 is inserted into the reservoir, the tubular structure 200 may be rotated at a certain rate, such as 2-10 rotations per minute. The rotational speed may be slower or faster than 2-10 rotations per minute in other embodiments. In further embodiments, the tubular structure 200 may not be rotated as it is being inserted into the reservoir.

After the tubular structure 200 is dipped into the reservoir of the filler, the tubular structure 200 may then be removed from the reservoir. In some embodiments, the tubular structure 200 may be removed from the reservoir at a certain rate, such as anywhere from 0.01 cm/sec to 10 cm/sec. In other embodiments, the tubular structure 200 may be removed from the reservoir at a rate that is slower or faster than the above range of rates. Also, in some embodiments, as the tubular structure 200 is removed from the reservoir, the tubular structure 200 may be rotated at a certain rate, such as 2-10 rotations per minute. The rotational speed may be slower or faster than 2-10 rotations per minute in other embodiments. In further embodiments, the tubular structure 200 may not be rotated as it is being removed from the reservoir of the filler.

As a result of dipping the tubular structure 200 into the reservoir and removing it from the reservoir, a first layer of filler is disposed on the exterior surface of the tubular structure 200. The filler also spans and fills up the openings at the wall of the tubular structure 200.

After the tubular structure 200 is removed from the reservoir, the tubular structure 200 with the filler is held at certain time and at certain temperature to solidify the filler. The time for the filler to solidify may be anywhere from 1 minute to 120 minutes. In other embodiments, the solidifying time may be faster than 1 minute, or longer than 120 minutes. Also, in some embodiments, the temperature for solidifying the filler may be anywhere from 20° C. to 100° C. In other embodiments, the temperature for solidifying the filler may be less than 20° C. or higher than 100° C.

In some embodiments, the insertion of the tubular structure 200 into the reservoir, and the removing of the tubular structure 200 from the reservoir, may be repeated one or more times (e.g., anywhere from 1 additional time to 30 additional times, or more) until a desired thickness for the filler is achieved. In some embodiments, the thickness of the filler created on the exterior surface of the tubular structure 200 may be anywhere from 0.0001 inch to 0.003 inch, or greater.

In some embodiments, the applying of the filler onto the tubular structure 200 may be performed in a vacuum. For example, in some embodiments, the reservoir of filler may be placed in a vacuum chamber, and the dipping and removing of the tubular structure 200 may be performed inside the vacuum chamber. The solidifying of the filler may also occur inside the vacuum chamber.

In some embodiments, after the filler is solidified, a hydrophilic coating may be applied on the solidified coating. The application of the hydrophilic coating may be performed using a dipping technique that is similar to that described above. In other embodiments, the hydrophilic coating may be applied on the solidified coating using a deposition technique. The hydrophilic coating may be applied to the exterior surface of the tube 11 and/or to the interior surface of the tube 11. In some cases, the hydrophilic coating may be considered to be a part of the tube 11.

It should be noted that the processing of coating the tubular structure 200 is not limited to the examples described above, and that the tubular structure 200 may be coated using other techniques, or variations of the techniques described. For example, in other embodiments, a barrier may not be provided inside the central lumen of the tubular structure to prevent the filler from entering into the central lumen. Instead, filler is allowed to flow into the central lumen during the dipping process. In such case, after the tubular structure 200 is removed from the reservoir, and before the filler in the central lumen of the tubular structure 200 solidifies, a plunger may be placed inside the central lumen and be moved longitudinally through the tubular structure 200 to remove excess material inside the central lumen. In some embodiments, all filler inside the central lumen is removed so that there is no filler disposed on the interior surface of the tubular structure 200. In other embodiments, some but not all of the filler inside the central lumen is removed so that a layer of the filler remains on the interior surface of the tubular structure 200. In further embodiments, the removing of the excess filler inside the central lumen of the tubular structure 200 may be removed using a cutter after the filler has been solidified.

In other embodiments, before the tubular structure 200 is inserted into the reservoir of filler, a rod or a tube (smaller than a size of the central lumen of the tubular structure 200) may be placed inside the central lumen of the tubular structure 200. The rod or the tube has an exterior surface that is spaced away from the inner surface of the tubular structure 200. This allows the filler to fill the space between the rod/tube and the interior surface of the tubular structure 200, thereby creating a layer of coating on the interior surface of the tubular structure 200. The filler also fills the openings at the wall of the tubular structure 200, and extends to outside the tubular structure 200 to create a layer of coating on the exterior surface of the tubular structure 200.

In further embodiments, instead of using the dipping technique, the filler may be pumped to encapsulate the tubular structure 200 at certain flow rates to create a desired thickness of the coating.

Thermal Process

Alternative techniques may be employed to apply the filler to the tubular structure 200 in different embodiments. In some embodiments, thermal recovery and/or expansion properties of polymeric material (e.g., stretched or non-stretched fluoropolymers) may be used to create an integral polymer or fluoropolymer filler for the tubular structure 200.

In some embodiments, the filler may be implemented using one or more layers that encapsulate the tubular structure 200 to form the tube 11. In such cases, the layer(s) may cover the exterior surface of the tubular structure 200 defining the outer surface 21, may cover the interior surface of the tubular structure 200 defining the inner surface 22, and may fill the openings (e.g., slots, kerf, slits) through the wall of the tubular structure 200. In this embodiment, the layer(s) may be composed of one or more of the materials previously disclosed. In other embodiments, the filler may be implemented using one or more layers that cover the exterior surface of the tubular structure 200 (not the interior surface of the tubular structure 200). In such cases, the material of the layer(s) may or may not fill the openings through the wall of the tubular structure 200. In further embodiments, the filler may be implemented using one or more layers that cover the interior surface of the tubular structure 200 (not the exterior surface of the tubular structure 200). In such cases, the material of the layer(s) may or may not fill the openings through the wall of the tubular structure 200.

In other embodiments, different materials may be used for the filler. For example, in other embodiments, the exterior surface of the tubular structure 200 may be covered using a first material (e.g., Pebax) to form the outer surface 21 or jacket); the interior surface of the tubular structure 200 may be covered using a second material (e.g., PTFE) to form the inner surface 22 or liner, wherein the liner and/or jacket may fill the openings (e.g., slots, kerf, slits) through the wall of the tubular structure 200.

Figure 57A:
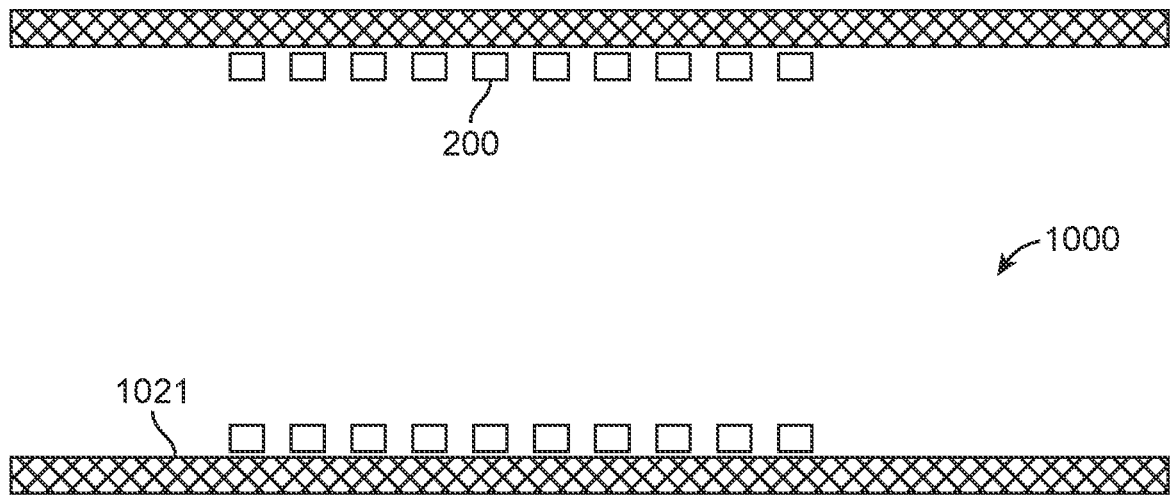
FIGS. 57A-57F illustrate cross-sectional views of a method of manufacturing the catheter of FIG. 1.
Figure 57B:
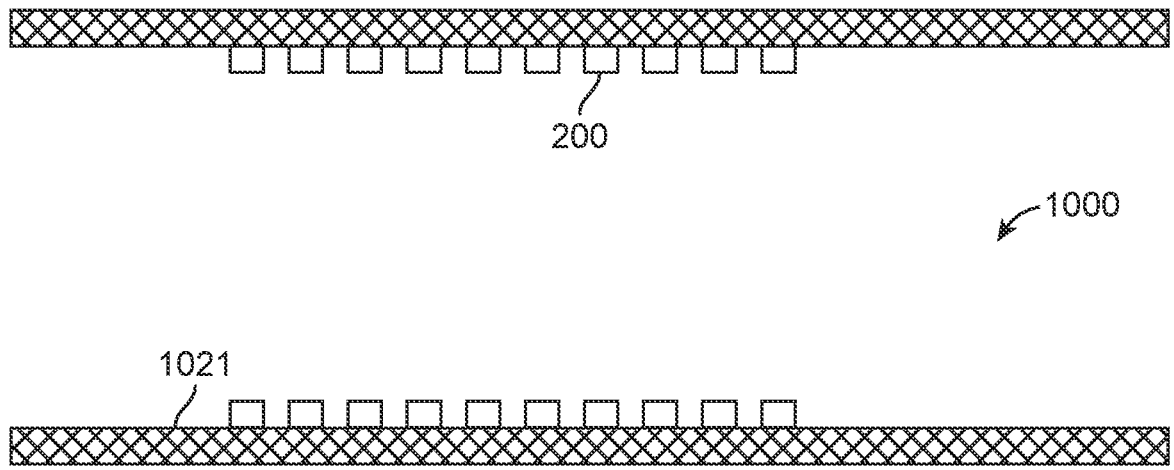

Referring now to FIGS. 57A-57F, a method 1000 of manufacturing the tube 11 using a thermal process that forms an integral polymeric (e.g., fluoropolymer or other polymer) filler for the tubular structure 200, will be described. FIGS. 57A-57F illustrate the method depicting cross-sectional view of the tubular structure 200, filler and other elements, comprising the followings steps: First, a heat-shrink tube 1021 is disposed over the tubular structure 200 (FIG. 57A). The heat-shrink tube 1021 may be composed of FEP, PFA, PVDF, or any other non-PTFE polymeric material. In other embodiments, the heat-shrink tube 1021 may be composed of PTFE polymeric material. The heat-shrink tube 1021 may have a central lumen with a cross-sectional dimension that is larger than the outer cross-sectional dimension of the tubular structure 200. Then, the heat-shrink tube 1021 is heated such that the heat-shrink tube 1021 contacts the outer surface 21 of the tubular structure 200 to form a jacket (FIG. 57B).

Figure 57C:
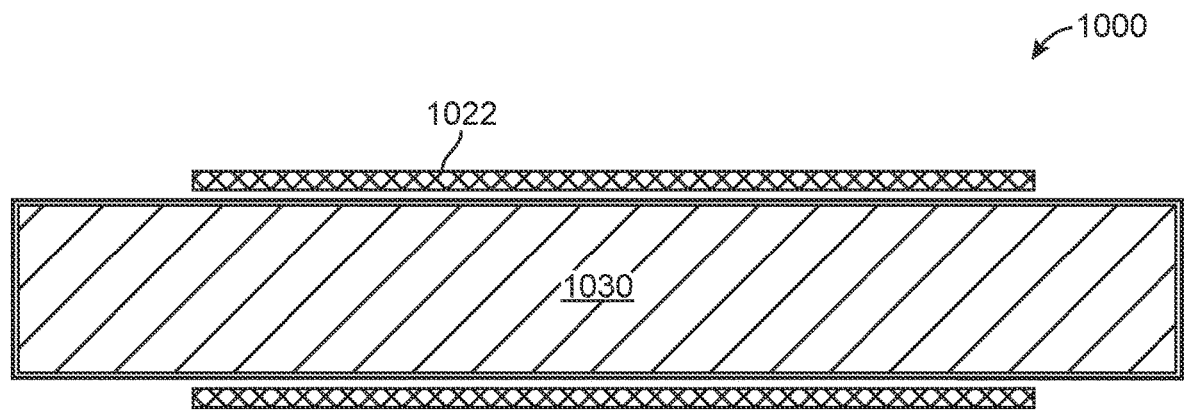
Figure 57D:
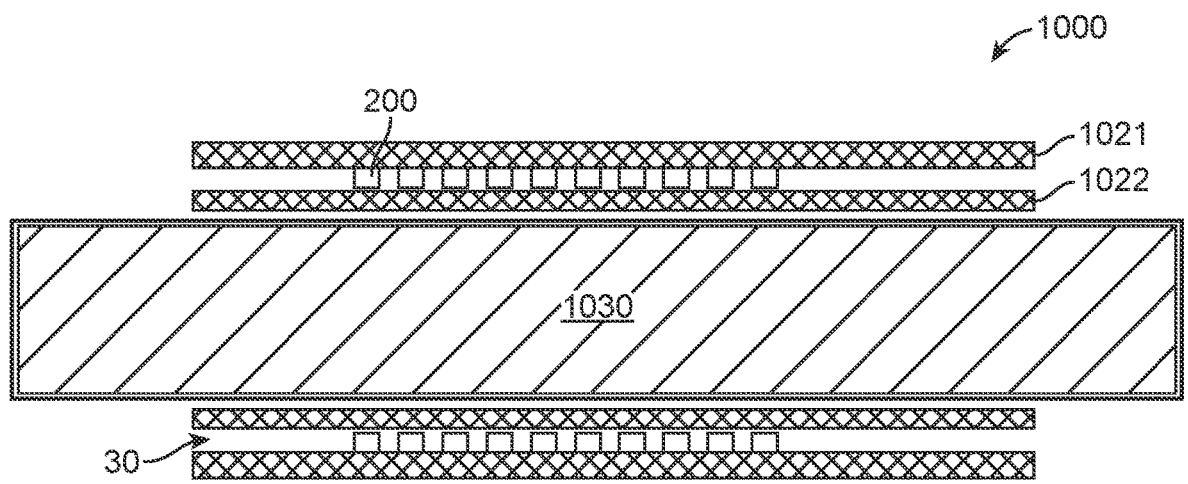

Before, during or after the steps of FIGS. 57A-57B, a tube 1022 may be inserted into the tubular structure 200 for implementing a liner for the tubular structure 200. For example, as shown in FIG. 57C, in some embodiments, the tube 1022 may be inserted over a barrier rod 1030, and the barrier rod 1030 and the tube 1022 may then be inserted into the tubular structure 200 (FIG. 57D). The barrier rod 1030 may be a tube, a cylinder, or the like. The barrier rod 1030 may be composed of any material, such as, PTFE. The barrier rod 1030 is configured to prevent any material from entering into the lumen 30 of the tubular structure 200. In some embodiments, the barrier rod 1030 and/or the tube 1022 may be stretched before being inserted into the tubular structure 200. In one implementation, the barrier rod 1030 and the tube 1022 may be stretched at room temperature (approximately 22° C.). The barrier rod 1030 and the tube 1022 may be stretched together after the tube 1022 is disposed over the barrier rod 1030. Alternatively, the barrier rod 1030 may be stretched first, then the tube 1022 is disposed over the stretched barrier rod 1030, and the tube 1022 is then stretched. In further alternative, the barrier rod 1030 may be stretched, and the tube 1022 may be stretched, and then the stretched tube 1022 is disposed over the stretched barrier rod 1030. In other embodiments, the stretching of the barrier rod 1030 and/or the stretching of the tube 1022 is not required. The tube 1022 may be made from any suitable material, such as a non-PTFE polymer.

Figure 57E:
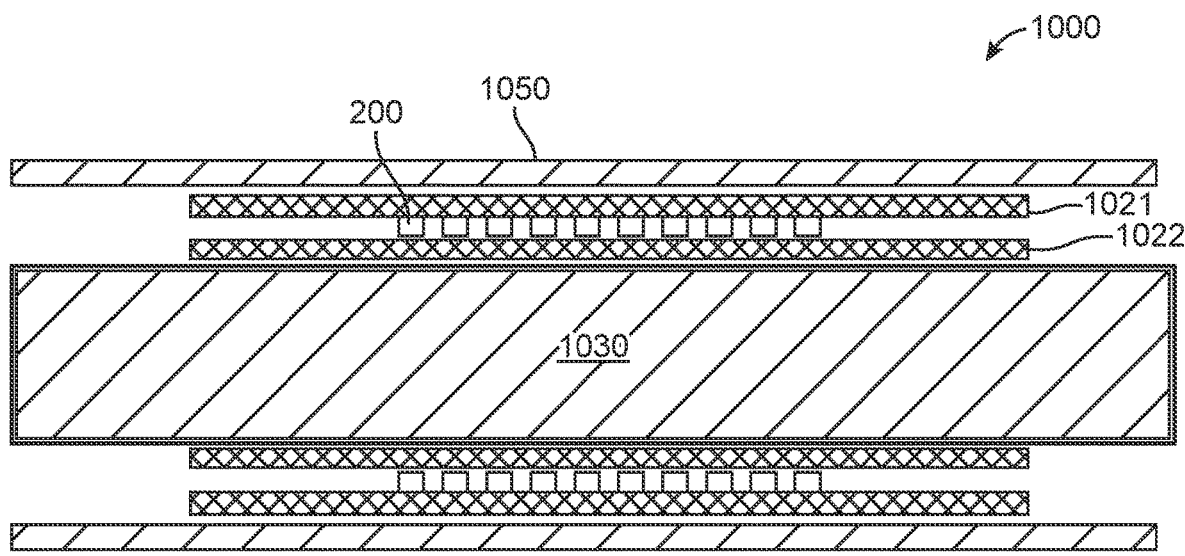
Figure 57F:
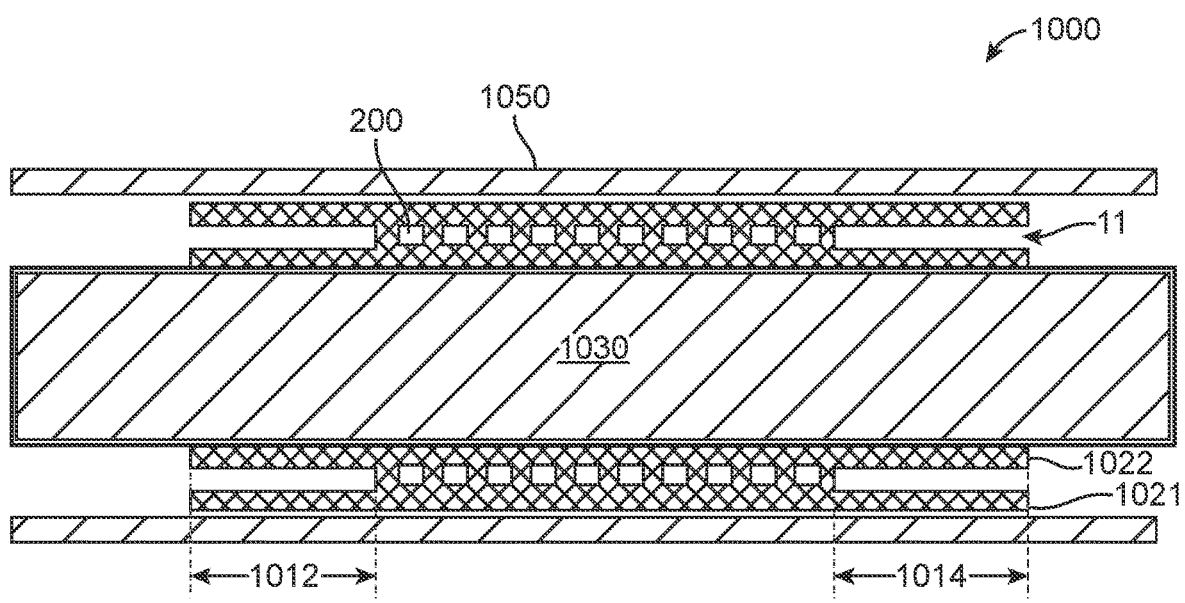

Next, referring to FIG. 57E, a heat-shrink tubing 1050 may be disposed over the heat-shrink tube jacket 1021. Then, all of the elements previously described and depicted in FIG. 57E are heated (e.g., to a temperature that is above room temperature), As a result of the heating, the barrier rod 1030 expands to compress the liner 1022 towards the inner surface of the tubular structure 200. As a result of the heating and compression, the liner 1022 and heat-shrink tube jacket 1021 melt into the openings of the tubular structure 200, fusing the liner 1022 and the jacket 1021 through the openings of the tubular structure 200 (FIG. 57F). In this embodiment, the filler comprises the fused liner 1022 and jacket 1021. In some embodiments, in order to prevent air bubbles between the liner 1022 and the jacket 1021, the heating may optionally be performed by a localized heat source traveling from one end of the liner 1022/jacket 1021 to the other end, or the heating may be performed in a vacuum chamber (not shown). In some embodiments, the heating may be performed by a heat source that is a part of a laminator.

After the filler is formed in the openings of the tubular structure 200, the heat-shrink tubing 1050 is removed (e.g., stripped from the outer surface 21 of the tubular structure 200), and the barrier rod 1030 is removed (e.g., by pulling or pushing it out from the inner surface 22 of the tubular structure 200, and optionally also by stretching the barrier rod 1030 before pulling or pushing it). As a result, the tubular structure 200 is encapsulated by the liner 1021 and the jacket 1022, and the openings of the tubular structure 200 is filled with liner materials that are composed of material of the liner 1021, material of the jacket 1022, or both.

In the above embodiments using the barrier rod 1030, it should be appreciated that when the barrier rod 1030 that is disposed within the lumen of tubular structure 200 is heated, the barrier rod 1030 expands to occlude the central lumen of the tubular structure 200. Expansion of the barrier rod 1030 also compresses the liner 1022 against the inner surface of the tubular structure 200, covering the openings at the wall of the tubular structure 200. This technique is insensitive to the dimension of the openings at the wall of the tubular structure 200, to the thickness of the liner, and/or tolerances of the cross-sectional dimensions of the various components. Therefore, there is no need to accommodate tolerance stack up, and the inner diameter (ID) of the lumen of the tube 11 (e.g., catheter) may be maximized.

Additionally, the step of heating the barrier rod 1030 and/or heat-shrink tubing 1050 (as shown in FIG. 57F) is advantageous because it ensures intimate contact and secure fusion between the liner 1022, the tubular structure 200, and outer jacket 1021, forming the tube 11.

In some embodiments, the end portions (e.g., distal end 1012 and/or proximal end 1014 of FIG. 57F) of the tube 11 may be trimmed, cut or reduced as desired. In other embodiments, the method 1000 may be applied to discrete portions or sections of the tubular structure 200 to create band or markers. In some embodiments, the method 1000 may be applied with a variety of materials and/or width of materials allowing variations on flexibility and/or stiffness at different sections of the tube 11

In some embodiments, the liner 1022 and the jacket 1021 may be formed of respective materials having lower melting temperature(s) than the material of the barrier rod 1030 and the material of the heat-shrink tubing 1050, allowing the liner 1022 and the jacket 1021 to melt and/or fuse prior any melting of the barrier rod 1030 and the heat-shrink tubing 1050. For example, in some embodiments, the liner 1022 and the jacket 1021 may be formed of respective non-PTFE materials (e.g., FEP, PFA, PVDF or any other suitable polymer), the barrier rod 1030 may be formed of a PTFE material, and the heat-shrink tubing 1050 may be formed of a PTFE material, wherein the non-PTFE material of the liner 1022 and the non-PTFE material of the barrier rod 1030 may have lower melting temperature(s) than the PTFE barrier rod 1030 and the PTFE heat-shrink tubing 1050. In some cases, FEP melting point is 260° C., PFA melting point is 306° C., PVDF melting point is 177° C., and PTFE 'melting' point is 327° C.

It should be appreciated that the steps of manufacturing described herein may be performed simultaneously or sequentially, as suitable, and not necessarily in the order previously described.

In an alternative embodiment of the method 1000 of manufacturing the tube 11, the steps are similar as those described with reference to FIGS. 57A-57F, except that the liner 1022 (shown in FIG. 57C) includes an outer layer configured to adhere to an inner surface of the tubular structure 200. In some cases, the outer layer of the liner 1022 is heat and/or compression activated, such that when the liner 1022 is heated and/or compressed towards the tubular structure 200, the outer layer secures the liner 1022 relative to the tubular structure 200. In some embodiments, the outer layer of the liner 1022 may be made from non-PTFE polymer. In other embodiments, the outer layer of the liner 1022 may be made from PTFE polymer. Also, other part(s) of the liner 1022 may be made from non-PTFE polymer or PTFE polymer.

Also, in other embodiments, the tube 11 may be formed without having the jacket 1021, such that the liner 1022 would form the filler of the tubular structure 200. In further embodiments, a coating may be applied over the outer diameter (OD) of the tubular structure 200 without the jacket 1021. For example, a Parylene coating chamber may apply conformal Parylene (e.g., Parylene C) to create a uniform conformal layer on the OD of the tubular structure 200, extending across the openings of the tubular structure 200. In some cases, material of the conformal layer may migrate towards the liner 1022, and may attach to the liner 1022. Also, in some embodiments, material of the conformal layer may attach the liner 1022 to the tubular structure 200.

In further embodiments, if the liner 1022 is provided, the liner 1022 may be non-stretched (i.e., the step of stretching the liner 1022 may be omitted). In such cases, the non-stretched liner 1022 may be disposed within the tubular structure 200. The liner 1022 may then be heated to expand the liner 1022 so that it contacts the inner surface of the tubular structure 200.

In yet another alternative embodiment of the thermal process, the tube/jacket 1021 and/or the liner 1022 is not needed. Instead, a coating (e.g., external lamination) may be applied to fill some or all of the openings of the tubular structure 100. In this alternative embodiment, the barrier rod 1030 (e.g., composed of PTFE) is stretched and disposed within the lumen of the tubular structure 200. Heat is then applied to expand the barrier rod 1030 so that the rod contacts the inner surface of the tubular structure 200 and seals the lumen. Then, a coating of suitable material is applied over the tubular structure 200 filling and sealing the openings at the wall of the tubular structure 200, and forming the filler. Lastly, heat is applied to remove the barrier rod 1030 from the lumen of the tubular structure 200.

As used in this specification, the term "relaxed state" (e.g., a relaxed state of the tubular structure, a relaxed state of the catheter, etc.) refers to a state of an object in which no external force is applied against the object (other than the force due to gravity). For example, a relaxed state of a catheter may refer to a state of the catheter that is placed on a surface without having bending force, axial force, and torsional force applied to the catheter.

Although particular embodiments have been shown and described, it will be understood that it is not intended to limit the claimed inventions to the preferred embodiments, and it will be obvious to those skilled in the art that various changes and modifications (e.g., the dimensions and/or shapes of various parts) may be made without department from the spirit and scope of the claimed inventions. The specification and drawings are, accordingly, to be regarded in an illustrative rather than restrictive sense. The claimed inventions are intended to cover alternatives, modifications, and equivalents.

What is claimed is:

1. A method of making a medical device, the method comprising:
    obtaining an assembly having a tubular structure, a polymeric tube, and a stretched rod, wherein the stretched rod is inside a lumen of the polymeric tube, and wherein the polymeric tube is between the tubular structure and the stretched rod; and
    expanding the stretched rod to urge the polymeric tube radially outward towards an inner surface of the tubular structure while the tubular structure is surrounding at least a part of the polymeric tube;
    wherein the method further comprises:
        placing a jacket around the tubular structure;
        urging the jacket radially inward towards the tubular structure; and
        melting some materials of the jacket so that the materials flow into openings at a wall of the tubular structure.

2. The method of claim 1, wherein the act of expanding the stretched rod comprises heating the stretched rod.

3. The method of claim 1, wherein at least a part of the assembly is formed by inserting the stretched rod into the lumen of the polymeric tube.

4. The method of claim 1, wherein the act of expanding causes the stretched rod to become an expanded rod; and
    wherein the method further comprises stretching the expanded rod while the expanded rod is in the lumen of the polymeric tube, and removing the rod from the polymeric tube after the act of stretching is performed.

5. The method of claim 1, wherein the polymeric tube is a liner.

6. The method of claim 1, wherein the polymeric tube comprises a polymer.

7. The method of claim 6, wherein the act of expanding the stretched rod causes the polymeric tube to secure to the inner surface of the tubular structure.

8. The method of claim 1, wherein the polymeric tube comprises FEP, PTFE, PVDF, or PFA.

9. The method of claim 1, wherein the tubular structure is a hypotube of a catheter.

10. The method of claim 1, wherein the polymeric tube is made from a material having a lower melting point than a material of the stretched rod.

11. A method of making a medical device, the method comprising:
    obtaining an assembly having a tubular structure, a polymeric tube, and a stretched rod, wherein the stretched rod is inside a lumen of the polymeric tube, and wherein the polymeric tube is between the tubular structure and the stretched rod; and
    expanding the stretched rod to urge the polymeric tube radially outward towards an inner surface of the tubular structure while the tubular structure is surrounding at least a part of the polymeric tube
    wherein the polymeric tube comprises an adhesive layer, and wherein the act of expanding the stretched rod causes the polymeric tube to secure to the inner surface of the tubular structure via the adhesive layer.

12. The method of claim 11, further comprising:
    placing a jacket around the tubular structure; and
    urging the jacket radially inward towards the tubular structure.

13. The method of claim 12, wherein the act of urging the jacket radially inward comprises placing a heat-shrink tube around the jacket, and heating the heat-shrink tube to cause the heat-shrink tube to shrink radially inward, thereby pushing the jacket towards the tubular structure.

14. The method of claim 12, further comprising melting some materials of the jacket so that the materials flow into openings at a wall of the tubular structure.

15. The method of claim 12, wherein at least a part of the assembly is formed by inserting the stretched rod into the lumen of the polymeric tube, and wherein the jacket is placed around the tubular structure after the stretched rod is inserted into the lumen of the polymeric tube.

16. A method of making a medical device, the method comprising:
    obtaining an assembly having a tubular structure, a polymeric tube, and a stretched rod, wherein the tubular structure comprises a first end, a second end, and a tubular body extending between the first end and the second end, wherein the tubular structure comprises a plurality of openings extending through a wall-thickness of the tubular structure, wherein the stretched rod is inside a lumen of the polymeric tube, wherein the stretched rod comprises a rod that has been stretched before the stretched rod is incorporated into the assembly, and wherein the polymeric tube is radially between the tubular structure and the stretched rod; and
    expanding the stretched rod to urge the polymeric tube radially outward towards an inner surface of the tubular structure while the tubular structure surrounds at least a part of the polymeric tube, wherein the act of expanding causes the stretched rod to become an expanded rod;
    wherein the act of expanding causes the polymeric tube to be pressed by the expanded rod against the inner surface of the tubular structure.

17. The method of claim 16, wherein the act of expanding the stretched rod comprises heating the stretched rod.

18. The method of claim 16, further comprising:
    placing a jacket around the tubular structure; and
    urging the jacket radially inward towards the tubular structure.

19. The method of claim 18, wherein the act of urging comprises using a heat-shrink tube that is placed around the jacket, and wherein the method further comprises removing the heat-shrink tube after the jacket is urged towards the tubular structure.

20. The method of claim 18, further comprising melting some materials of the jacket so that the materials flow into the openings of the tubular structure.

21. The method of claim 16, wherein the act of expanding the stretched rod causes the polymeric tube to secure to the inner surface of the tubular structure.

22. The method of claim 18, wherein at least a part of the assembly is formed by inserting the stretched rod into the lumen of the polymeric tube, and wherein the jacket is placed around the tubular structure after the stretched rod is inserted into the lumen of the polymeric tube.

23. The method of claim 16, further comprising stretching the expanded rod while the expanded rod is in the lumen of the polymeric tube, and removing the rod from the polymeric tube after the act of stretching is performed.

24. The method of claim 16, wherein the polymeric tube comprises FEP, PTFE, PVDF, or PFA.

25. The method of claim 16, wherein the polymeric tube comprises an adhesive layer.

26. The method of claim 25, wherein the act of expanding the stretched rod causes the polymeric tube to secure to the inner surface of the tubular structure via the adhesive layer.

27. The method of claim 16, wherein the tubular structure is a hypotube of a catheter.

28. The method of claim 16, wherein the polymeric tube is made from a material having a lower melting point than a material of the stretched rod.

* * * * *